United States Patent [19]

Belanger et al.

[11] Patent Number: 4,863,958
[45] Date of Patent: Sep. 5, 1989

[54] BENZOFURAN DERIVATIVES USEFUL AS INHIBITORS OF MAMMALIAN LEUKOTRIENE BIOSYNTHESIS

[75] Inventors: Patrice C. Belanger; John Scheigetz, Dollard des Ormeaux; Joshua Rokach, Quebec, all of Canada

[73] Assignee: Merck Frosst Canada, Inc., Kirkland, Canada

[21] Appl. No.: 183,877

[22] Filed: Apr. 20, 1988

Related U.S. Application Data

[63] Continuation-in-part of Ser. No. 146,882, Jan. 22, 1988, abandoned, which is a continuation of Ser. No. 931,751, Nov. 17, 1986, abandoned, which is a continuation of Ser. No. 741,379, Jun. 7, 1985, abandoned, which is a continuation-in-part of Ser. No. 622,372, Jun. 20, 1984, abandoned.

[51] Int. Cl.$^4$ .................... A61K 31/34; C07D 307/80
[52] U.S. Cl. ................................. 514/469; 549/469; 549/470; 549/471
[58] Field of Search ................ 549/469, 470, 471; 546/196; 548/525; 514/320, 422, 469

[56] References Cited

U.S. PATENT DOCUMENTS 4,187,234  2/1980  Bernasconi et al. ............... 549/479

FOREIGN PATENT DOCUMENTS 2909754  9/1980  Fed. Rep. of Germany .

*Primary Examiner*—Mary C. Lee
*Assistant Examiner*—Bernard I. Dentz
*Attorney, Agent, or Firm*—Gabriel Lopez; Hesna J. Pfeiffer

[57] ABSTRACT

Benzofuran derivatives, pharmaceutical compositions and methods of treatment are disclosed. These compounds are useful as inhibitors of mammalian leukotriene biosynthesis. As such, these compounds are useful therapeutic agents for treating allergic conditions, asthma, cardiovascular disorders, inflammation. The compounds ar also useful as analgesics and as cytoprotective agents.

4 Claims, No Drawings

BENZOFURAN DERIVATIVES USEFUL AS INHIBITORS OF MAMMALIAN LEUKOTRIENE BIOSYNTHESIS

CROSS REFERENCE

This is a CIP of application U S. Ser. No. 146,882 filed Jan. 22, 1988, titled "Benzofuran Derivatives" in the names of Belanger et al. now abandoned, which is a coninuation of application U.S. Ser. No. 931,751, filed Nov. 17, 1986, abandoned, which is a continuation of application U.S. Ser. No. 741,379, filed June 7, 1985, abandoned, which is a CIP of application U.S. Ser. No. 622,372, filed June 20, 1984, abandoned.

BACKGROUND OF THE INVENTION

This invention involves certain benzofuran derivatives. These compounds are useful as inhibitors of mammalian leukotriene biosynthesis. As such, these compounds are useful therapeutic agents for treating allergic conditions, asthma, cardiovascular disorders and inflammation. The compounds are also useful as analgesics and as cytoprotective agents.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also affects other cell types such as lymphocytes and, for example, may modulate the action of T-suppressor cells and natural killer cells. When injected invivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. 5-lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. 5-lipoxygenase inhibitors would therefore be a new class of drugs for the treatment of asthma. See, for example, B. Samuelsson, *Science* 220, 568–575 (1983).

Psoriasis is a human skin disease which affects between two and six percent of the population. There is no adeguate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis, and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function.

SUMMARY OF THE INVENTION

It has now been discovered that certain substituted benzofurans and benzothiofurans of Formula I are effective inhibitors of leukotriene biosynthesis. Thus, these compounds are useful therapeutic agents for treating conditions such as asthma, allergies, cardiovascular disorders such as angina and inflammation, for amelioration of skin diseases like psoriasis and atopic eczema, and as cytoprotective agents.

DETAILED DESCRIPTION OF THE INVENTION

The compounds of the present invention are compounds of the formula:

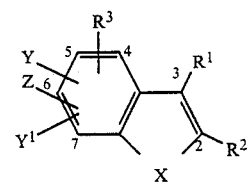

wherein:
each $R^1$ is independently hydrogen or $C_1$ to $C_6$ alkyl;

$R^2$ is hydrogen, $C_1$ to $C_6$ alkyl, —(CH$_2$)$_n$-Het-Y, or

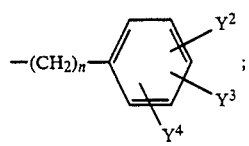

$R^3$ is hydroxyl,

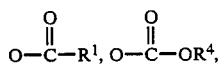

OCOCH$_2$CH$_2$COOH, OSO$_3$H, or OPO$_3$H$_2$;
each $R^4$ is independently $C_1$ to $C_6$ alkyl;
each $R^5$ is independently H, $C_1$ to $C_6$ alkyl, or both $R^5$s join to form a 5- or 6-membered ring with the N to which they are attached;
Het is a heterocyclic group selected from pyridine, pyrazine, pyrimidine, oxazole, pyrazole, oxadiazole, tetrazole, guinoline, thiophene, furan, pyrrole, thiazole, thiadiazole, or imidazole;
X is O, S, SO, SO$_2$;
Y, $Y^1$, $Y^2$, $Y^3$, $Y^4$ and Z are each independently H, halogen, OH, $C_1$ to $C_6$ alkyl, $C_2$ to $C_6$ alkenyl, —COOR$^1$, —COR$^1$, nitro, $C_1$ to $C_6$ alkoxy, $C_1$ to $C_6$ alkylthio, —CH$_2$SR$^1$, OCH$_2$CO$_2$R$^1$,

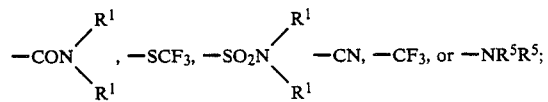

and each n is independently 0 to 10;
with the provisos that:
(a) not all of $R^1$, $R^2$, Y, $Y^1$, $Y^2$, $Y^3$, $Y^4$, and Z are simultaneously H;
(b) when up to 2 of $R^1$, $R^2$, Y, $Y^1$, and Z are $C_1$ to $C_2$ alkyl, and the others of $R^1$, $R^2$, Y, $Y^1$, and Z are H, then $R^3$ is not OH; and
(c) when n in

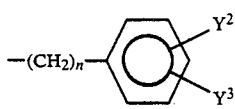

is O and one of $R^3$, Y, $Y^1$ or Z is OH, then $R^1$ is not H or $C_1$ to $C_2$ alkyl;
and the pharmaceutically acceptable salts thereof.

Unless otherwise indicated, the alkyl groups or alkyl portions of other groups may be straight chain, branched or cyclic or may contain both straight chain or branched and cyclic portions By halogen is meant fluorine, chlorine, bromine or iodine.

The heterocycles of —NR$^5$R$^5$ when R$^5$R$^5$ are joined include pyrrolidine, piperidine, and morpholine.

Preferred compounds of the present invention are compounds of Formula I as defined above, wherein:
each $R^1$ is $C_1$ to $C_3$ alkyl;
$R^2$ is hydrogen, $C_1$ to $C_3$ alkyl,

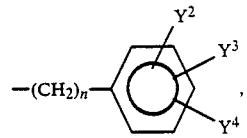

or —(CH$_2$)$_n$-Het-Y;
$R^3$ is hydroxyl,

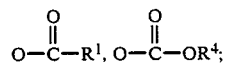

OCOCH$_2$CH$_2$COOH, OSO$_3$H, or OPO$_3$H$_2$;
each $R_4$ is independently $C_1$ to $C_3$ alkyl;
Het is heterocyclic group selected from pyridine, quinoline, thiazole, thiadiazole, or imidazole;
X is O or S;
Y, $Y^1$, $Y^2$, $Y^3$, $Y^4$, and Z are each independently H, halogen $C_1$ to $C_3$ alkyl, $C_2$ or $C_3$ alkenyl, —COOR$^1$, COR$^1$, $C_1$ to $C_3$ alkoxy, $C_1$ to $C_3$ alkylthio, —CH$_2$SR$^1$,

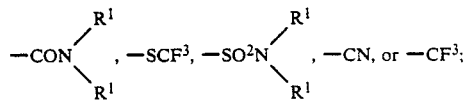

$Y^2$ is also OCH$_2$CO$_2$R$^1$;
each n is independently 0 to 4;
and the pharmaceutically acceptable salts thereof.

More preferred compounds of the present invention are compounds of the Formula I as defined above, wherein:
each $R^1$ is methyl;
$R^2$ is hydrogen,

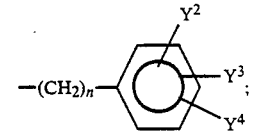

or —CH$_2$—Het—Y;
$R^3$ is 4-hydroxyl, 4-OSO$_3$H, or 4-OPO$_3$H$_2$;
Het is a pyridine;
n =1 or 2;
X is O; and
Y, $Y^1$, $Y^2$, $Y^3$, $Y^4$, and Z are each independently H, fluorine, chlorine, methyl, propyl, allyl, —COOR$^1$, —COR$^1$, methoxy, methylthio, —CH$_2$SR$^1$, or —CF$^3$;
and the pharmaceutically acceptable salts thereof.

Most preferred compounds of the present invention are compounds of Formula I as defined above, wherein:
each $R^1$ is methyl;
$R^2$ is

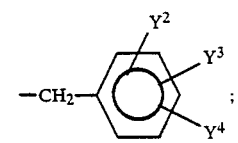

$R^3$ is 4-hydroxyl, 4-OPO$_3$H$_2$, or 4 OSO$_3$H;

Het is a pyridine;

X is O; and

Y, $Y^1$, $Y^2$, $Y^3$, $Y^4$, and Z are each independently H, fluorine, chlorine, propyl, allyl, methoxy, or $CH_2SR^1$;

and the pharmaceutically acceptable salts thereof.

Other most preferred compounds of the present invention are compounds of Formula I as defined above, wherein:

each $R^1$ is methyl;

$R^2$ is hydrogen;

$R^3$ is 4-hydroxyl, 4 $OPO_3H_2$, or 4-$OSO_3H$;

Het is a pyridine;

X is O; and

Y, $Y^1$, $Y^2$, $Y^3$, $Y^4$, and Z are each independently H, fluorine, chlorine, propyl, allyl, methoxy, or $CH^2SR^1$; and the pharmaceutically acceptable salts thereof.

Still other most preferred compounds of the present invention are compounds of Formula I as defined above, wherein:

each $R^1$ is methyl;

$R^2$ is —$CH_2$Het—Y;

$R^3$ is 4 hydroxyl, 4-$OPO_3H_2$, or 4 $OSO_3H$;

Het is a pyridine;

X is 0; and

Y, $Y^1$, $Y^2$, $Y^3$, $Y_4$, and Z are each independently H, fluorine, chlorine, propyl, allyl, methoxy, or $CH^2SR^1$;

and the pharmaceutically acceptable salts thereof.

Some of the compounds described herein contain one or more centers of asymmetry and may thus give rise to diastereoisomers and optioal isomers. The present invention is meant to comprehend such possible diastereoisomers as well as their racemic and resolved optically active forms.

Tables 1–4 list compounds of Formula I of this invention.

TABLE 1
COMPOUNDS OF FORMULA I

| | R¹ | R² | R³ | X | Y | Y¹ | Y² | Y³ | Y⁴ |
|---|---|---|---|---|---|---|---|---|---|
| 2 | CH₃ | H | 4-OCO₂CH₃ | O | H | H | — | — | — |
| 4 | CH₃ | H | 4-OH | O | 5-allyl | H | — | — | — |
| 5 | CH₃ | H | 4-OCO₂CH₃ | O | 5-propyl | H | — | — | — |
| 6 | CH₃ | H | 4-OH | O | 7-propyl | H | — | — | — |
| 7 | CH₃ | H | 4-OH | O | 5-allyl | H | — | — | — |
| 8 | CH₃ | C₂H₅ | 4-OH | O | 5-propyl | H | — | — | — |
| 9 | CH₃ | CH₂C₆H₅ | 4-OH | O | 5-propyl | H | H | H | H |
| 10 | C₃H₇ | H | 4-Oallyl | O | H | H | — | — | — |
| 11 | C₃H₇ | H | 4-OH | O | H | H | — | — | — |
| 12 | C₃H₇ | H | 4-OH | O | 5-allyl | H | — | — | — |
| 13 | C₆H₅ | H | 4-OH | O | H | H | H | H | H |
| 14 | CH₃ | CH₂ 4-pyridyl | 4-OH | O | 5-propyl | H | H | H | H |
| 15 | CH₃ | CH₂C₆H₅ | 5-OH | O | 6-OH | H | 4-OH | H | H |
| 16 | CH₃ | CH₂C₆H₅ | 4-OH | O | 5-propyl | H | 4-OCH₃ | H | — |
| 17 | CH₃ | CH₂C₆H₅ | 4-OH | O | 5-propyl | H | — | — | — |
| 21 | CH₃ | H | 5,6-OCH₂O | O | H | H | — | — | — |
| 22 | CH₃ | H | 4-OCH₃ | O | 7-propyl | H | 4-OH | H | H |
| 24 | CH₃ | CH₂C₆H₅ | 4-OCO₂CH₃ | O | 5-propyl | H | 4-OCH₃ | H | H |
| 25 | CH₃ | CH₂C₆H₅ | 4-OCO₂CH₃ | O | 5-propyl | 7-F | H | H | H |
| 26 | CH₃ | CH₂C₆H₅ | 4-OH | O | 5-propyl | 7-F | 4-OH | H | H |
| 27 | CH₃ | CH₂C₆H₅ | 4-OH | O | 5-propyl | 7-F | 4-OCH₃ | H | H |
| 28 | CH₃ | CH₂C₆H₅ | 4-OH | O | 5-propyl | 7-F | 4-F | H | H |
| 29 | CH₃ | CH₂C₆H₅ | 4-OH | O | 5-propyl | 7-F | 4-Cl | H | H |
| 30 | CH₃ | CH₂C₆H₅ | 4-OH | O | 5-propyl | 7-F | 4-N(CH₃)₂ | H | H |
| 31 | CH₃ | CH₂C₆H₅ | 4-OH | O | 5-propyl | H | 4-F | H | H |
| 32 | CH₃ | CH₂C₆H₅ | 4-OH | O | 5-propyl | H | 4-Cl | H | H |
| 33 | CH₃ | CH₂C₆H₅ | 4-OH | O | 5-propyl | H | 4-N(CH₃)₂ | H | H |
| 34 | CH₃ | CH₂C₆H₅ | 4-OH | O | 5-propyl | 7-F | H | H | H |
| 35 | CH₃ | CH₂C₆H₅ | 4-OH | O | 5-propyl | 7-F | 4-F | H | H |
| 36 | C₃H₇ | CH₂C₆H₅ | 4-OH | O | 5-propyl | 7-F | 4-OH | H | H |
| 37 | C₃H₇ | CH₂C₆H₅ | 4-OH | O | 5-propyl | 7-F | 4-OCH₃ | H | H |
| 38 | C₃H₇ | CH₂C₆H₅ | 4-OH | O | 5-propyl | 7-F | 4-N(CH₃)₂ | H | H |
| 39 | C₃H₇ | CH₂C₆H₅ | 4-OH | O | 5-propyl | H | 4-OCH₃ | H | H |
| 40 | C₃H₇ | CH₂C₆H₅ | 4-OH | O | 5-propyl | H | 4-N(CH₃)₂ | H | H |
| 41 | C₃H₇ | CH₂C₆H₅ | 4-OH | O | 5-propyl | H | 4-OCH₃ | H | H |
| 42 | C₃H₇ | CH₂C₆H₅ | 5-OH | O | 6-OH | H | 4-OH | H | H |
| 43 | C₃H₇ | CH₂C₆H₅ | 5-OH | O | 6-OH | H | 4-F | H | H |
| 44 | CH₃ | CH₂C₆H₅ | 6-OH | O | H | H | 4-OCH₃ | H | H |
| 45 | CH₃ | CH₂C₆H₅ | 4-OH | O | 5-propyl | H | 4-OCH₃ | H | H |
| 46 | CH₃ | CH₂C₆H₅ | 4-OH | O | 5-allyl | H | 4-OCH₃ | H | H |
| 48 | CH₃ | CH₂C₆H₅ | 4-OH | O | 5-CH₂SCH₃ | H | 4-OCH₃ | H | H |
| 49 | CH₃ | CH₂C₆H₅ | 4-OH | O | 5-CH₂OCH₃ | H | 4-OCH₃ | H | H |
| 50 | CH₃ | CH₂ 6-quinoline | 4-OH | O | 5-propyl | H | H | H | H |
| 51 | CH₃ | CH₂ 3-furan | 4-OH | O | 5-propyl | H | H | H | H |
| 52 | CH₃ | CH₂ 3-thiophene | 4-OH | O | 5-propyl | H | H | H | H |
| 53 | CH₃ | CH₂ 3-pyrrole | 4-OH | O | 5-propyl | H | H | H | H |
| 54 | CH₃ | CH₂ 2-pyridyl | 4-OH | O | 5-propyl | H | H | H | H |
| 55 | CH₃ | CH₂—thiadiazole | 4-OH | O | 5-propyl | H | H | H | H |
| 56 | CH₃ | CH₂ thiazole | 4-OH | O | 5-propyl | H | H | H | H |
| 57 | CH₃ | CH₂CH₂C₆H₅ | 4-OH | O | 5-propyl | H | 4-OCH₃ | H | H |
| 58 | CH₃ | C₆H₅ | 4-OH | O | 5-propyl | H | 4-OCH₃ | H | H |

TABLE 1-continued

COMPOUNDS OF FORMULA I

| | $R^1$ | $R^2$ | $R^3$ | X | Y | $Y^1$ | $Y^2$ | $Y^3$ | $Y^4$ |
|---|---|---|---|---|---|---|---|---|---|
| 59 | CH₃ | C₆H₅ | 4-OH | O | 5-propyl | H | 4-OH | H | H |
| 60 | CH₃ | C₆H₅ | 4-OH | O | 5-propyl | H | 4-F | H | H |
| 61 | CH₃ | C₆H₅ | 4-OH | S | 5-propyl | H | 4-OCH₃ | H | H |
| 62 | CH₃ | CH₂C₆H₅ | 4-OH | S | 5-propyl | H | H | H | H |
| 63 | CH₃ | CH₂C₆H₅ | 4-OH | S | 5-propyl | 7-F | 4-OCH₃ | H | H |
| 64 | CH₃ | CH₂C₆H₅ | 4-OH | S | 5-propyl | 7-F | 4-F | H | H |
| 65 | CH₃ | CH₂C₆H₅ | 5-OH | S | 5-propyl | H | 4-OCH₃ | H | H |
| 66 | CH₃ | CH₂C₆H₅ | 4-OH | S | 6-OH | H | 4-OCH₃ | H | H |
| 67 | CH₃ | CH₂C₆H₅ | 5-OH | SO | 5-propyl | 7-F | 4-OCH₃ | H | H |
| 68 | CH₃ | CH₂C₆H₅ | 4-OH | SO₂ | 5-propyl | 7-F | 4-OCH₃ | H | H |
| 69 | CH₃ | CH₂C₆H₅ | 4-OH | O | 5-COCH₃ | 7-F | 4-OCH₃ | H | H |
| 70 | CH₃ | CH₂C₆H₅ | 4-OH | O | 5-COCH₃ | H | 4-Cl | H | H |
| 72 | CH₃ | CCH₂C₆H₅ | 4-OH | O | H | 7-Cl | 4-OCH₃ | 3-CHO | H |
| 73 | CH₃ | CH₂C₆H₅ | 4-OH | O | 5-propyl | 7-Cl | 4-Br | H | H |
| 74 | CH₃ | CH₂C₆H₅ | 4-OH | O | 5-propyl | H | 4-Cl | H | H |
| 75 | CH₃ | CH₂C₆H₅ | 4-OAc | O | 4-propyl | 7-Cl | 4-F | H | H |
| 76 | CH₃ | CH₂C₆H₅ | 5-OH | O | 5-propyl | 7-Cl | 4-OAc | H | H |
| 77 | CH₃ | CH₂C₆H₅ | 4-OAc | O | 5-propyl | H | 4-OH | H | H |
| 78 | CH₃ | CH₂C₆H₅ | 4-OAc | O | 4-propyl | H | 4-OH | H | H |
| 79 | CH₃ | CH₂C₆H₅ | 5-OH | O | H | H | 4-OH | H | H |
| 80 | CH₃ | CH₂C₆H₅ | 7-OH | O | H | H | 4-OCH₃ | H | H |
| 81 | CH₃ | CH₂C₆H₅ | 4-Oallyl | O | 5-propyl | H | 4-OCH₃ | H | H |
| 82 | CH₃ | CH₂C₆H₅ | 4-OAc | O | 5-propyl | 7-Cl | 4-OCH₃ | H | H |
| 84 | CH₃ | CH₂C₆H₅ | 4-OAc | O | 5-propyl | 7-F | 4-OCH₃ | H | H |
| 85 | CH₃ | CH₂C₆H₅ | 4-OCO₂CHClCH₃ | O | 5-propyl | 7-Cl | 4-OCH₃ | H | H |
| 86 | CH₃ | CH₂C₆H₅ | 4-OCO₂CH₃ | O | 5-propyl | 7-F | 4-OCH₃ | H | H |
| 87 | CH₃ | CH₂C₆H₅ | 4-OCO₂CH₃ | O | 5-propyl | 7-Cl | 4-OCH₃ | H | H |
| 88 | CH₃ | CH₂C₆H₅ | 4-OH | O | 4-propyl | 7-Br | 4-OCH₃ | H | H |
| 89 | CH₃ | CH₂C₆H₅ | 4-OH | O | 4-propyl | 7-Cl | 4-OCH₃ | H | H |
| 90 | CH₃ | CH₂C₆H₅ | 4-OH | O | H | H | 4-OCH₃ | H | H |
| 91 | CH₃ | CH₂C₆H₅ | 4-OH | O | H | H | 4-OCH₃ | H | H |
| 92 | CH₃ | CH₂C₆H₅ | 4-OH | O | 5-allyl | H | 4-OCH₃ | H | H |
| 93 | CH₃ | CH₂C₆H₅ | 4-OH | O | H | 7-CH₃ | 4-OCH₃ | H | H |
| 94 | CH₃ | CH₂C₆H₅ | 4-OH | O | 7-propyl | 7-Pr | 4-OCH₃ | H | H |
| 95 | CH₃ | CH₂C₆H₅ | 4-OH | O | 5-propyl | 7-Pr | 4-OCH₃ | H | H |
| 96 | CH₃ | CH₂C₆H₅ | 4-OH | O | 5-Cl | 7-Cl | 4-OCH₃ | H | H |
| 97 | CH₃ | CH₂C₆H₅ | 4-OPO₃H₂ | O | 5-propyl | 7-F | 4-OCH₃ | H | H |
| 98 | CH₃ | CH₂C₆H₅ | 4-OCOCH₂CH₂CO₂H | O | 5-propyl | 7-Cl | 4-OCH₃ | H | H |
| 99 | CH₃ | CH₂C₆H₅ | 4-OCOCH₂CH₂CO₂H | O | 5-propyl | 7-Cl | 4-OCH₃ | H | H |
| 100 | CH₃ | CH₂C₆H₅ | 5-OAc | O | 4-propyl | H | 4-OCH₃ | H | H |
| 101 | CH₃ | CH₂C₆H₅ | 5-OCO₂CH₃ | O | 4-propyl | H | 4-OCH₃ | H | H |
| 102 | CH₃ | CH₂C₆H₅ | 5-OH | O | 4-propyl | 7-Cl | 4-OCH₂CO₂Et | H | H |
| 103 | CH₃ | CH₂C₆H₅ | 4-OH | O | 5-propyl | 7-Cl | 4-OCH₂CO₂H | H | H |
| 105 | CH₃ | CH₂C₆H₅ | 4-OAc | O | 5-propyl | H | H | H | H |
| 107 | CH₃ | CH₂C₆H₅ | 4-OH | O | 5-propyl | H | H | H | H |
| 108 | CH₃ | CH₂C₆H₅ | 4-OH | O | 5-propyl | 7-Cl | 4-OH | H | H |
| 109 | CH₃ | CH₂C₆H₅ | 4-OAc | O | H | 7-Cl | 4-OCH₃ | H | H |
| 110 | CH₃ | CH₂C₆H₅ | 4-OH | O | H | H | 4-OCH₃ | H | H |
| 111 | CH₃ | CH₂CH₂C₆H₅ | 4-OH | O | 5-propyl | H | 4-OCH₃ | H | H |
| 112 | CH₃ | CH₂CH₂C₆H₅ | 4-OH | O | 5-propyl | 7-Cl | 4-OCH₃ | H | H |
| 113 | CH₃ | CH₂CH₂C₆H₅ | 4-OH | O | 5-propyl | H | 4-OCH₃ | H | H |

TABLE 1-continued
COMPOUNDS OF FORMULA I

| | R¹ | R² | R³ | X | Y | Y¹ | Y² | Y³ | Y⁴ |
|---|---|---|---|---|---|---|---|---|---|
| 114 | CH₃ | CH₂C₆H₅ | 4-OSO₃H | O | 5-propyl | 7-Cl | 4-OCH₃ | H | H |
| 115 | CH₃ | CH₂C₆H₅ | 4-OH | O | 5-propyl | 7-Cl | 4-SCH₃ | H | H |
| 116 | CH₃ | CH₂C₆H₅ | 4-OH | O | CH₂SCH₃ | 7-Cl | 4-OCH₃ | H | H |
| 117 | CH₃ | CH₂C₆H₅ | 4-OH | O | CH₂SOCH₃ | 7-Cl | 4-OCH₃ | H | H |
| 118 | CH₃ | CH₂C₆H₅ | 4-OH | O | CH₂SO₂CH₃ | 7-Cl | 4-OCH₃ | H | H |
| 119 | CH₃ | CH₂C₆H₅ | 4-OH | O | CH₂OCH₃ | 7-Cl | 4-OCH₃ | H | H |
| 120 | CH₃ | CH₂C₆H₅ | 4-OSO₃H | O | CH₂SCH₃ | 7-Cl | 4-OCH₃ | H | H |
| 121 | CH₃ | CH₂C₆H₅ | 4-OCOCH₂CH₂CO₂H | O | CH₂SCH₃ | 7-Cl | 4-OCH₃ | H | H |
| 122 | CH₃ | CH₂C₆H₅ | 4-OPO₃H₂ | O | CH₂SO₂CH₃ | 7-Cl | 4-OCH₃ | H | H |
| 123 | CH₃ | CH₂C₆H₅ | 4-OPO₃H₂ | O | CH₂SCH₃ | 7-Cl | 4-OCH₃ | H | H |
| 124 | CH₃ | CH₂C₆H₅ | 4-OH | O | CH₂SOCH₃ | 7-F | 4-OCH₃ | H | H |
| 125 | CH₃ | CH₂C₆H₅ | 4-OH | O | CH₂SO₂CH₃ | 7-F | 4-OCH₃ | H | H |
| 126 | CH₃ | CH₂C₆H₅ | 4-OH | O | CH₂SCH₃ | 7-F | 4-OCH₃ | H | H |
| 127 | CH₃ | CH₂C₆H₅ | 4-OH | O | CH₂OCH₃ | 7-F | 4-OCH₃ | H | H |
| 128 | CH₃ | CH₂C₆H₅ | 4-OSO₃H | O | CH₂SCH₃ | 7-F | 4-OCH₃ | H | H |
| 129 | CH₃ | CH₂C₆H₅ | 4-OCOCH₂CH₂CO₂H | O | CH₂SCH₃ | 7-F | 4-OCH₃ | H | H |
| 130 | CH₃ | CH₂C₆H₅ | 4-OPO₃H₂ | O | CH₂SO₂CH₃ | 7-F | 4-OCH₃ | H | H |
| 131 | CH₃ | CH₂C₆H₅ | 4-OPO₃H₂ | O | CH₂SCH₃ | 7-F | 4-OCH₃ | H | H |
| 132 | CH₃ | CH₂C₆H₅ | 4-OH | O | CH₂SCH₃ | 7-Pr | 4-OCH₃ | H | H |
| 133 | CH₃ | CH₂C₆H₅ | 4-OH | O | CH₂SOCH₃ | 7-Pr | 4-OCH₃ | H | H |
| 134 | CH₃ | CH₂C₆H₅ | 4-OH | O | CH₂SO₂CH₃ | 7-Pr | 4-OCH₃ | H | H |
| 135 | CH₃ | CH₂C₆H₅ | 4-OH | O | CH₂OCH₃ | 7-Pr | 4-OCH₃ | H | H |
| 136 | CH₃ | CH₂C₆H₅ | 4-OSO₃H | O | CH₂SCH₃ | 7-Pr | 4-OCH₃ | H | H |
| 137 | CH₃ | CH₂C₆H₅ | 4-OCOCH₂CH₂CO₂H | O | CH₂SCH₃ | 7-Pr | 4-OCH₃ | H | H |
| 138 | CH₃ | CH₂C₆H₅ | 4-OPO₃H₂ | O | CH₂SO₂CH₃ | 7-Pr | 4-OCH₃ | H | H |
| 139 | CH₃ | CH₂C₆H₅ | 4-OPO₃H₂ | O | CH₂SCH₃ | 7-Pr | 4-OCH₃ | H | H |
| 140 | CH₃ | CH₂C₆H₅ | 4-OH | O | 5-propyl | 7-CO₂H | 4-OCH₃ | H | H |
| 141 | CH₃ | CH₂C₆H₅ | 4-OH | O | 5-propyl | 7-F | 4-CO₂H | H | H |
| 142 | CH₃ | CH₂C₆H₅ | 4-OH | O | 5-propyl | 7-Cl | 4-CO₂H | H | H |
| 143 | CH₃ | CH₂C₆H₅ | 4-OH | O | 5-CH₂CHOHCH₂OH | 7-F | 4-CO₂H | H | H |
| 144 | CH₃ | CH₂C₆H₅ | 4-OH | O | 5-CH₂CHOHCH₂OH | 7-Cl | 4-CO₂H | H | H |
| 145 | CH₃ | CH₂C₆H₅ | 4-OH | O | 5-CH₂CHOHCH₃ | 7-F | 4-CO₂H | H | H |
| 146 | CH₃ | CH₂C₆H₅ | 4-OH | O | 5-CH₂CHOHCH₃ | 7-Cl | 4-CO₂H | H | H |
| 147 | CH₃ | CH₂C₆H₅ | 4-OH | O | 5-propyl | 7-SO₃H | 4-OCH₃ | H | H |
| 148 | CH₃ | CH₂C₆H₅ | 4-OH | O | 5-C(CH₃)₂H₂OH | 7-Cl | 4-CO₂H | H | H |
| 149 | CH₃ | CH₂C₆H₅ | 4-OH | O | 5-C(CH₃)₃ | 7-Cl | 4-CO₂H | H | H |
| 150 | CH₃ | CH₂C₆H₅ | 4-OH | O | 5-C(CH₃)₃ | 7-CH₃ | 4-CO₂H | H | H |
| 151 | CH₃ | CH₂tetrazol | 4-OH | O | 5-propyl | 7-Cl | 4-CH₃O | H | H |
| 152 | CH₃ | CH₂tetrazol | 4-OH | O | 5-propyl | 7-CH₃ | 4-CH₃O | H | H |
| 153 | CH₃ | CH₂tetrazol | 4-OH | O | 5-propyl | 7-F | 4-CH₃O | H | H |
| 154 | CH₃ | CH₂tetrazol | 4-OH | O | 5-CH₂CHOHCH₃ | 7-F | 4-CH₃O | H | H |
| 155 | CH₃ | CH₂tetrazol | 5-OH | O | 5-propyl | 7-Pr | 4-CH₃O | H | H |
| 156 | CH₃ | CH₂C₆H₅ | 4-OAc | O | 5-propyl | 7-Pr | 4-CH₃O | H | H |
| 157 | CH₃ | CH₂C₆H₅ | 4-OH | O | H | H | H | H | H |
| 158 | CH(CH₃)₂ | CH₂C₆H₅ | 4-OH | O | 5-propyl | 7-Cl | 4-CH₃O | H | H |
| 159 | CH(CH₃)₂ | CH₂C₆H₅ | 4-OH | O | H | H | 4-CH₃O | H | H |
| 160 | CH(CH₃)₂ | H | 4-OH | O | 5-propyl | 7-Cl | — | — | — |
| 161 | CH(CH₃)₂ | H | 4-OH | O | H | H | — | — | — |
| 162 | CH₃ | CH₂C₆H₅ | 4-OH | O | 5-propyl | 7-Cl | 4-CH₃O | H | H |
| 163 | | | | | | 7-Cl | 4-CH₃O | H | H |
| 164 | | | | | | | | | |

TABLE 1-continued

COMPOUNDS OF FORMULA I

| | $R^1$ | $R^2$ | $R^3$ | X | Y | $Y^1$ | $Y^2$ | $Y^3$ | $Y^4$ |
|---|---|---|---|---|---|---|---|---|---|
| 165 | CH$_3$ | CH$_2$C$_6$H$_5$ | 4-OH | O | 5-C$_4$H$_9$ | 7-Cl | 4-CH$_3$O | H | H |
| 166 | H | CH$_2$C$_6$H$_5$ | 4-OH | O | 5-propyl | 7-Cl | 4-CH$_3$O | H | H |
| 167 | Propyl | CH$_2$C$_6$H$_5$ | 4-OH | O | 5-propyl | 7-Cl | 4-CH$_3$O | H | H |
| 168 | CH$_3$ | CH$_3$CH—C$_6$H$_5$ | 4-OH | O | 5-propyl | 7-Cl | 4-CH$_3$O | H | — |
| 169 | CH$_3$ | C$_7$H$_{15}$ | 4-OH | O | 5-propyl | H | — | — | H |
| 170 | CH$_3$ | CH$_2$C$_6$H$_5$ | 4-OH | O | 5-propyl | 6-OMe | 4-CH$_3$O | H | H |
| 171 | CH$_3$ | C$_6$H$_5$ | 4-OH | S | 5-propyl | 7-Cl | H | H | H |
| 172 | CH$_3$ | CH$_2$C$_6$H$_5$ | 4-OH | O | 5-Cl | 7-Cl | 4-CH$_3$O | H | H |
| 173 | CH$_3$ | CH$_2$C$_6$H$_5$ | 4-OH | O | 5-propyl | 7-Cl | 4-Cl | 4-CH$_3$O | H |
| 174 | CH$_3$ | CH$_2$C$_6$H$_5$ | 4-OH | O | 5-propyl | 7-Cl | 2-CH$_3$O | H | H |
| 175 | CH$_3$ | CH$_2$C$_6$H$_5$ | 4-OH | O | 5-CH$_2$NMe$_2$ | 7-CH$_2$NMe$_2$ | 4-CH$_3$O | H | H |
| 176 | CH$_3$ | CH$_2$C$_6$H$_5$ | 4-OH | O | 5-Me | 7-Cl | 4-CH$_3$O | H | H |
| 177 | CH$_3$ | CH$_2$C$_6$H$_5$ | 4-OH | O | 5-allyl | 7-Cl | 4-CH$_3$O | H | H |
| 178 | CH$_3$ | CH$_2$C$_6$H$_5$ | 4-OH | O | 5-(CH$_2$)$_3$OH | 7-Cl | 4-CH$_3$O | H | H |
| 179 | CH$_3$ | CH$_2$C$_6$H$_5$ | 4-OH | O | 5-(CH$_2$)$_2$CO$_2$H | 7-Cl | 4-CH$_3$O | H | H |
| 180 | CH$_3$ | CH$_2$C$_6$H$_5$ | 4-OH | O | 5-EtO | 7-Cl | 4-CH$_3$O | H | H |

TABLE 2

Perferred Compounds of Formula I

| | R¹ | R² | R³ | X | Y | Y¹ | Y² | Y³ | Y⁴ |
|---|---|---|---|---|---|---|---|---|---|
| 5 | CH₃ | H | 4-OH | O | 5-propyl | H | — | — | — |
| 8 | CH₃ | C₂H₅ | 4-OH | O | 5-allyl | H | — | — | — |
| 14 | CH₃ | CH₂ 4-pyridyl | 4-OH | O | 5-propyl | H | H | H | H |
| 15 | CH₃ | CH₂C₆H₅ | 5-OH | O | 6-OH | H | H | H | H |
| 16 | CH₃ | CH₂C₆H₅ | 4-OH | O | 5-propyl | H | 4-OH | H | H |
| 17 | CH₃ | CH₂C₆H₅ | 4-OH | O | 5-propyl | H | 4-OCH₃ | H | H |
| 26 | CH₃ | CH₂C₆H₅ | 4-OH | O | 5-propyl | 7-F | H | H | H |
| 27 | CH₃ | CH₂C₆H₅ | 4-OH | O | 5-propyl | 7-F | 4-OH | H | H |
| 28 | CH₃ | CH₂C₆H₅ | 4-OH | O | 5-propyl | 7-F | 4-OCH₃ | H | H |
| 29 | CH₃ | CH₂C₆H₅ | 4-OH | O | 5-propyl | 7-F | 4-F | H | H |
| 30 | CH₃ | CH₂C₆H₅ | 4-OH | O | 5-propyl | 7-F | 4-Cl | H | H |
| 32 | CH₃ | CH₂C₆H₅ | 4-OH | O | 5-propyl | H | 4-F | H | H |
| 33 | CH₃ | CH₂C₆H₅ | 4-OH | O | 5-propyl | H | 4-Cl | H | H |
| 34 | CH₃ | CH₂C₆H₅ | 4-OH | O | 5-propyl | H | 4-N(CH₃)₂ | H | H |
| 35 | CH₃ | CH₂C₆H₅ | 4-OH | O | 5-propyl | H | H | H | H |
| 39 | CH₃ | CH₂C₆H₅ | 4-OH | O | 5-propyl | 7-F | 4-N(CH₃)₂ | H | H |
| 44 | CH₃ | CH₂C₆H₅ | 5-OH | O | H | H | 4-OCH₃ | H | H |
| 46 | CH₃ | CH₂C₆H₅ | 4-OH | O | 5-allyl | H | 4-OCH₃ | H | H |
| 48 | CH₃ | CH₂C₆H₅ | 4-OH | O | 5-CH₂SCH₃ | H | 4-OCH₃ | H | H |
| 49 | CH₃ | CH₂C₆H₅ | 4-OH | O | 5-CH₂OCH₃ | H | H | H | H |
| 50 | CH₃ | CH₂ 6-quinoline | 4-OH | O | 5-propyl | H | H | H | H |
| 51 | CH₃ | CH₂ 3-furan | 4-OH | O | 5-propyl | H | H | H | H |
| 52 | CH₃ | CH₂ 3-thiophene | 4-OH | O | 5-propyl | H | H | H | H |
| 53 | CH₃ | CH₂ 3-pyrrole | 4-OH | O | 5-propyl | H | H | H | H |
| 54 | CH₃ | CH₂ 2-pyridyl | 4-OH | O | 5-propyl | H | H | H | H |
| 55 | CH₃ | CH₂—thiadiazole | 4-OH | O | 5-propyl | H | H | H | H |
| 56 | CH₃ | CH₂ thiazole | 4-OH | O | 5-propyl | H | H | H | H |
| 73 | CH₃ | CH₂C₆H₅ | 4-OH | O | 5-propyl | 7-Cl | 4-OCH₃ | 3-CHO | H |
| 74 | CH₃ | CH₂C₆H₅ | 4-OH | O | 5-propyl | 7-Cl | 4-Br | H | H |
| 75 | CH₃ | CH₂C₆H₅ | 4-OH | O | 5-propyl | H | 4-Cl | H | H |
| 76 | CH₃ | CH₂C₆H₅ | 5-OH | O | 4-propyl | 7-Cl | 4-F | H | H |
| 77 | CH₃ | CH₂C₆H₅ | 4-OAc | O | 5-propyl | 7-Cl | 4-OAc | H | H |
| 78 | CH₃ | CH₂C₆H₅ | 4-OAc | O | 5-propyl | H | 4-OH | H | H |
| 79 | CH₃ | CH₂C₆H₅ | 5-OH | O | 4-propyl | H | 4-OH | H | H |
| 80 | CH₃ | CH₂C₆H₅ | 5-OH | O | H | H | 4-OH | H | H |
| 81 | CH₃ | CH₂C₆H₅ | 7-OH | O | H | H | 4-OCH₃ | H | H |
| 82 | CH₃ | CH₂C₆H₅ | 4-Oallyl | O | H | H | 4-OCH₃ | H | H |
| 84 | CH₃ | CH₂C₆H₅ | 4-OAc | O | 5-propyl | 7-Cl | 4-OCH₃ | H | H |
| 85 | CH₃ | CH₂C₆H₅ | 4-OAc | O | 5-propyl | 7-F | 4-OCH₃ | H | H |
| 86 | CH₃ | CH₂C₆H₅ | 4-OCO₂CHClCH₃ | O | 5-propyl | 7-Cl | 4-OCH₃ | H | H |
| 87 | CH₃ | CH₂C₆H₅ | 4-OCO₂CH₃ | O | 5-propyl | 7-F | 4-OCH₃ | H | H |
| 88 | CH₃ | CH₂C₆H₅ | 4-OCO₂CH₃ | O | 5-propyl | 7-Cl | 4-OCH₃ | H | H |
| 89 | CH₃ | CH₂C₆H₅ | 4-OH | O | 5-propyl | 7-Br | 4-OCH₃ | H | H |
| 90 | CH₃ | CH₂C₆H₅ | 4-OH | O | 5-propyl | 7-Cl | 4-CH₃O | H | H |
| 91 | CH₃ | CH₂C₆H₅ | 4-OH | O | 5-allyl | H | 4-OCH₃ | H | H |
| 92 | CH₃ | CH₂C₆H₅ | 4-OH | O | H | H | 4-OCH₃ | H | H |
| 93 | CH₃ | CH₂C₆H₅ | 4-OH | O | 7-propyl | H | 4-OCH₃ | H | H |
| 94 | CH₃ | CH₂C₆H₅ | 4-OH | O | 5-propyl | 7-CH₃ | 4-OCH₃ | H | H |
| 95 | CH₃ | CH₂C₆H₅ | 4-OH | O | 5-propyl | 7-Pr | 4-OCH₃ | H | H |
| 96 | CH₃ | CH₂C₆H₅ | 4-OH | O | 5-Cl | 7-Pr | 4-OCH₃ | H | H |
| 97 | CH₃ | CH₂C₆H₅ | 4-OPO₃H₂ | O | 5-propyl | 7-Cl | 4-OCH₃ | H | H |
| 98 | CH₃ | CH₂C₆H₅ | 4-OCOCH₂CH₂CO₂H | O | 5-propyl | 7-F | 4-OCH₃ | H | H |
| 99 | CH₃ | CH₂C₆H₅ | 4-OCOCH₂CH₂CO₂H | O | 5-propyl | 7-Cl | 4-OCH₃ | H | H |
| 100 | CH₃ | CH₂C₆H₅ | 5-OAc | O | 4-propyl | H | 4-OCH₃ | H | H |
| 101 | CH₃ | CH₂C₆H₅ | 5-OCO₂CH₃ | O | 4-propyl | H | 4-OCH₃ | H | H |
| 102 | CH₃ | CH₂C₆H₅ | 5-OH | O | 4-propyl | H | 4-OCH₃ | H | H |
| 103 | CH₃ | CH₂C₆H₅ | 4-OAc | O | 5-propyl | 7-Cl | 4-OCH₂CO₂Et | H | H |
| 105 | CH₃ | CH₂C₆H₅ | 4-OH | O | 5-propyl | 7-Cl | 4-OCH₂CO₂H | H | H |
| 107 | CH₃ | CH₂C₆H₅ | 4-OH | O | 5-propyl | H | H | H | H |
| 108 | CH₃ | CH₂C₆H₅ | 4-OH | O | 5-propyl | 7-Cl | H | H | H |
| 110 | CH₃ | CH₂CH₂C₆H₅ | 4-OAc | O | H | H | 4-OCH₃ | H | H |
| 111 | CH₃ | CH₂CH₂C₆H₅ | 4-OH | O | H | H | 4-OCH₃ | H | H |
| 112 | CH₃ | CH₂CH₂C₆H₅ | 4-OH | O | 5-propyl | 7-Cl | 4-OCH₃ | H | H |
| 113 | CH₃ | CH₂CH₂C₆H₅ | 4-OH | O | 5-propyl | H | 4-OCH₃ | H | H |
| 114 | CH₃ | CH₂C₆H₅ | 4-OSO₃H | O | 5-propyl | 7-Cl | 4-OCH₃ | H | H |
| 115 | CH₃ | CH₂C₆H₅ | 4-OH | O | 5-propyl | 7-Cl | 4-SCH₃ | H | H |
| 116 | CH₃ | CH₂C₆H₅ | 4-OH | O | CH₂SCH₃ | 7-Cl | 4-OCH₃ | H | H |
| 117 | CH₃ | CH₂C₆H₅ | 4-OH | O | CH₂SOCH₃ | 7-Cl | 4-OCH₃ | H | H |
| 118 | CH₃ | CH₂C₆H₅ | 4-OH | O | CH₂SO₂CH₃ | 7-Cl | 4-OCH₃ | H | H |
| 119 | CH₃ | CH₂C₆H₅ | 4-OH | O | CH₂OCH₃ | 7-Cl | 4-OCH₃ | H | H |
| 120 | CH₃ | CH₂C₆H₅ | 4-OSO₃H | O | CH₂SCH₃ | 7-Cl | 4-OCH₃ | H | H |
| 121 | CH₃ | CH₂C₆H₅ | 4-OCOCH₂CH₂CO₂H | O | CH₂SCH₃ | 7-Cl | 4-OCH₃ | H | H |
| 122 | CH₃ | CH₂C₆H₅ | 4-OPO₃H₂ | O | CH₂SCH₃ | 7-F | 4-OCH₃ | H | H |
| 123 | CH₃ | CH₂C₆H₅ | 4-OPO₃H₂ | O | CH₂SO₂CH₃ | 7-F | 4-OCH₃ | H | H |
| 132 | CH₃ | CH₂C₆H₅ | 4-OH | O | CH₂SCH₃ | 7-Pr | 4-OCH₃ | H | H |
| 133 | CH₃ | CH₂C₆H₅ | 4-OH | O | CH₂SOCH₃ | 7-Pr | 4-OCH₃ | H | H |
| 134 | CH₃ | CH₂C₆H₅ | 4-OH | O | CH₂SO₂CH₃ | 7-Pr | 4-OCH₃ | H | H |
| 135 | CH₃ | CH₂C₆H₅ | 4-OH | O | CH₂OCH₃ | 7-Pr | 4-OCH₃ | H | H |
| 136 | CH₃ | CH₂C₆H₅ | 4-OSO₃H | O | CH₂SCH₃ | 7-Pr | 4-OCH₃ | H | H |
| 137 | CH₃ | CH₂C₆H₅ | 4-OCOCH₂CH₂CO₂H | O | CH₂SCH₃ | 7-Pr | 4-OCH₃ | H | H |

TABLE 2-continued
Perferred Compounds of Formula I

|  | $R^1$ | $R^2$ | $R^3$ | X | Y | $Y^1$ | $Y^2$ | $Y^3$ | $Y^4$ |
|---|---|---|---|---|---|---|---|---|---|
| 138 | $CH_3$ | $CH_2C_6H_5$ | 4-$OPO_3H_2$ | O | $CH_2SCH_3$ | 7-Pr | 4-$OCH_3$ | H | H |
| 139 | $CH_3$ | $CH_2C_6H_5$ | 4-$OPO_3H_2$ | O | $CH_2SO_2CH_3$ | 7-Pr | 4-$OCH_3$ | H | H |
| 140 | $CH_3$ | $CH_2C_6H_5$ | 4-OH | O | 5-propyl | 7-$CO_2H$ | 4-$OCH_3$ | H | H |
| 141 | $CH_3$ | $CH_2C_6H_5$ | 4-OH | O | 5-propyl | 7-Cl | 4-$CO_2H$ | H | H |
| 142 | $CH_3$ | $CH_2C_6H_5$ | 4-OH | O | 5-propyl | 7-F | 4-$CO_2H$ | H | H |
| 143 | $CH_3$ | $CH_2C_6H_5$ | 4-OH | O | 5-$CH_2CHOHCH_2OH$ | 7-Cl | 4-$CO_2H$ | H | H |
| 144 | $CH_3$ | $CH_2C_6H_5$ | 4-OH | O | 5-$CH_2CHOHCH_2OH$ | 7-F | 4-$CO_2H$ | H | H |
| 145 | $CH_3$ | $CH_2C_6H_5$ | 4-OH | O | 5-$CH_2CHOHCH_3$ | 7-Cl | 4-$CO_2H$ | H | H |
| 146 | $CH_3$ | $CH_2C_6H_5$ | 4-OH | O | 5-$CH_2CHOHCH_3$ | 7-F | 4-$CO_2H$ | H | H |
| 147 | $CH_3$ | $CH_2C_6H_5$ | 4-OH | O | 5-propyl | 7-$SO_3H$ | 4-$OCH_3$ | H | H |
| 148 | $CH_3$ | $CH_2C_6H_5$ | 4-OH | O | 5-$CH_2CH_2OH$ | 7-Cl | 4-$CO_2H$ | H | H |
| 149 | $CH_3$ | $CH_2C_6H_5$ | 4-OH | O | 5-$C(CH_3)_3$ | 7-Cl | 4-$CO_2H$ | H | H |
| 152 | $CH_3$ | $CH_2$ tetrazol | 4-OH | O | 5-propyl | 7-Cl | 4-$CH_3O$ | H | H |
| 153 | $CH_3$ | $CH_2$ tetrazol | 4-OH | O | 5-propyl | 7-Cl | 4-$CH_3O$ | H | H |
| 154 | $CH_3$ | $CH_2$ tetrazol | 4-OH | O | 5-propyl | H | 4-$CH_3O$ | H | H |
| 157 | $CH_3$ | $CH_2C_6H_5$ | 4-OH | O | H | H | H | H | H |
| 158 | $CH_3$ | $CH_2C_6H_5$ | 4-OAc | O | H | H | H | H | H |
| 161 | $CH(CH_3)_2$ | H | 5-OH | O | H | H | — | — | — |
| 162 | $CH(CH_3)_2$ | H | 4-OH | O | H | H | — | — | — |
| 163 | $CH_3$ | H | 4-OH | O | 5-propyl | 7-Cl | — | — | — |
| 164 | $CH_3$ | $CH_2C_6H_5$ | 4-OH | O | H | 7-Cl | 4-$CH_3O$ | H | H |
| 165 | $CH_3$ | $CH_2C_6H_5$ | 4-OH | O | 5-$C_4H_9$ | 7-Cl | 4-$CH_3O$ | H | H |
| 166 | H | $CH_2C_6H_5$ | 4-OH | O | 5-propyl | 7-Cl | 4-$CH_3O$ | H | H |
| 167 | Propyl | $CH_2C_6H_5$ | 4-OH | O | 5-propyl | 7-Cl | 4-$CH_3O$ | H | H |
| 168 | $CH_3$ | $CH_3CH-C_6H_5$ | 4-OH | O | 5-propyl | 7-Cl | 4-$CH_3O$ | H | H |
| 169 | $CH_3$ | $C_7H_{15}$ | 4-OH | O | 5-propyl | H | — | — | — |
| 170 | $CH_3$ | $CH_2C_6H_5$ | 4-OH | O | 5-propyl | 6-OMe | 4-$CH_3O$ | H | H |
| 171 | $CH_3$ | $CH_2C_6H_5$ | 4-OH | S | 5-propyl | 7-Cl | 4-$CH_3O$ | H | H |
| 172 | $CH_3$ | $C_6H_5$ | 4-OH | O | 5-propyl | 7-Cl | H | H | H |
| 173 | $CH_3$ | $CH_2C_6H_5$ | 4-OH | O | 5-Cl | 7-Cl | 4-$CH_3O$ | H | H |
| 174 | $CH_3$ | $CH_2C_6H_5$ | 4-OH | O | 5-propyl | 7-Cl | 4-Cl | H | H |
| 175 | $CH_3$ | $CH_2C_6H_5$ | 4-OH | O | 5-propyl | 7-Cl | 2-$CH_3O$ | 4-$CH_3O$ | H |
| 178 | $CH_3$ | $CH_2C_6H_5$ | 4-OH | O | 5-Me | 7-Cl | 4-$CH_3O$ | H | H |
| 179 | $CH_3$ | $CH_2C_6H_5$ | 4-OH | O | 5-allyl | 7-Cl | 4-$CH_3O$ | H | H |
| 180 | $CH_3$ | $CH_2C_6H_5$ | 4-OH | O | 5-$(CH_2)_3OH$ | 7-Cl | 4-$CH_3O$ | H | H |
| 181 | $CH_3$ | $CH_2C_6H_5$ | 4-OH | O | 5-$(CH_2)_2CO_2H$ | 7-Cl | 4-$CH_3O$ | H | H |
| 182 | $CH_3$ | $CH_2C_6H_5$ | 4-OH | O | 5-EtO | 7-Cl | 4-$CH_3O$ | H | H |

TABLE 3
More-Preferred Compounds of Formula I

|  | $R^1$ | $R^2$ | $R^3$ | X | Y | $Y^1$ | $Y^2$ | $Y^3$ | $Y^4$ |
|---|---|---|---|---|---|---|---|---|---|
| 8 | $CH_3$ | $C_2H_5$ | 4-OH | O | 5-allyl | H | — | — | — |
| 14 | $CH_3$ | $CH_2$-4-pyridyl | 4-OH | O | 5-propyl | H | H | H | H |
| 15 | $CH_3$ | $CH_2C_6H_5$ | 5-OH | O | 6-OH | H | H | H | H |
| 16 | $CH_3$ | $CH_2C_6H_5$ | 4-OH | O | 5-Propyl | H | 4-OH | H | H |
| 17 | $CH_3$ | $CH_2C_6H_5$ | 4-OH | O | 5-Propyl | H | 4-$OCH_3$ | H | H |
| 33 | $CH_3$ | $CH_2C_6H_5$ | 4-OH | O | 5-propyl | H | 4-Cl | H | H |
| 38 | $CH_3$ | $CH_2C_6H_5$ | 4-OH | O | 5-propyl | 7-F | 4-$OCH_3$ | H | H |
| 73 | $CH_3$ | $CH_2C_6H_5$ | 4-OH | O | 5-propyl | 7-Cl | 4-$OCH_3$ | 3-CHO | H |
| 74 | $CH_3$ | $CH_2C_6H_5$ | 4-OH | O | 5-propyl | 7-Cl | 4-Br | H | H |
| 75 | $CH_3$ | $CH_2C_6H_5$ | 4-OH | O | 5-propyl | 7-Cl | H | H | H |
| 76 | $CH_3$ | $CH_2C_6H_5$ | 5-OH | O | 4-propyl | 7-Cl | 4-F | H | H |
| 77 | $CH_3$ | $CH_2C_6H_5$ | 4-OAc | O | 5-propyl | 7-Cl | 4-OAc | H | H |
| 78 | $CH_3$ | $CH_2C_6H_5$ | 4-OAc | O | 5-propyl | H | 4-OH | H | H |
| 79 | $CH_3$ | $CH_2C_6H_5$ | 5-OH | O | 4-propyl | H | 4-OH | H | H |
| 80 | $CH_3$ | $CH_2C_6H_5$ | 5-OH | O | H | H | 4-OH | H | H |
| 81 | $CH_3$ | $CH_2C_6H_5$ | 7-OH | O | H | H | 4-$OCH_3$ | H | H |
| 82 | $CH_3$ | $CH_2C_6H_5$ | 4-Oallyl | O | H | H | 4-$OCH_3$ | H | H |
| 84 | $CH_3$ | $CH_2C_6H_5$ | 4-OAc | O | 5-propyl | 7-Cl | 4-$OCH_3$ | H | H |
| 85 | $CH_3$ | $CH_2C_6H_5$ | 4-OAc | O | 5-propyl | 7-F | 4-$OCH_3$ | H | H |
| 86 | $CH_3$ | $CH_2C_6H_5$ | 4-$OCO_2CHClCH_3$ | O | 5-propyl | 7-Cl | 4-$OCH_3$ | H | H |
| 87 | $CH_3$ | $CH_2C_6H_5$ | 4-$OCO_2CH_3$ | O | 5-propyl | 7-F | 4-$OCH_3$ | H | H |
| 88 | $CH_3$ | $CH_2C_6H_5$ | 4-$OCO_2CH_3$ | O | 5-propyl | 7-Cl | 4-$OCH_3$ | H | H |
| 89 | $CH_3$ | $CH_2C_6H_5$ | 4-OH | O | 5-propyl | 7-Br | 4-$OCH_3$ | H | H |
| 90 | $CH_3$ | $CH_2C_6H_5$ | 4-OH | O | 5-propyl | 7-Cl | 4-$OCH_3$ | H | H |
| 91 | $CH_3$ | $CH_2C_6H_5$ | 4-OH | O | 5-allyl | H | 4-$OCH_3$ | H | H |
| 92 | $CH_3$ | $CH_2C_6H_5$ | 4-OH | O | H | H | 4-$OCH_3$ | H | H |
| 93 | $CH_3$ | $CH_2C_6H_5$ | 4-OH | O | 7-propyl | H | 4-$OCH_3$ | H | H |
| 94 | $CH_3$ | $CH_2C_6H_5$ | 4-OH | O | 5-propyl | 7-$CH_3$ | 4-$OCH_3$ | H | H |
| 95 | $CH_3$ | $CH_2C_6H_5$ | 4-OH | O | 5-propyl | 7-Pr | 4-$OCH_3$ | H | H |
| 96 | $CH_3$ | $CH_2C_6H_5$ | 4-OH | O | 5-Cl | 7-Pr | 4-$OCH_3$ | H | H |
| 97 | $CH_3$ | $CH_2C_6H_5$ | 4-$OPO_3H_2$ | O | 5-propyl | 7-Cl | 4-$OCH_3$ | H | H |
| 98 | $CH_3$ | $CH_2C_6H_5$ | 4-$OCOCH_2CH_2CO_2H$ | O | 5-propyl | 7-F | 4-$OCH_3$ | H | H |
| 99 | $CH_3$ | $CH_2C_6H_5$ | 4-$OCOCH_2CH_2CO_2H$ | O | 5-propyl | 7-Cl | 4-$OCH_3$ | H | H |
| 100 | $CH_3$ | $CH_2C_6H_5$ | 5-OAc | O | 4-propyl | H | 4-$OCH_3$ | H | H |
| 101 | $CH_3$ | $CH_2C_6H_5$ | 5-$OCO_2CH_3$ | O | 4-propyl | H | 4-$OCH_3$ | H | H |
| 102 | $CH_3$ | $CH_2C_6H_5$ | 5-OH | O | 4-propyl | H | 4-$OCH_3$ | H | H |

TABLE 3-continued

More-Preferred Compounds of Formula I

| | $R^1$ | $R^2$ | $R^3$ | X | Y | $Y^1$ | $Y^2$ | $Y^3$ | $Y^4$ |
|---|---|---|---|---|---|---|---|---|---|
| 103 | $CH_3$ | $CH_2C_6H_5$ | 4-OAc | O | 5-propyl | 7-Cl | 4-OCH$_2$CO$_2$Et | H | H |
| 104 | $CH_3$ | $CH_2C_6H_5$ | 4-OCH$_2$CO$_2$Et | O | 5-propyl | 7-Cl | 4-OCH$_2$CO$_2$ Et | H | H |
| 105 | $CH_3$ | $CH_2C_6H_5$ | 4-OH | O | 5-propyl | 7-Cl | 4-OCH$_2$CO$_2$H | H | H |
| 109 | $CH_3$ | $CH_2C_6H_5$ | 4-OH | O | 5-propyl | 7-Cl | 4-OH | H | H |
| 110 | $CH_3$ | $CH_2CH_2C_6H_5$ | 4-OAc | O | H | H | 4-OCH$_3$ | H | H |
| 111 | $CH_3$ | $CH_2CH_2C_6H_5$ | 4-OH | O | H | H | 4-OCH$_3$ | H | H |
| 112 | $CH_3$ | $CH_2CH_2C_6H_5$ | 4-OH | O | 5-propyl | 7-Cl | 4-OCH$_3$ | H | H |
| 113 | $CH_3$ | $CH_2CH_2C_6H_5$ | 4-OH | O | 5-propyl | H | 4-OCH$_3$ | H | H |
| 114 | $CH_3$ | $CH_2C_6H_5$ | 4-OSO$_3$H | O | 5-propyl | 7-Cl | 4-OCH$_3$ | H | H |
| 157 | $CH_3$ | $CH_2C_6H_5$ | 4-OH | O | H | H | H | H | H |
| 165 | $CH_3$ | $CH_2C_6H_5$ | 4-OH | O | 5-C$_4$H$_9$ | 7-Cl | 4-CH$_3$O | H | H |
| 166 | H | $CH_2C_6H_5$ | 4-OH | O | 5-propyl | 7-Cl | 4-CH$_3$O | H | H |
| 167 | Propyl | $CH_2C_6H_5$ | 4-OH | O | 5-propyl | 7-Cl | 4-CH$_3$O | H | H |
| 168 | $CH_3$ | CH$_3$CH—C$_6$H$_5$ | 4-OH | O | 5-propyl | 7-Cl | 4-CH$_3$O | H | H |
| 169 | $CH_3$ | C$_7$H$_{15}$ | 4-OH | O | 5-propyl | H | — | — | — |
| 170 | $CH_3$ | $CH_2C_6H_5$ | 4-OH | O | 5-propyl | 6-OMe | 4-CH$_3$O | H | H |
| 171 | $CH_3$ | $CH_2C_6H_5$ | 4-OH | S | 5-propyl | 7-Cl | 4-CH$_3$O | H | H |
| 172 | $CH_3$ | C$_6$H$_5$ | 4-OH | O | 5-propyl | 7-Cl | H | H | H |
| 174 | $CH_3$ | $CH_2C_6H_5$ | 4-OH | O | 5-propyl | 7-Cl | 4-Cl | H | H |
| 175 | $CH_3$ | $CH_2C_6H_5$ | 4-OH | O | 5-propyl | 7-Cl | 2-CH$_3$O | 4-CH$_3$O | H |
| 178 | $CH_3$ | $CH_2C_6H_5$ | 4-OH | O | 5-Me | 7-Cl | 4-CH$_3$O | H | H |
| 179 | $CH_3$ | $CH_2C_6H_5$ | 4-OH | O | 5-allyl | 7-Cl | 4-CH$_3$O | H | H |
| 180 | $CH_3$ | $CH_2C_6H_5$ | 4-OH | O | 5-(CH$_2$)$_3$OH | 7-Cl | 4-CH$_3$O | H | H |
| 181 | $CH_3$ | $CH_2C_6H_5$ | 4-OH | O | 5-(CH$_2$)$_2$CO$_2$H | 7-Cl | 4-CH$_3$O | H | H |
| 182 | $CH_3$ | $CH_2C_6H_5$ | 4-OH | O | 5-EtO | 7-Cl | 4-CH$_3$O | H | H |

TABLE 4

Most-Preferred Compounds of Formula I

| | $R^1$ | $R^2$ | $R^3$ | X | Y | $Y^1$ | $Y^2$ | $Y^3$ | $Y^4$ |
|---|---|---|---|---|---|---|---|---|---|
| 14 | $CH_3$ | CH$_2$ 4-pyridyl | 4-OH | O | 5-propyl | H | H | H | H |
| 16 | $CH_3$ | $CH_2C_6H_5$ | 4-OH | O | 5-propyl | H | 4-OH | H | H |
| 17 | $CH_3$ | $CH_2C_6H_5$ | 4-OH | O | 5-propyl | H | 4-OCH$_3$ | H | H |
| 38 | $CH_3$ | $CH_2C_6H_5$ | 4-OH | O | 5-propyl | 7-F | 4-OCH$_3$ | H | H |
| 77 | $CH_3$ | $CH_2C_6H_5$ | 4-OAc | O | 5-propyl | 7-Cl | 4-OAc | H | H |
| 78 | $CH_3$ | $CH_2C_6H_5$ | 4-OAc | O | 5-propyl | H | 4-OH | H | H |
| 84 | $CH_3$ | $CH_2C_6H_5$ | 4-OAc | O | 5-propyl | 7-Cl | 4-OCH$_3$ | H | H |
| 85 | $CH_3$ | $CH_2C_6H_5$ | 4-OAc | O | 5-propyl | 7-F | 4-OCH$_3$ | H | H |
| 86 | $CH_3$ | $CH_2C_6H_5$ | 4-OCO$_2$CHClCH$_3$ | O | 5-propyl | 7-Cl | 4-OCH$_3$ | H | H |
| 87 | $CH_3$ | $CH_2C_6H_5$ | 4-OCO$_2$CH$_3$ | O | 5-propyl | 7-F | 4-OCH$_3$ | H | H |
| 88 | $CH_3$ | $CH_2C_6H_5$ | 4-OCO$_2$CH$_3$ | O | 5-propyl | 7-Cl | 4-OCH$_3$ | H | H |
| 90 | $CH_3$ | $CH_2C_6H_5$ | 4-OH | O | 5-propyl | 7-Cl | 4-OCH$_3$ | H | H |
| 94 | $CH_3$ | $CH_2C_6H_5$ | 4-OH | O | 5-propyl | 7-CH$_3$ | 4-OCH$_3$ | H | H |
| 95 | $CH_3$ | $CH_2C_6H_5$ | 4-OH | O | 5-propyl | 7-Pr | 4-OCH$_3$ | H | H |
| 97 | $CH_3$ | $CH_2C_6H_5$ | 4-OPO$_3$H$_2$ | O | 5-propyl | 7-Cl | 4-OCH$_3$ | H | H |
| 98 | $CH_3$ | $CH_2C_6H_5$ | 4-OCOCH$_2$CH$_2$CO$_2$H | O | 5-propyl | 7-F | 4-OCH$_3$ | H | H |
| 99 | $CH_3$ | $CH_2C_6H_5$ | 4-OCOCH$_2$CH$_2$CO$_2$H | O | 5-propyl | 7-Cl | 4-OH$_3$ | H | H |
| 100 | $CH_3$ | $CH_2C_6H_5$ | 5-OAc | O | 4-propyl | H | 4-OCH$_3$ | H | H |
| 101 | $CH_3$ | $CH_2C_6H_5$ | 5-OCO$_2$CH$_3$ | O | 4-propyl | H | 4-OCH$_3$ | H | H |
| 102 | $CH_3$ | $CH_2C_6H_5$ | 5-OH | O | 4-propyl | H | 4-OCH$_3$ | H | H |
| 103 | $CH_3$ | $CH_2C_6H_5$ | 4-OAc | O | 5-propyl | 7-Cl | 4-OCH$_2$CO$_2$Et | H | H |
| 105 | $CH_3$ | $CH_2C_6H_5$ | 4-OH | O | 5-propyl | 7-Cl | 4-OCH$_2$CO$_2$H | H | H |
| 109 | $CH_3$ | $CH_2C_6H_5$ | 4-OH | O | 5-propyl | 7-Cl | 4-OH | H | H |
| 112 | $CH_3$ | $CH_2CH_2C_6H_5$ | 4-OH | O | 5-propyl | 7-Cl | 4-OCH$_3$ | H | H |
| 113 | $CH_3$ | $CH_2CH_2C_6H_5$ | 4-OH | O | 5-propyl | H | 4-OCH$_3$ | H | H |
| 114 | $CH_3$ | $CH_2C_6H_5$ | 4-OSO$_3$H | O | 5-propyl | 7-Cl | 4-OCH$_3$ | H | H |
| 157 | $CH_3$ | $CH_2C_6H_5$ | 4-OH | O | H | H | H | H | H |
| 165 | $CH_3$ | $CH_2C_6H_5$ | 4-OH | O | 5-C$_4$H$_9$ | 7-Cl | 4-CH$_3$O | H | H |
| 166 | H | $CH_2C_6H_5$ | 4-OH | O | 5-propyl | 7-Cl | 4-CH$_3$O | H | H |
| 167 | Propyl | $CH_2C_6H_5$ | 4-OH | O | 5-propyl | 7-Cl | 4-CH$_3$O | H | H |
| 168 | $CH_3$ | CH$_3$CH—C$_6$H$_5$ | 4-OH | O | 5-propyl | 7-Cl | 4-CH$_3$O | H | H |
| 169 | $CH_3$ | C$_7$H$_{15}$ | 4-OH | O | 5-propyl | H | — | — | — |
| 171 | $CH_3$ | $CH_2C_6H_5$ | 4-OH | S | 5-propyl | 7-Cl | 4-CH$_3$O | H | H |
| 172 | $CH_3$ | C$_6$H$_5$ | 4-OH | O | 5-propyl | 7-Cl | H | H | H |
| 174 | $CH_3$ | $CH_2C_6H_5$ | 4-OH | O | 5-propyl | 7-Cl | 4-Cl | H | H |
| 175 | $CH_3$ | $CH_2C_6H_5$ | 4-OH | O | 5-propyl | 7-Cl | 2-CH$_3$O | 4-CH$_3$O | H |
| 178 | $CH_3$ | $CH_2C_6H_5$ | 4-OH | O | 5-Me | 7-Cl | 4-CH$_3$O | H | H |
| 179 | $CH_3$ | $CH_2C_6H_5$ | 4-OH | O | 5-allyl | 7-Cl | 4-CH$_3$O | H | H |
| 180 | $CH_3$ | $CH_2C_6H_5$ | 4-OH | O | 5-(CH$_2$)$_3$OH | 7-Cl | 4-CH$_3$O | H | H |
| 181 | $CH_3$ | $CH_2C_6H_5$ | 4-OH | O | 5-(CH$_2$)$_2$CO$_2$H | 7-Cl | 4-CH$_3$O | H | H |
| 182 | $CH_3$ | $CH_2C_6H_5$ | 4-OH | O | 5-EtO | 7-Cl | 4-CH$_3$O | H | H |

The following reaction schemes illustrate the preparation of compounds of the present invention:

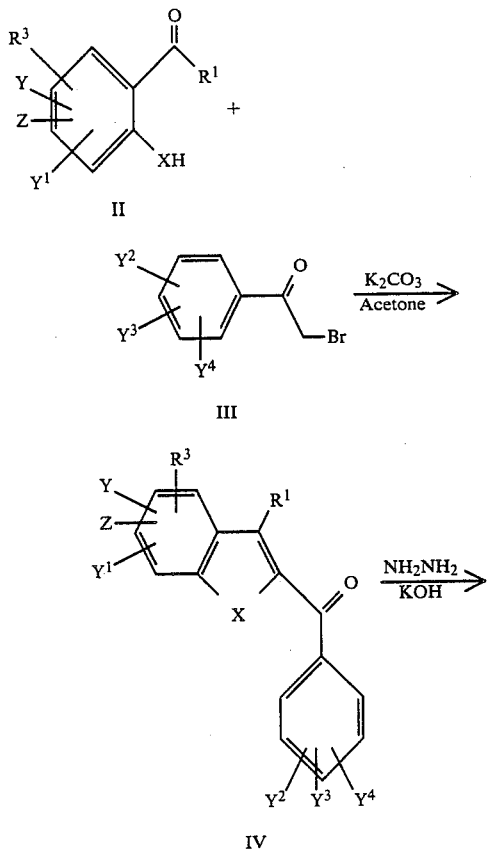

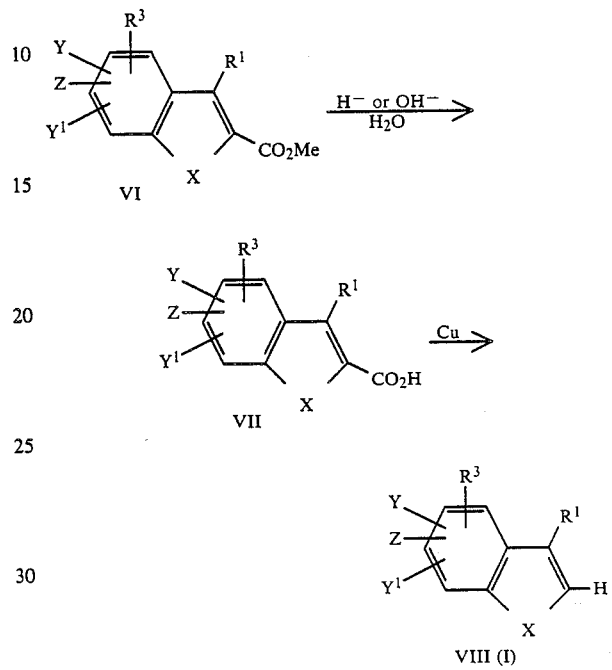

A suitable acetophenone (II) wherein Y is as defined above is reacted with a substituted phenacyl bromide (III) wherein Y is as defined above at a temperature ranging from room temperature to about 150° C. in an inert solvent (preferably at reflux in acetone) in the presence of a base (for example, an alkali metal hydroxide or carbonate) to give the corresponding benzoyl benzofuran derivative (IV). The compound of the formula IV is then reduced to give the compound of Formula I. For example, subsequent treatment of IV with hydrazine and a strong base at a temperature of about 150° to 210° C. preferably using the Huang Minlon modification of Wolff Kishner conditions (J. Am. Chem. Soc. 68, 2487 (1946)) yields the desired benzyl benzofuran derivative I. Alternatively, compound IV can be reduced to compound I using the zinc amalgam and a strong acid (preferably hydrochloric acid). See, for example, Ber. 46, 1837 (1913). Alternatively, compound IV can be reduced to compound I using a mixture of lithium aluminum hydride and aluminum chloride in ether or tetrahydrofuran as solvent at a temperature range varying from 0° C. to 65° C.

According to the method of Scheme II, hydrolysis of an appropriate compound of the formula VI, wherein Y is as defined above, with a strong acid and/or a strong base in water, or a mixture of water and a water soluble solvent, at a temperature ranging from room temperature to reflux (preferably, reflux) yeilds the corresponding acid of formula VII. Compounds of the formula VI are disclosed in U.S. Ser. No. 661,645, filed Oct. 17, 1984 , the disclosure of which is hereby incorporated herein by reference. The acid of formula VII is then decarboxylated to yield the corresponding benzofuran derivative of the formula VIII. This may be done by heating the acid in quinoline in the presence of copper. It can also be done by heating at reflux compound VII with a strong acid such as hydrochloric acid in a two-phase system made up of toluene and agueous acid. Benzene or xylene or other aromatic hydrocarbons can be substituted for toluene.

SCHEME III

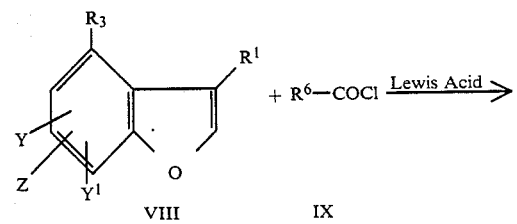

-continued
SCHEME III

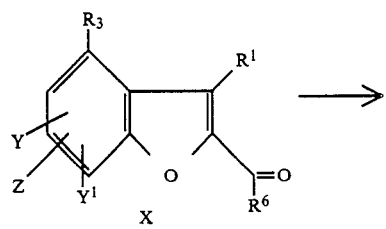

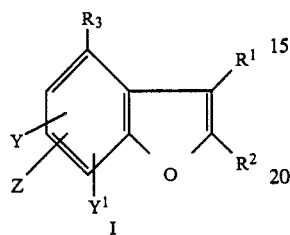

I wherein $R^6$ is $C_1$ to $C_5$ alkyl, $(CH_2)_{n-1}Het$, or $-(CH_2)_{n-1}-PhY_2Y_3Y_4$ Following Scheme III, Compound VIII, which is unsubstituted in position 2, can be reacted with an acid halide IX in the presence of a Lewis acid. Preferably aluminum chloride, to yield the 2-acyl derivative X. This reaction is best carried out in a solvent such as methylene chloride or ethylene dichloride at a temperature ranging from 0° to 25° C. The compound of the Formula X is then reduced to give the compound of Formula I. For example, subseguent treatment of X with hydrazine and a strong base at a temperature of about 150° to 210° C. using the Huang-Minlon modification of Wolff-Kishner conditions (J. Am. Chem. Soc. 68, 2487 (1946)) yields the desired alkyl benzofuran derivative I. Alternatively, compound X can be reduced to compound I using the zinc amalgam and a strong acid (preferably hydrochloric acid). See, for example, Bev., 46, 1837 (1913).

Alternatively, compound X can be reduced to compound I using a mixture of lithium aluminum hydride and aluminum chloride in ether or tetrahydrofuran as solvent at a temperature range varying from 0° to 65° C.

SCHEME IV

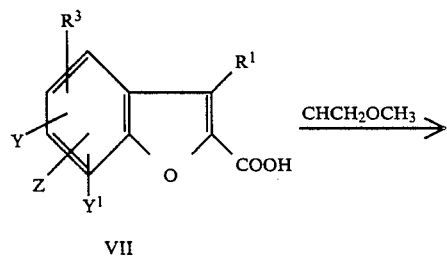

VII

-continued
SCHEME IV

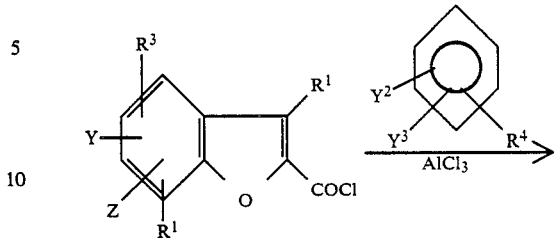

XI

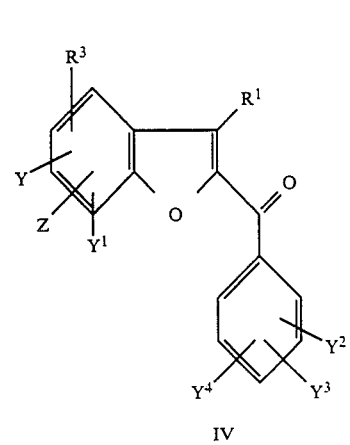

IV

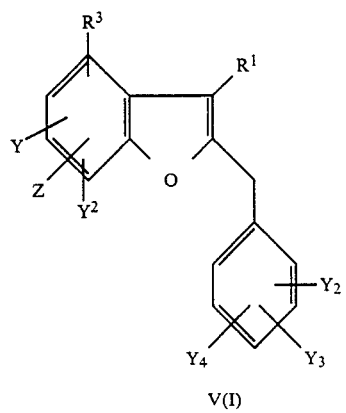

V(I)

Scheme IV describes another synthesis of compounds of Formula I. A carboxylic acid derivative VII is reacted with dichloromethyl methyl ether at reflux for 30 minutes to 2 hours to yield the corresponding acid chloride XI. This acid choride XI can then be reacted with a suitably substituted aromatic derivative such as anisole, toluene, or the like to yield the desired 2 benzoyl derivative IV. The Friedel-Crafts aroylation reaction is best carried out in an inert solvent such as methylene chloride or ethylene dichloride and is catalyzed very efficiently by a Lewis acid, preferably aluminum chloride. The 2-benzoyl derivative IV is then reduced to the 2-benzyl derivative V. For example, subsequent treatment of IV with hydrazine and a strong base at a temperature of about 150° to 210° C. preferably using the Huang Minlon modification of Wolff-Kishner conditions (J. Am. Chem. Soc. 68, 2487 (1946)) yields the desired benzyl benzofuran derivative V. Alternatively, compound IV can be reduced to compound V using the zinc amalgam and a strong acid (preferably hydrochloric acid). See, for example, Ber. 46, 1837 (1913). Alternatively, compound IV can be reduced to compound V using a mixture of lithium aluminum hydride and aluminum chloride in ether or tetrahydrofuran as solvent at a temperature range varying from 0° C. to 65° C.

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

The compounds of Formula I may be tested using one or more of the following assays to determine their mammalian leukotriene biosynthesis inhibiting activity and other relevant activities.

RBL 1 5 Lipoxygenase

Rat basophilic leukemia (RBL-1) cells are sonicated and centrifuged at 125000 ×g. The resulting supernatant fraction is incubated with arachidonic acid (labelled with $^{14}C$) to convert a portion of it to $^{14}C$-5(S) hydroxyicosatetraenoic acid (5-HETE). Compounds being evaluated as inhibitors of 5-Lipoxygenase are added prior to the addition of arachidonic acid. 5-HETE is isolated by extraction and paper chromatogrphy, and quantitated by determining the amount of radioactivity (cpm) associated with 5-HETE.

Reference: Egan, R. W.; Tischler, A. M.; Baptista, E. H.; Ham, E. A.; Soderman, D. D.; and Gale, P. H.; *Advances in Prostaglandin, Thromboxane* and *Leukotriene Research*, 11, 151,(1983), (Samuelsson, B.; Ramwell, P. W.; and Paoletti, R.; (eds.), Raven Press, N.Y.

Mouse Macrophase Assay

Mouse peritoneal macrophages are treated sequentially with arachidonic acid (labelled with tritium); the compound being evaluated as an inhibitor, and a stimulator (zymosan). Metabolites derived from arachidonic acid ($PGE_2$, 6-keto $PG$-$F_{1a}$ and leukotriene $C_4$) are separated from the incubation medium by extraction and chromatography, and then quantitated by determining the amount of radioactivity (cpm) associated with each of them. Inhibitors cause a reduction in the amount of radioactivity (cpm) associated with a given metabolite. (This protocol is identical to that described in the reference except that the radioactivity herein associated with the $LTC_4$ is determined by counting an aliquot of the final aqueous solution directly rather than chromatographing it first.)

Reference: Humes, J. L. et al., *J. Biol. Chem.*, 257, 1591–4,(1982).

Rat Polymorphonuclear Leukocyte (P.M.N.) Assay

Rats under ether anesthesia are injected (intraperitoneally) with 8 ml of a suspension of sodium caseinate (6 grams in about 50 ml water). After 15 to 24 hours the rats are sacrificed ($CO_2$) and the cells from the peritoneal cavity are recovered by lavage with 20 ml of buffer (Eagles Minimal Essential Medium containing 30 mM HERPES adjusted to pH 7.4 with NaOH). The cells are pelleted (350 ×g, 5 min.), resuspended in buffer with vigorous shaking, filtered through lens paper, recentrifuged and finally suspended in buffer at a concentration of 10 cells/ml. A 500 μl aliquot of the suspension (PMN) and test compound are preincubated for 2 minutes at 37° C., followed by the addition of 10 μM A 23187 calcium ionophore (Calbiochem). The suspension is stirred for an additional 4 minutes then bioassayed for $LTB_4$ content by adding an aliquot to a second 500 μl portion of the PMN at 37° C. The $LTB_4$ produced in the first incubation causes aggregation of the second PMN, is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Antigen Challenge 'in vitro' Assay

Male guinea pigs weighing 300–350 g are sensitized by injecting (intraperitoneally) 0.5 ml of a suspension containing 0.4 mg of egg albumin (Ovalbumin, Grade V, Sigma Chemical Co.) and 4.0 g aluminum hydroxide in 19.6 ml of saline. Two weeks are permitted for sensitization to occur.

Three sensitized guinea pigs are stunned and exanguinated. The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No.7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified[1] Krebs-Henseleit buffer solution gassed with 95% $O_2$ and 5% $CO_2$ at 37° C. Mepyramine (0.55 μg/ml) and indomethacin (2.67 μg/ml) are added to the buffer to avoid the contribution of histamine receptors and cyclooxygenase products to the contraction. To record responses one end of the tracheal chain is attached to a Gould-Statham UC-2 force displacement transducer which is connected to a Beckman Type R-dynograph. The preparations are allowed to equilibrate for one hour during which time the tissues are automatically washed (10 ml volume displacement) every 6 minutes.

[1]modified Krebs solution in grams/liter and (mM): NaCl—6.87 (120); glucose—2.1 (11); NaHCO$_3$—2.1 (25); KCl—0.32 (4.72); CaCl$_2$—0.28 (2.5); MgSO$_4$.7H$_2$O—0.11 (0.5); KH$_2$PO$_4$—0.16 (1.2); pH at bathing solution=7.35±0.05.

After the equilibration period the tissues are primed with methacholine (3 μg/ml; 1.5×10$^{-5}$M), washed and allowed to recover to baseline. The tissues are treated again with a second dose of methacholine, washed, allowed to return to baseline and washed for an additional hour.

Two chains are used as a control. These are incubated in a concentration of egg albumin sufficient to induce an average contraction of 50–80% of the methacholine response.

Each compound to be tested is added to two their baths (at a final concentration in each bath of 10 μg/ml) 15 minutes prior to challenging the fresh chains with egg albumin.

The response of the challenged tissue is expressed as a percentage of the methacholine maximum. The percentage inhibition for each compound is then calculated. Compounds which at 10 μg/ml (final concentration) inhibit the egg albumin response by 50% or more are retested at a lower concentration.

Asthmatic Rat Assay

Rats are obtained from an inbred line of asthmatic rats. Both female and male rats from 200 to 300 g are used.

Egg albumin (EA), grade V, crystallized and lyophilized, is obtained from Sigma Chemical Co., St. Louis. *Bordetella pertussis* vaccine, containing $30 \times 10^9$ killed bacteria per ml is obtained from the Institute Armand-Frappier, Laval des Rapides, Quebec. Aluminum hydroxide is obtained from the Regis Chemical Company, Chicago.

The challenge and subseguent respiratory recordings are carried out in a clear plastic box with internal dimensions $10 \times 6 \times 4$ inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 ml of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 ml of a suspension containing 1 mg EA and 200 mg aluminum hydroxide in saline. Simultaneously, they receive an injection (intra peritoneally) of 0.5 ml of *B. pertussis* vaccine. They are used between days 14 and 18 postsensitization. In order to eliminate the serotonin component of the response, rats are pretreated intravenously 5 minutes prior to aerosol challenge with 30 gm/kg methylserzide. Rats are then exposed to an aerosol of 3% EA in saline for exactly 1 minute, then their respiratory profiles are recorded for a further 25 to 30 minutes. The duration of continuous dyspnoea is measured from the respiratory recordings.

Compounds are generally administered either intraperitoneally 1 hour prior to challenge or orally 1 and ½ hours prior to challenge. They are either dissolved in dimethylsulfoxide or suspended in 0.1% methocel and 0.5% Tween 80. The volume injected is 2 ml/kg (intraperitoneally) or 10 ml/kg (orally). Prior to oral treatment rats are starved overnight. Their activity is determined in terms of their ability to decrease the duration of symptoms of dyspnoea in comparison with a group of vehicle-treated controls. Usually, a compound is evaluated at a series of doses and an $ED_{50}$ is determined. This is defined as the dose (mg/kg) which would inhibit the duration of symptoms by 50%.

PAF-Induced Hyperalgesia Assay

Female Sprague-Dawley rats, 35 to 40 g are fasted overnight. Platelet activating factor, PAF, (L-lecithin B-acetyl O-alkyl) 1 µg/0.1 ml is given by subplantar injection in the rat paw. The compounds to be evaluated are homogenized in Aqueous Vehicle (0.9% benzyl alcohol, 0.5% Tween 80 and 0.4% methylcellulose) and administered orally in a volume of 0.1 ml, 30 minutes prior to PAF.

Animals are tested 1, 2, 3 and 4 hours after PAF administration. The vocalization threshold, defined as the pressure (mmHg) needed to evoke a squeak response, was recorded for both the injected and contralateral paw. No animal is subjected to pressure greater than 60 mmHg. Hyperalgesia is defined as a decrease in vocalization threshold as compared to a normal paw. Percent inhibition of hyperalgesia is calculated as the proportion of animals with vocalization thresholds greater than 200% of controls.

Brewer's Yeast Hyperalgesia Assay

The standard method [Winter, C. A. et al., J. Pharm. Exp. Ther. 150, 165–171 (1965)] for yeast hyperalgesia is used. Female Spraque-Dawley rates, 35–40 g are fasted overnight. A 5% solution (volume 0.1 ml) of Brewer's yeast is injected into the rat paw. The compound is homogenized in aqueous vehicle and given orally 2 hours after yeast. Vocalization thresholds are recorded 1 hour after drug (3 hours after yeast). Percent inhibition of hyperalgesia is determined by the proportion of animals with vocalization thresholds greater than 25 mmHg.

The compounds of the Formula I have unexpected activity as inhibitors of the mammalian biosynthesis of leukotriene $B_4$, as well as leukotrienes $C_4$, $D_4$, $E_4$ and $F_4$, the active elements of the slow reacting substance of anaphylaxis (SRS-A). The compounds of Formula I act as inhibitors of the mammalian 5-lipoxygenase enzyme system of the arachidonic acid cascade. This inhibition of the mammalian biosynthesis of leukotrienes indicates that the compositions are useful to treat, prevent or ameliorate, in mammals and especially in humans (1) pulmonary conditions including diseases such as asthma, (2) allergies and allergic reactions such as allergic rhinitis, contact dermatitis, allergic conjunctivitis and the like, (3) inflammation such as arthritis, (4) pain, (5) skin conditions such as psoriasis and the like, and (6) cardiovascular conditions such as angina and the like, and that the compounds are cytoprotective agents.

Thus, the compounds of the present invention may also be used to treat or prevent mammalian (especially, human) disease states such as erosive gastritis; erosive esophagitis; inflammatory bowel disease; ethanol induced hemorrhagic erosions; hepatic ischemia; noxious agent induced damage or necrosis of hepatic, pancreatic, renal, or myocardial tissue, liver parenchymal damage caused by hepatoxic agents such as $CCl_4$ and D galactosamine; ischemic renal failure; disease-induced hepatic damage; bile salt induced pancreatic or gastric damage; trauma- or stress-induced cell damage; and glycerol-induced renal failure.

The cytoprotective activity of a compound may be observed in both animal and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) does with 1.0 ml absolute ethanol. Fifteen to thirty minutes prior to ethanol administration, groups of rats each receive either an agueous vehicle (aqueous methylcellulose 5% wt.) or the test compound at various doses perorally. One hour later, the animals are sacrificed and stomach mucosa are examined for resulting lesions.

B. Indomethacin-Induced Ulcer Assay

Indomethacin, 10 mg/kg p.o., is used to induce ulcers in 24 hour fasted S. K. rats. Fifteen minutes prior to indomethacin administration, groups of rats each receive either an aqueous vehicle (5% by weight methylcellulose) or the test compound at various doses perorally. Four hours later the animals are sacrifices and stomach mucosa are examined for resulting ulcers.

The magnitude of a prophylactic or therapeutic dose of a compound of formula I will, of course, vary with the nature of the severity of the condition to be treated and with the particular compound of formula I and its route of administration. When a compound of formula I is used in a pharmaceutical composition, the effective concentration in the composition will vary as required by the mode of administration, dosage form and pharmocological effect and level desired. In general, the daily dose range for anti-asthmatic, anti-allergic or anti inflammatory use and, generally, uses other than cytoprotection lies within the range of from about 0.01 mg to about 100 mg per kg body weight of a mammal. This dosage may be administered in a single or divided individual doses. More or less of the general daily dosage may be necessary depending upon the individual needs of the patient.

The exact amount of a compound of the Formula I to be used as a cytoprotective agent will depend on, inter alia, whether it is being administered to heal damaged cells or to avoid future damage, on the nature of the damaged cells or to avoid future damage, on the nature of the damaged cells (e.g., gastro intestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID (for example, in a combination dosage form). Preferably itis administered prior to or simultaneous with the NSAID.

The effective daily dosage level for compounds of Formulae I inducing cytoprotection in mammals, especially humans, will generally range from about 0.002 mg/kg to about 100 mg/kg, preferably from about 0.02 mg/kg to about 30 mg/kg. The dosage may be administered in single or divided doses.

Any suitable route of administration may be employed for providing a mammal, especially a human, with an effective dosage of a leukotriene antagonist. For example, oral, rectal, transdermal parenteral, intramuscular, intravenous and the like may be employed. Dosage forms include tablets, troches, dispersions, suspensions, solutions, capsules and the like.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 $\mu$g to about 200 $\mu$g, administered as needed.

For treating allergies or allergic reactions, such as allergic conjunctivitis, allergic rhinitis and the like, the Formula I compound may be administered by any conventional mode, e.g., orally, parenterally, topically, subcutaneously, by inhalation and the like. The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight active ingredient (Formula I compound) may vary from about 001 to about 10%.

For treating inflammation the mode of administration may be oral, parenteral, by suppository and the like. The various dosage forms are the same as those described above.

For treating skin diseases such as psoriasis, atopic dermatitis and the like, oral, topical or parenteral administration is useful. For topical application to the diseased area salves, patches, controlled release patches, emulsions, etc., are convenient dosage forms.

For use as an analgesic, i.e., for treating pain, any suitable mode of administration may be used, e.g., oral, parenteral, by insufflation, by suppository and the like.

Fo treating cardiovascular conditions such as angina pectoris, etc., any suitable mode of administration, e.g. oral, parenteral, topical, insufflation, etc. and dosage form e.g. pills, liguid formulations, controlled release capsules, controlled release skin patches, etc. may be used.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethlenediamine, glucosamine, methylglucamine, theobromine, purines, piperazine, piperidine, N-ethylpiperidine, polyamine resins and the like. For a useful discussion of pharmaceutical salts see S. M. Berge et al., Journal of Pharmaceutical Sciences, 66, 119 (1977), the disclosure of which is hereby incorporated herein by reference.

The compositions include compositions suitable for oral, rectal, ophthalmic, pummonary, nasal, dermal, topical or parenteral (including subcutaneous, intramuscular and intravenous) administration, although the most suitable route in any given case will depend on the nature an severity of the conditions being treated and on the nature of the active ingredient. They may be conveniently presented in unit dosage form and prepared by any of the methods well known in the art of pharmacy.

For use where a composition for intravenous administration is employed, a suitable dosage range for antiasthmatic, anti-inflammatory or anti-allergic use and, generally, uses other than cytoprotection is from about 0.01 mg to about 20 mg (preferably from about 0.1 mg to about 10 mg) of a compound of Formula I per kg of body weight per day and for cytoprotective use from about 0.002 mg to about 100 mg (preferably from about 0.02 mg to about 30 mg and more preferably from about 0.1 mg to about 10 mg) of a compound of Formula I of body weight per day. In the case where an oral composition is employed, a suitable dosage range for antiasthmatic, anti-inflammatory or anti-allergic use and, generally, uses other than cytoprotection is from about 1 to about 100 of a compound of Formula I per kg of body weight per day, preferably from about 5 mg to about 40 mg per kg and for cytoprot-ective use from about 0.01 mg to about 100 mg (preferably from about 0.1 mg to about 30 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition form inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene antagonists of Formula I can be combined as the active ingredient in intimate admixture with a pharmaceutical carrier according to conventional pharmaceutical compounding technigues and using conventional ingredients, e.g. diluents, carriers, etc. The carrier may take a wide variety of forms depending on the form of preparation desired form administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liguid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets and capsules represent the most advantageous oral dosage unit form, in which case solid pharmaceutical carriers are obviousy employed. If desired, tablets may be sugar coated or enteric coated by standard technigues.

In addition to the common dosage forms set above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are incorporated herein by reference.

Dosage forms for application to treat the eye are disclosed in U.S. Pat. No. 4,348,398, the disclosure of which is incorporated herein by reference.

Pharmaceutical compositions of the present invention suitable for oral administration and by inhalation in the case of asthma therapy may be presented as discrete units such as capsules, cachets or tablets each containing an predetermined amount of the active ingredient, as a powder or granules or as a solution or suspension in an agueous liguid, a non agueous liguid, an oil in-water emulsion or a water in-oil liguid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liguid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free flowing form such as powder or granules, optionally mixed with a binder, lubricant, inert diluent, lubricating, surface active or dispersing agent. Molded tablets may be made by molding in a suitable machine, a mixture of the powdered compound moistened with an inert liguid diluent. Desirably, each tablet contains from about 25 mg to about 500 mg of the active ingredient and each cachet or capsule contains from about 25 to about 500 mg of the active ingredient.

The following are examples of representative pharmaceutical dosage forms:

| Injectible Suspension | mg/mL |
|---|---|
| Compound of Formula I | 2 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Aerosol for Oral Inhibition | mg/can (200 doses/can) |
|---|---|
| Compound of Formula I | 2–40 |
| Oleic Acid | 0.2–4.0 |
| Trichloromonofluoro methane | 5,000–8,000* |
| Dichloromonofluoro methane | 15,000–12,400* |

| Cream | mg/g |
|---|---|
| Compound of Formula I | 1–100 |
| Cetyl alcohol | 130.0 |
| Sodium Lauryl Sulfate | 15.0 |
| Propylene Glycol | 100.0 |
| Methyl paraben | 1.8 |
| Propyl paraben | 1.2 |
| Purified Water of sufficient quantity to make total 1 g | |

| Ointment | mg/g |
|---|---|
| Compound of Formula I | 1–100 |
| Methyl paraben | 1.8 |
| Propyl paraben | 1.2 |
| Petrolatum of sufficient quantity to make total 1 g | |

| Tablet | mg/tablet |
|---|---|
| Compound of Formula I | 25 |
| Microcrystalline Cellulose | 325 |
| Providone | 14.0 |
| Microcrystalline Cellulose | 90.0 |
| Pregelatinized Starch | 43.5 |

| -continued | |
|---|---|
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

*To a total volume of 1 ml

In addition to the compounds of Formula I, the pharmaceutical compositions of the present invention can also contain other active ingredients, such as cyclooxygenase inhibitors, non steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non narcotic analgesics/non-steroidal anti inflammatory drugs which contain the basic structure:

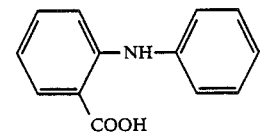

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

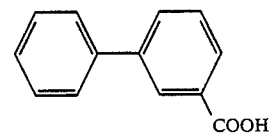

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4 hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non steroidal anti-inflammatory drugs which have the general formula:

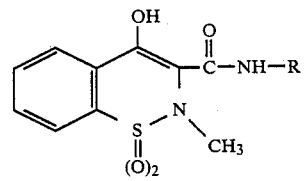

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydanine, beprozin, broperamole, bufezolac, carprofen, cinmetacin, ciproguazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproguazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proguazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ON03144, PR823, PV102, PV108, R830, RS2131, SCR152, SH440, SIR133, SPAS510, SQ27239, ST281, SY6001, TA60, TVX2706, U60257, UR2301 and WY41770.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in U.S.Pat. Nos. 4,666,907, 4,663,307, 4,611,056, and 4,634,766, which are hereby incorporated herein by reference.

The compounds of the Formula I may also be used in combination with leukotriene antagonists such as those disclosed in EP 106,565 (April 25, 1984) and EP 104,885 (April 4, 1984) which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in U.S. Pat. No. 4,536,507 or thromboxane antagonists such as those disclosed in U.S. Pat. No. 4,237,160. They may also contain histidin decarboxyase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP 40,696 (December 2, 1981) and like compounds, such as those disclosed in U.S. Pat. Nos. 4,283,408; 4,362,736; and 4,394,508. The pharmaceutical compositions may also contain a $K+/H+$ ATPase inhibitor such as omeprazole, disclosed in U.S. Pat. No. 4,255,431, and the like. Each of the references referred to in this paragraph is hereby incorporated herein by reference.

The following examples illustrate the present invention without, however, limiting the same thereto. All temperatures are in degrees Celsius.

EXAMPLE 1

4 hydroxy-2 (4-methoxybenzyl)-3-methyl-5-benzofuran

Step A

Preparation of
4-hydroxy-2-(4-methoxybenzoyl)-3-methyl-5-propylbenzofuran

A mixture of 2,6-dihydroxy-5-propyl acetophenone (5.8 g; 30 mmoles), ω-bromo-p-methoxyacetophenone (6.8 g; 30 mmoles), anhydrous potassium carbonate (4.1 g; 30 mmoles) and acetone (150 ml) was refluxed for 22 hours. The mixture was filtered and concentrated. The residue was dissolved in dichloromethane (500 ml) and extracted with 1 N sodium hydroxide ($2 \times 200$ ml) and water (200 ml). The dichloromethane solution containing the product was dried ($Na_2SO_4$), filtered, concentrated, and chromatographed to obtain 7.2 g of the title compound as a solid. A sample was recrystallized from 10% ethyl acetate in hexane.

m.p. 114°–116° C.

Calcd for $C_{20}H_{20}O_4$: C, 74.05; H, 6.21. Found: C, 74.30; H, 6.18.

Step B

Preparation of
4-hydroxy-2-(4-methoxybenzyl)-3-methyl-5-propylbenzofuran (7.2 g; 22 mmoles), potassium hydroxide pellets (8.7 g; 155 mmoles), ethylene glycol (100 ml) and 99%
hydrazine (3.0 ml) was heated with stirring and maintaining the internal temperature between 130° C. and 150° C. for 4 hours. The internal temperature was permitted to rise to 175° C. for 1 hour and excess water was always allowed to escape. The mixture was cooled and poured into excess 20% citric acid solution. The mixture was extracted with ether, washed with water, dried ($Na_2SO_4$), filtered, concentrated, and
chromatographed to give 4 grams of the title compound.

m.p. 83°–86° C.

Calcd for $C_{20}H_{22}O_3$: C, 77.39; H, 7.14. Found: C, 77.39; H, 7.06.

EXAMPLE 2

4-hydroxy-2-(4-hydroxybenzyl)-3-methyl-5-propylbenzofuran

Under nitrogen atmosphere, ethanethiol (4.9 g; 80 mmoles) was added dropwise over 5 minutes to a mixture Of 99% sodium hydride (1.9 g; 80 mmoles) in dimethylformamide (100 ml). After stirring for 15 minutes, a solution of 4-hydroxy-2-(4-methoxybenzyl)-3-methyl-5-propylbenzofuran (2.4 g; 8mmoles) in dimethylformamide (5 ml) was added in one portion. The mixture was refluxed for 2 hours, cooled, acidified with 20% citric acid solution and extracted with ether. The ether solution was washed with water, dried ($Na_2SO_4$), filtered, concentrated, and chromatographed to obtain 2.2 g of the title compound as an oil which crystallized from an ether hexane mixture.

m.p. 117°–120° C. ˙

Calcd for $C_{19}H_{20}O_3$: C, 77.00; H, 6.80. Found: C, 76.66; H, 7.32.

EXAMPLE 3

4-hydroxy-3-methyl-5-propyl-2-(4-pyridylmethyl)-benzofuran

Step A

Preparation of 4-hydroxy-3-methyl 5-propyl-2 -(isonicotinoyl) benzofuran

A mixture of 2,6-dihydroxy-5-propylaceto-phenone (5.8 g; 30mmoles), 4-bromoacetylpyridine hydrobromide (16.8 g; 60mmoles), anhydrous potassium carbonate (16.5 g; 120mmoles) and acetone (200 ml) was refluxed for 22 hours. The mixture was filtered, concentrated, and chromatographed to obtain 2 g of the title compound.

m.p. 203°–205° C.

Calcd for $C_{18}H_{17}NO_3$: C, 73.20; H, 5.80; N, 4.76. Found: C, 73.04; H, 5.88; N, 4.64.

Step B

Preparation of 4-hydroxy-3-methyl-5-propyl-2-(4-pyridylmethyl)-benzofuran

A mixture of 4 hydroxy 3 methyl 5 propyl-2 -(isonicotinoyl)-benzofuran (1.5 g; 5.2mmoles), potassium hydroxide pellets (2 g; 37mmoles), ethylene glycol (25 ml) and 99% hydrazine (0.8 ml) was heated with stirring at 130° C. for 1 hour and at 155° C. for 2 hours. The mixture was cooled and acidified with 20% citric acid solution. The mixture was extracted using 20% ethyl acetate in diethyl ether. The organic layer was dried ($Na_2SO_4$), filtered, concentrated, and chromatographed to obtain 1 g of the title compound which was then recrystallized from ethyl acetate.

m.p. 161°–163° C.

Calcd for $C_{18}H_{19}NO_2$: C, 76.84; H, 6.80; N, 4.97. Found: C, 76.66; H, 7.19; N, 4.90.

EXAMPLE 4

2-ethyl-4-hydroxy-3-methylbenzofuran

A mixture of 2-acetyl-4-hydroxy-3-methylbenzofuran (2 g; 10.5mmoles), potassium hydroxide pellets (4 g; 73mmoles), ethylene glycol (50 ml) and 99% hydrazine (3 ml) was heated at 100° C. for 2 hours and at 180° C. for 2 hours. The mixture was acidified with excess 20% citric acid solution and extracted with ether. The ether layer was dried ($Na_2SO_4$), filtered, concentrated, and chromatographed to obtain 1.2 g of the title compound as an oil which crystallized from hexane.

m.p. 105°–107° C.

Calcd for $C_{11}H_{12}O_2$: C, 74.97; H, 6.86. Found: C, 74.84; H, 6.76.

EXAMPLE 5

2-benzyl-4-hydroxy-3-methyl-5-propylbenzofuran

A mixture of 2-benzoyl-4-hydroxy-3-methyl-5-propylbenzofuran (1.2 g; 4mmoles), potassium hydroxide pellets (1.5 g; 28mmoles), ethylene glycol (25 ml) and 99% hydrazine (0.7 ml) was heated at 135°–155° C. for 3 hours. The mixture was cooled, acidified with 20% citric acid solution, extracted with ether, dried ($Na_2SO_4$), filtered, concentrated, and chromatographed to obtain 650 mg of the title compound as an oil which was crystallized from hexane.

m.p. 40°–41° C.

Calcd for $C_{19}H_{20}O_2$: C, 81.39; H, 7.19. Found: C, 81.46; H, 7.18.

EXAMPLE 6

5-allyl-2-ethyl-5-hydroxy-3-methylbenzofuran

Step A

Preparation of 4 allyloxy-2-ethyl-3-methyl-benzofuran

A mixture of 2-ethyl 4 hydroxy 3 methylbenzofuran (760 mgs; 4.3mmoles), allyl bromide (1.0 g; 8.6 mmoles), anhydrous potassium carbonate (1.1 g; g; 8.6mmoles) 8.6mmoles) and acetone (50 ml) was refluxed for 4 hours. The mixture was filtered, concentrated, and chromatographed to obtain 1.1 g of the title compound as an oil which was used as such in the next step.

Step B

Preparation of 5-allyl-2-ethyl-4-hydroxy-3-methylbenzofuran

A mixture of 4-allyloxy-2-ethyl-3-methylbenzofuran (1.0 g; 4.8mmoles) and orthodichlorobenzene (40 ml) was refluxed for 4 hours. The mixture was chromatographed to obtain 1.0 g of the title compound as an oil. The oil was recrystallized from hexane.

m.p. 38°–40° C.

Calcd for $C_{14}H_{16}O_2$: C, 77.74; H, 7.45. Found: C, 77.74; H, 7.06.

EXAMPLE 7 2-(1-(4-chlorophenyl)-vinyl)-3-methyl benzofuran

To a suspension of potassium t-butoxide (448 mg; 4mmoles) in tetrahydrofuran (25 mL) was added methyl-triphenylphosphonium bromide (1.07 gm; 3 mmoles). The mixture was stirred for a period o 2 hours. 2-(4-chlorobenzoyl)-3-methyl-4-hydroxybenzofuran (286 mg; 1mmole) in tetrahydrofuran (5 ml) was added rapidly and the mixture was stirred for an additional 30 minutes at room temperature. The mixture was poured into 10% citric acid solution (100 ml) and was extracted with ethylacetate. The organic phase was dried ($Na_2SO_4$), and concentrate in vacuo. The residue was chromatographed on silica gel and eluted with 10% ethylacetate in hexane to yield 210 mg (73%) of 2-(1-(4-chlorophenyl)vinyl)-3-methylbenzofuran as an oil.

$^1$H NMR 2.23 (s, 3H, $CH_3$), 5.57 (m, 2H, $CH_2$), 5.67 (s, 1H, OH), 6.43 (d of d, J=3 Hz, 9 Hz, H5), 7.00 (m, 2H, H6 and H7), 7.20 (s, 4H, phenyl protons).

Anal. Calcd for $C_{17}H_{13}ClO_2$: C, 71.70; H, 4.60; Cl, 12.45 Found: C, 71.54: H, 4.81; Cl, 12.35.

EXAMPLE 8

2-(3 formyl-4-methoxybenzyl)-3-methyl 4-hydroxy 5-propyl-benzofuran

To a suspension of aluminium chloride (214 mg; 1.6mmole) in dichloromethane (5 mL) cooled at 0° C. was added 2-(p-methoxy benzyl)-3-methyl-4-hydroxy-5-propyl benzofuran (100 mg; 0.32mmoles). A red solution resulted. To this solution was added dropwise dichloromethylmethylether (87 1; 0.96 mmole). There was a vigorous reaction and a color change from red to green was observed. Ice and water was then added and the mixture was extracted with ethylacetate. The organic phase was dried ($Na_2SO_4$), and concentrated in vacuo and the residue was chromatographed on silica gel. Elution with 10% ethylacetate in hexane yielded 40 mg (37%) of 2-(3 formyl-4-methoxybenzyl)-3-methyl-4-hydroxy-5-propyl-benzofuran.

$^1$H NMR 0.93 (t, 3H, J=7 Hz, CH$_3$), 1.60 (sextet, 2H, J=7 Hz, CH$_2$), 2.40 (s, 3H, CH$_3$), 2.63 (t, 2H, J=7 Hz, CH$_2$), 3.87 (s, 3H, CH$_3$), 3.97 (s, 2H, CH$_2$), 4.90 (s, 1H, OH), 6.90 (s, 2H, H6 and H7), 6.93 (d, 1H, J=9Hz, proton ortho to methoxy), 7.40 (d of d, 1H, J=9 HZ, 3Hz, proton meta to methoxy-0, 7.73 (d, 1H, J=3 Hz, proton ortho to formyl), 10.50 (s, 1H, formyl proton).

Anal. Calcd for C$_{21}$H$_{22}$O$_4$: C, 74.51; H, 6.55; Found: C, 74.56: H, 6.58.

EXAMPLE 9

2-(p-chlorobenzyl)-3-methyl-4-hydroxy-5-propyl-7-chlorobenzofuran (a) Preparation of 2-(p-chlorobenzoyl)-3-methyl-4-(chlorobenzoyloxy)-5-propyl-7-chlorobenzofuran A solution of p-chlorobenzoyl chloride (3.5 gm; 20mmoles) in ethylene dichloride (10 mL) was added slowly to a cooled suspension of aluminium chloride (5.36 gm; 40mmoles) in ethylene dichloride (200 mL). After stirring for a period of 15 minutes, 3-methyl 4-hydroxy-5-propyl-7-chlorobenzofuran (1.5 gm; 7mmoles) in ethylenedichloride (10 mL) was added over a period of 2 minutes. The reaction mixture was stirred at room temperature for 5 hours. It was cooled with an ice-bath and ice was added slowly. When the vigorous reaction subsided, the organic layer was separated and the agueous phase was extracted with methylene chloride. The organic phases were combined, dried (Na$_2$SO$_4$), and concentrated in vacuo. The residue was chromatographed on silica gel. Elution with 15% ethylacetate in hexane yielded 2.63 gm (75%) of 2-(p-chlorobenzoyl)-methyl-4-(p-chlorobenzoyloxy)-5-propyl-7-chlorobenzofuran, mp. 177°-182° C.

$^1$H NMR 0.90 (t, J=7Hz, 3H, CH$_3$), 1.63 (sextet, J=7 Hz, 2H, CH$_2$), 2.57 (s, 3H, CH$_3$), 2.63 (t, J=7 Hz, 2H, CH$_2$), 7.43 (d, J=9Hz, 1H, proton ortho to chloro), 7.50 (d, J=9Hz, 1H, proton ortho to chloro), 7.60 (s, 1H, H6),8.17 (d, J=9Hz, 1H, proton meta to chloro, 8.23 (d, J=9Hz, 1H, proton meta to chloro).

(b) Preparation of 2-(p-chlorobenzyl)-3-methyl-4-hydroxy-5-propyl-7-chlorobenzofuran To an ice-cold suspension of aluminium chloride (2.1 gm, 16mmoles) in ether (300 mL) was added slowly lithium aluminium hydride (2.6 gm, 68 mmoles). After stirring for a period of 10 minutes, 2-(p-chlorobenzoyl)-3-methyl-4-(p-chlorobenzoyloxy)-5-propyl-7-chlorobenzofuran (2.3 gm, 4.6mmoles) in ether (10 mL) was added over a period of 2 minutes. The reaction mixture was stirred at room temperature for 15 minutes. It was cooled with an ice bath and ice was added slowly. When the vigorous reaction subsided, the organic layer was separated and the agueous phase was extracted with ether. The organic phases were combined, washed with brine, dried (Na$_2$SO$_4$), and concentrated in vacuo. The residue was chromatographed on silica gel. Elution with 15% ethylacetate in hexane yielded 0.30 gm (87%) of 2-(p-chlorobenzyl)-3-methyl-4-hydroxy-5-propyl-7-chlorobenzofuran, mp.76°-77° C.

$^1$H NMR 0.97 (t, J=7Hz, 3H, CH$_3$), 1.67 (sextet, J=7 Hz, 2H, CH$_2$), 2.33 (s, 3H, CH$_3$), 2.57 (t, J=7 Hz, 2H, CH$_2$), 4.03 (s, 2H, CH$_2$), 4.80 (s, 1H, OH), 6.93 (s, 1H, H6), 7.17 (d, 2H, J=9Hz, proton ortho to chloro), 7.30 (d, J=9Hz, 1H, proton meta to chloro).

EXAMPLE 10

2-(p-fluorobenzyl)-3 methyl-5 propyl-4-hydroxybenzofuran (a) Preparation of 2-hydroxy-5-allyloxyacetophenone A mixture of 2,5-dihydroxyacetophenone (7.6 gm; 50mmoles), potassium carbonate (6.9 gm; 50 mmoles) and allyl bromide (6.0 gm; 50mmoles) in acetone (100 mL) was refluxed for a period of 18 hours. The reaction mixture was cooled, filtered through Celite (diatomaceous earth) and concentrated in vacuo. The residue was chromatographed on silica gel using 20% ethylacetate in hexane as eluent to yield 11.2 gm (97%) of 2-hydroxy-5-allyloxyacetophenone, mp. 51°-53° C.

$^1$H NMR 2.60 (s, 3H, CH$_3$), 4.52 (d,J=6Hz, 2H,OCH$_2$), 5.30 (m, 1H, CH), 6.00 (m, 2H, CH$_2$, 6.83 (d, J=9 Hz, 1H, proton ortho to hydroxyl), 7.13 (m, 2H, proton ortho to allyloxy).

Anal. Calcd for C$_{11}$H$_{12}$O$_3$: C, 68.75; H, 6.25. Found: C, 68.74: H, 6.53.

(b) Preparation of 2-(p-fluorobenzoyl)-3 methyl-5-allyloxybenzofuran

A mixture of 2-hydroxy-5-allyloxyacetophenone (5.0 gm; 26mmoles), potassium carbonate (3.9 gm; 28 mmoles) and p-fluorophenacylbromide (6.2 gm; 28 mmoles) in methylethylketone (75 mL ) was refluxed for a period of 22 hours. The reaction mixture was cooled, filtered through Celite and concentrated in vacuo. The residue was chromatographed on silica gel using 15% ethylacetate in hexane as eluent to yield 3.9 gm (48%) of 2-(p-fluorobenzoyl)-3-methyl-5-allyloxybenzofuran, mp. 80°-82° C.

$^1$H NMR 2.67 (s, 3H, CH$_3$), 4.60 (m, 2H, CH$_2$), 5.43 (m, 2H, CH$_2$), 6.13 (m, 1H, CH), 7.20 (d, 3H, J= 9Hz, protons ortho to fluoro and H7), 7.27 (d, J=3Hz, 1H, H4), 7.47 (d of d, J=3Hz, 9Hz, H6), 8.18 (d of d, 2H, J=5Hz, 9Hz, protons ortho to carbonyl).

Anal. Calcd for C$_{19}$H$_{15}$FO$_3$: C, 73.53; H, 4.87; F, 6.12. Found: C, 73.98: H, 4.85; F, 6.08.

(c) Preparation of 2-(p-fluorobenzoyl)-3-methyl-4-allyl-5-hydroxybenzofuran

A solution of 2-(p-fluorobenzoyl)-3-methyl-5-allyloxybenzofuran (2.77 gm; 9.2mmoles) in ortho dichlorobenzene (15 mL) was refluxed under nitrogen for a period of 4 hours. On cooling, the reaction product crystallized. Some hexane was added and the crystals were filtered, washed with hexane and air-dried to yield 2.1 gm (76%) of 2 (p-fluorobenzoyl)-3-methyl-4-allyl-5-hydroxybenzofuran, mp. 164°-166° C.

$^1$H NMR 2.80 (s, 3H, CH$_3$), 3.80 (m, 2H, CH$_2$), 5.07 (m, 2H, CH$_2$), 7.20 (m, 4H, protons ortho to fluoro, H5 and H7), 8.10 (d of d, 2H, J=5Hz, 9Hz, protons ortho to carbonyl).

Anal. Calcd for C$_{19}$H15FO$_3$: C, 73.53; H, 4.87; F, 6.12. Found: C, 73.53: H, 4.84; F, 6.33.

(d) Preparation of 2-(p-fluorobenzoyl)-3-methyl-4-propyl-5-hydroxybenzofuran

A solution of 2-(p-fluorobenzoyl)-3-methyl-4-allyl-5-hydroxybenzofuran (1.5 gm; 4.8mmoles) in ethanol (50 mL) was hydrogenated in a Parr apparatus in presence of 10% palladium on carbon. The catalyst was removed by filtration and the filtrate was concentrated to dryness. The residue was chromatographed on silica gel using 20% ethylacetate in hexane as eluent to yield 600 mg (42%) of 2-(p-fluorobenzyl)-3-methyl-4-propyl-5-hydroxybenzofuran, mp 121°–123° C.

$^1$H NMR 0.97 (t, 3H, J=7Hz, CH$_3$), 1.63 (sextet, 2H, J=7Hz, CH$_2$), 2.27 (s, 3H, CH$_3$), 2.83 (t, 2H, J=7 Hz, CH$_2$), 3.93 (s, 2H, CH$_2$), 4.40 (s, 2H, CH$_2$), 6.90 (m, 6H, aromatic protons).

Anal. Calcd for C$_{19}$H$_{19}$FO$_2$: C, 76.48; H, 6.41; F, 6.36. Found: C, 76.11; H, 6.48; F, 6.55.

EXAMPLE 11

2-(4-hydroxybenzyl)-3-methyl-4-propyl-5-hydroxybenzofuran

Under nitrogen, ethanethiol (3.1 gm; 50 mmoles) was added dropwise over 5 minutes to a mixture of 99% sodium hydride (1.2 gm; 50mmoles) in dimethylformamide (100 mL). After stirring for 15 minutes, a solution of 2-(4-methoxybenzyl)-3-methyl-4-propyl-5-hydroxybenzofuran (2.1 gm; 6.7mmoles) in dimethylformamide (DMF) (25 mL) was added in one portion. The mixture was refluxed for 1.5 hours, cooled, acidified with 20% citric acid and extracted with ether. The ether solution was washed with water, dried (Na$_2$SO$_4$), filtered, and concentrated in vacuo. The resulting oil crystallised on standing at room temperature overnight. The crystals were slurried with hexane, filtered, washed with hexane, and air dried to yield 2-(4-hydroxybenzyl)-3-methyl-4-propyl-5-hydroxybenzofuran, mp. 138°–142° C.

$^1$H NMR 1.03 (t, 3H, J=7Hz, CH$_3$), 1.67 (sextet, 2H, J=7Hz, CH$_2$), 2.37 (s, 3H, CH$_3$), 2.90 (t, 2H, J=7 Hz, CH$_2$), 3.80 (s, 3H, CH$_3$), 3.97 (s, 2H, CH$_2$), 4.50 (s, 2H, CH$_2$), 6.53 (d, 1H, J=9 Hz, H6), 6.80 (d, 2H, J=9Hz, protons ortho to methoxy), 7.07 (d, 1H, J=9 Hz, H7) 7.20 (d, 2H, J=9 Hz, protons meta to methoxy).

Anal. Calcd for C$_{19}$H$_{20}$O$_3$: C, 77.00; H, 6.80. Found: C, 77.64: H, 6.66.

EXAMPLE 12

2 (p methoxybenzyl)-3-methyl 4-hydroxy-5-chloro-7-propylbenzofuran (a) Preparation of 2-hydroxy-3-chloro-6-allyloxyacetophenone A mixture of 2,6-dihydroxy-3-chloroacetophenone (1.2 gm; 6.2mmoles), potassium carbonate (8.55 mg; 6.2mmoles) and allyl bromide (562 E1; 6.5 mmoles) in acetone (30 mL) was refluxed for a period of two hours. The reaction mixture was cooled, filtered through Celite, and concentrated in vacuo. The residue was chromatographed on silica gel using 20% ethylacetate in hexane as eluent to yield 627 mg (45%) of 2-hydroxy-3-chloro-6-allyloxyacetophenone.

$^1$H NMR 2.74 (s, 3H, CH$_3$), 4.55 (d,J=6Hz, 2H,OCH$_2$), 5.40 (m, 2H, CH$_2$), 6.10 (m, 1H, CH), 6.76 (d, J=9 Hz, 1H,H5), 7.43 (d,J=9Hz, 1H, H4).

(b) Preparation of 2-(p methoxybenzoyl)-3-methyl-4-allyloxy-5-chlorobenzofuran

A mixture of 2-allyloxy-3-chloro-6-hydroxyacetophenone (587 mg; 2.6mmoles), potassium carbonate (357 mg; 2.6mmoles) and p methoxyphenacyl bromide (590 mg; 2.6mmoles) in acetone (15 mL ) was refluxed for a period of 18 hours. The reaction mixture was cooled, filtered through Celite, and concentrated in vacuo. The residue was chromatographed on silica gel using 20% ethylacetate in hexane as eluent to yield 2-(p methoxybenzoyl)-3-methyl-4-allyloxy-5-chlorobenzofuran.

$^1$H NMR 2.73 (s 3H, CH$_3$), 3.88 (s, 3H, CH$_3$), 4.62 (d, 2H,J=6 Hz, CH$_2$), 5.40 (m, 2H, CH$_2$), 6.16 (m, 1H, CH$_2$), 7.00 (d, 2H, J=9 Hz, protons ortho to methoxy), 7.23 (d, J=9Hz, 1H, H6), 7.41 (d, J=9 Hz, 1H, H5), 8.08 (d, 2H, J=9Hz, protons ortho to carbonyl).

(c) Preparation of 2-(p-methoxybenzoyl)-3-methyl-4-hydroxy-5-chloro-7-allyl-benzofuran A mixture of 2-(p-methoxybenzoyl)-3-methyl-4-allyloxy-5-chlorobenzofuran (400 mg; 1.12mmoles) in ortho-dichlorobenzene (15 mL) was refluxed under nitrogen for 1.5 hours. The reaction mixture was cooled to room temperature and purified by chromatography on silica gel using 20% ethylacetate as eluent to yield 110 mg (27%) of 2-(p-methoxybenzoyl)-3-methyl-4-hydroxy-5-chloro-7-allylbenzofuran.

$^1$H NMR 2.79 (s 3H, CH$_3$), 3.54 (d, 2H,J=6 Hz, CH$_2$), 3.90 (s, 3H, CH$_3$), 5.15 (m, 2H, CH$_2$), 5.96 (m, 1H, CH$_2$), 6.96 (d, 2H, J=9 Hz, protons ortho to methoxy), 7.17 (s, 1H, H6), 8.12 (d, 2H, J=9Hz, protons ortho to carbonyl).

(d) Preparation of 2-(p-methoxybenzoyl)-3-methyl-4-hydroxy-5-chloro-7-propylbenzofuran A solution of 2-(p-methoxybenzoyl)-3-methyl-4-hydroxy-5-chloro-7-allylbenzofuran (110 mg; 0.31mmole) in ethanol (15 mL) was hydrogenated in a Parr apparatus at 20 psi in the presence of 5% palladium on charcoal. The catalyst was filtered off and the filtrate was evaporated in vacuo to yield 110 mg of 2-(p-methoxybenzoyl)-3-methyl-4-hydroxy-5-chloro-7-propylbenzofuran.

$^1$H NMR 0.93 (t, J=7Hz, 3H, CH$_3$), 1.70 (sextet, J=7 Hz, 2H, CH$_2$), 2.38 (s, 3H, CH$_3$), 2.76 (t, J=7 Hz, 2H, CH$_2$), 2.79 (s, 3H, CH$_3$), 3.90 (s, 3H, CH$_3$), 5.80 (s, 1H, OH), 7.00 (d, J=9Hz, 2H, protons ortho to methoxy), 7.15 (s, 1H, H6 ), 8.10 (d, J=9Hz, 2H, proton meta to methoxy).

(e) Preparation of 2-(p-methoxybenzoyl)-3-methyl-4-hydroxy-5-chloro-7-propylbenzofuran A solution of 2-(p-methoxybenzoyl)-3-methyl-4-hydroxy-5-chloro-7-propylbenzofuran (90 mg; 0.25 mmole), hydrazine (80 µl) and potassium hydroxide (98 mg) in ethylene glycol (2 mL) was heated at 145° C. for a period of 5 hours. The reaction mixture was cooled, poured in water, and extracted with ether. The organic phase was washed with 20% citric acid, with brine, dried (Na$_2$SO$_4$), and concentrated in vacuo. The residue was chromatographed on silica gel using 20% ethylacetate in hexane as eluent to yield 47 mg (50%) of 2-(p-methoxybenzyl) 3-methyl-4hydroxy-5-chloro-7-propylbenzofuran.

$^1$H NMR 0.93 (t, J=7Hz, 3H, CH$_3$), 1.66 (sextet, J=7 Hz, 2H, CH$_2$), 2.36 (s, 3H, CH$_3$), 2.70 (t, J=7 Hz, 2H, CH$_2$), 3.78 (s, 3H, CH$_3$), 4.00 (s, 2H, CH$_2$), 5.50 (s, 1H, OH), 6.84 (d, J=9Hz, 2H, protons ortho to methoxy), 6.91 (s, 2H, H6 ), 7.15 (d, J=9Hz, 2H, proton meta to methoxy).

EXAMPLE 13

2-(p-methoxybenzyl)-3-methyl-6-hydroxy-7-propylbenzofuran (a) Preparation of 4-benzyloxy-3-propyl-2-hydroxyacetophenone A mixture of 2,4 dihydroxy-3-propyl-aceto phenone (5.8 gm; 30mmoles), potassium carbonate (8.3 gm; 60mmoles) and benzylbromide (5.6 gm; 33mmoles) in methylethylketone (60 mL) was refluxed for a period of 4 hours. The reaction mixture was cooled, filtered through Celite, and concentrated in vacuo. The residue crystallized on stirring with hexane. It was filtered, washed with hexane, and air dried to yield 6.67 gm (78%) 4-benzyloxy-3-propyl-2-hydroxyacetophenone.

(b) Preparation of 2-(p-methoxybenzoyl)-3-methyl-6-benzyloxy-7-propylbenzofuran

Sodium hydride (0.66 gm; 27.5mmoles) was added to an ice-cold mixture of 4-benzyloxy-3-propyl-2-hydroxyacetophenone (6.4 gm, 22.5mmoles) and dimethylformamide (64 mL). After stirring for 30 minutes, more sodium hydride (0.4 gm, 17.5mmoles) was added, followed by p-methoxyphenacyl bromide (2.91 gm, 12.7mmoles). The reaction was stirred for 24 hours at room temperature. The mixture was poured on ice and a slight excess of hydrochloric acid was added. The resulting mixture was extracted with ether. The organic phase.was separated, washed with water, dried ($Na_2SO_4$), and concentrated in vacuo. The residue crystallized from methanol. The solid was filtered, washed with methanol, and air-dried to yield 2-(p-methoxybenzoyl)-3-methyl 6-benzyloxy-7-propylbenzofuran, mp. 105°-106° C.

(c) Preparation of 2-(p-methoxybenzyl)-3-methyl-6-benzyloxy-7-propylbenzofuran

A solution of 2-(p-methoxybenzoyl)-3-methyl-6-benzyloxy-7-propylbenzofuran (1.04 gm, 2.5 mmoles) in ethanol (100 mL) was hydrogenated in a Parr hydrogenator in the presence of 10% palladium on charcoal for a period of 24 hours. The catalyst was filtered off and the filtrate was concentrated in vacuo. The residue was purified by chromatography on silica gel and eluted with 25% ethylacetate in hexane to yield 110 mg of 2-(p-methoxybenzyl)-3-methyl-6-hydroxy-7-propylbenzofuran.

$^1$H NMR 0.97 (t, 3H, J=9Hz, $CH_3$), 1.63 (sextet, 2H, J=7Hz, $CH_2$), 2.17 (s, 3H, $CH_3$), 2.80 (t, 2H, J=7 Hz, $CH_2$), 3.80 (s, 3H, $CH_3$), 4.00 (s, 2H, $CH_2$), 4.63 (s, 1H, OH), 6.70 (d, 1H, J=9Hz, H5), 6.83 (d, 2H, J=9Hz, protons ortho to methoxy), 7.13 (d, 1H, J=9Hz, H4), 7.17 (d, 2H, J=9Hz, protons meta to methoxy)

EXAMPLE 14

2-(p-methoxybenzyl)-3-methyl-4-acetoxy-5-propyl-7-fluorobenzofuran

A solution of 2-(p-methoxybenzyl)-3-methyl-4-hydroxy-5-propyl-7-fluorobenzofuran (0.10 gm, 0.3 mmoles), acetic anhydride (0.5 mL) and triethylamine (0.7 mL) in tetrahydrofuran (15 mL) was stirred at room temperature overnight. The volatiles were removed in vacuo and the residue was purified by chromatography on silica gel and eluted with 15% ethylacetate in hexane to yield 90 mg (80%) of 2-(p-methoxybenzyl)-3-methyl-4-acetoxy-5-propyl-7-fluorobenzofuran, mp. 85°-88° C.

$^1$H NMR 0.97 (t, 3H, J=9Hz, $CH_3$), 1.53 (sextet, 2H, J=7Hz, $CH_2$), 2.17 (s, 3H, $CH_3$), 2.40 (s, 3H, $CH_3$), 2.53 (t, 2H, J=7Hz, $CH_2$), 3.77 (s, 3H, $CH_3$), 3.98 (s, 2H, $CH_2$), 6.73 (m, 3H, H6 and protons ortho to methoxy), 7.13 (d, 2H, J=9Hz, protons meta to methoxy).

EXAMPLE 15

2-(p-methoxybenzyl)-3-methyl-4-acetoxy-5-propyl-7-chlorobenzofuran

A solution of 2 (p-methoxybenzyl) 3 methyl 4-hydroxy 5-propyl 7 chlorobenzofuran (0.10 gm, 0.29 mmoles), acetic anhydride (0.5 mL) and triethylamine (1.0 mL) in tetrahydrofuran (15 mL) was stirred at room temperature overnight. The volatiles were removed in vacuo. The residue was purified by chromatography on silica gel and eluted with 15% ethylacetate in hexane to yield 100 mg (91%) of 2-(p-methoxy benzyl)-3-methyl-4-acetoxy-5-propyl 7-chlorobenzofuran, mp. 119°-120° C.

$^1$H NMR 0.97 (t, 3H, J=9Hz, $CH_3$), 1.53 (sextet, 2H, J=7Hz, $CH_2$), 2.20 (s, 3H, $CH_3$), 2.40 (s, 3H, $CH_3$), 2.53 (t, 2H, J=7Hz, $CH_2$), 3.80 (s, 3H, $CH_3$), 4.00 (s, 2H, $CH_2$), 6.80 (d, 2H, J=9Hz, protons ortho to methoxy), 7.07 (s, 1H, H6), 7.10 (d, 2H, J=9Hz, protons meta to methoxy).

EXAMPLE 16

2-(p-methoxybenzyl)-3-methyl-4-propyl-5-acetoxybenzofuran

A solution of 2-(p-methoxybenzyl)-3-methyl-4-propyl-5-hydroxy-benzofuran (1.2 gm, 3.87mmoles), acetic anhydride (0.5 mL) and triethylamine (1.0 mL) in tetrahydrofuran (15 mL) was stirred at room temperature overnight. The volatiles were removed in vacuo. The residue was purified by chromatography on silica gel and eluted with 15% ethylacetate in hexane to yield 1.2 gm (79%) of 2-(p-methoxybenzyl)-3-methyl-4-propyl 5-acetoxybenzofuran, mp. 39°-41° C.

$^1$H NMR 1.00 (t, 3H, J=9Hz, $CH_3$), 1.57 (sextet, 2H, J=7Hz, $CH_2$), 2.28 (s, 3H, $CH_3$), 2.30 (s, 3H, $CH_3$), 2.78 (t, 2H, J=7Hz, $CH_2$), 3.73 (s, 3H, $CH_3$), 4.00 (s, 2H, $CH_2$), 6.80 (d, 1H, J=9Hz, H6), 6.83 (d, 2H, J=9Hz, protons ortho to methoxy), 7.10 (d, 2H, J=9Hz, protons meta to methoxy), 7.17 (d, 1H, J=9Hz, H7).

EXAMPLE 17

2-(p-methoxybenzyl)-3-methyl-4-ethoxycarbonyloxy-5-propyl-7-fluorobenzofuran A solution of 2-(p-methoxybenzyl)-3-methyl-4-hydroxy-5-propyl-7-fluorobenzofuran (0.10 gm, 0.3 mmoles), ethyl chloroformate (0.1 mL) and triethylamine (0.7 mL) in tetrahydrofuran (15 mL) was stirred at room temperature overnight. The volatiles were removed in vacuo. The residue was purified by chromatography on silica gel and eluted with 15% ethylacetate in hexane to yield 90 mg (80%) of 2-(p-methoxybenzyl)-3-methyl-4-ethoxycarbonyloxy-5-propyl-7-fluorobenzofuran, mp. 85°-88° C.

$^1$H NMR 0.97 (t, 3H, J=9Hz, $CH_3$), 1.53 (sextet, 2H, J=7Hz, $CH_2$), 2.17 (s, 3H, $CH_3$), 2.40 (s, 3H, $CH_3$), 2.53 (t, 2H, J=7Hz, $CH_2$), 3.77 (s, 3H, $CH_3$), 3.98 (s, 2H, $CH_2$), 6.73 (m, 3H, H6 and protons ortho to methoxy), 7.13 (d, 2H, J=9Hz, protons meta to methoxy).

EXAMPLE 18

2-(p-methoxybenzyl)-3-methyl-4-ethoxycarbonyloxy-5-
-propyl--7-chlorobenzofuran

A solution of 2-(p-methoxybenzyl)-3-methyl-4-hydroxy-5-propyl-7-chlorobenzofuran (0.10 gm, 0.29 mmoles), ethyl chloroformate (0.1 mL) and triethylamine (1.0 mL) in tetrahydrofuran (15 mL) was stirred at room temperature overnight. The volatiles were removed in vacuo. The residue was purified by chromatography on silica gel and eluted with 15% ethylacetate in hexane to yield 100 mg (91%) of 2 (p-methoxybenzyl) 3 methyl 4 ethoxycarbonyloxy 5 -5-propyl 7 chlorobenzofuran, mp. 99°–100° C.

$^1$H NMR 0.97 (t, 3H, J=9Hz, CH$_3$), 1.53 (sextet, 2H, J=7Hz, CH$_2$), 2.20 (s, 3H, CH$_3$), 2.53 (t, 2H, J=7 Hz, CH$_2$), 3.78 (s, 3H, CH$_3$), 3.98 (s, 3H, CH$_3$), 4.07 (s, 2H, CH$_2$), 6.87 (d, 2H, J=9 Hz, protons ortho to methoxy), 7.17 (s, 1H, H6), 7.20 (d, 2H, J=9Hz, protons meta to methoxy).

EXAMPLE 19

2-(p-methoxybenzyl)-3-methyl-4-propyl-5-ethoxycarbonyloxy-benzofuran

A solution of 2-(p-methoxybenzyl)-3-methyl-4-propyl-5-hydroxybenzofuran (1.2 gm, 3.87mmoles), ethyl chloroformate (0.1 mL) and triethylamine (1.0 mL) in tetrahydrofuran (15 mL) was stirred at room temperature overnight. The volatiles were removed in vacuo. The residue was purified by chromatography on silica gel and eluted with 15% ethylacetate in hexane to yield 1.2 gm (79%) of 2 (p-methoxybenzyl) 3-methyl-4-propyl-5-ethoxycarbonyloxybenzofuran, mp. 51°–53° C.

$^1$H NMR 1.00 (t, 3H, J=9Hz, CH$_3$), 1.60 (sextet, 2H, J=7Hz, CH$_2$), 2.33 (s, 3H, CH$_3$), 2.83 (t, 2H, J=7 Hz, CH$_2$), 3.80 (s, 3H, CH$_3$), 3.93 (s, 3H, CH$_3$), 4.00 (s, 2H, CH$_2$), 6.80 (d, 1H, J=9Hz, H6), 6.90 (d, 2H, J=9Hz, protons ortho to methoxy), 7.18 (d, 2H, J=9Hz, protons meta to methoxy), 7.23 (d, 1H, J=9Hz, H7).

EXAMPLE 20

2-(p-methoxybenzyl)-3-methyl-4-hydroxy-5-propyl-7-bromobenzofuran

A solution of 2-(p-methoxybenzyl)-3-methyl-4-hydroxy-5-propyl-benzofuran (1 gm; 3.22mmoles) in methylene chloride (30 mL) was cooled at 0° C. and bromine (0.52 gm; 3.22mmoles) in methylene chloride (10 mL) was added dropwise. The reaction mixture was stirred for 15 minutes. The reaction mixture was washed with a saturated sodium bicarbonate solution, dried (Na$_2$SO$_4$), and concentrated in vacuo. The residue was purified by preparative TLC, eluting with 15% ethylacetate in hexane to yield 2-(p-methoxybenzyl)-3-methyl-4-hydroxy-5-propyl-7-bromobenzofuran, mp. 110°–112° C.

$^1$H NMR 0.98 (t, J=7Hz, 3H, CH$_3$), 1.63 (sextet, J=7 Hz, 2H, CH$_2$), 2.36 (s, 3H, CH$_3$), 2.55 (t, J=7 Hz, 2H, CH$_2$), 3.78 (s, 6H, CH$_3$), 4.00 (s, 2H, CH$_2$), 4.97 (s, 1H, OH), 6.83 (d, J=9Hz, 2H, protons ortho to methoxy), 7.07 (s, 1H, H6), 7.17 (d, J=9Hz, 2H, proton meta to methoxy).

EXAMPLE 21

2-(p-methoxybenzyl)-3,7-dimethyl-4-hydroxy-5-propyl-benzofuran (a) Preparation of
2-(p-methoxybenzyl)-3-methyl-4-4-hydroxy-5-propyl-7-dimethylaminomethylbenzofuran A solution of 2-(p-methoxybenzyl)-3-methyl-4-hydroxy-5-propyl-benzofuran (155 mg gm; 0.5mmole) in methylene chloride (2 mL) was reacted with Eschenmoser's salt (dimethyl methylene-ammonium iodide) (105 mg; 0.5mmole) overnight at room temperature. The reaction mixture was concentrated in vacuo. The residue was taken up in ethylacetate, potassium carbonate was added and the mixture was stirred for a period of 15 minutes. The solids were separated and the ethylacetate solution was evaporated to yield 228 mg of 2-(p-methoxybenzyl)--3-methyl-4-hydroxy-5-propyl-7-dimethylaminomethylbenzofuran.

$^1$H NMR 0.98 (t, J=7Hz, 3H, CH$_3$), 1.70 (sextes, J=7 Hz, 2H, CH$_2$), 2.33 (s, 6H, CH$_3$N), 2.43 (s, 3H, CH$_3$), 2.63 (t, J=7 Hz, 2H, CH$_2$), 3.73 (s, 2H, CH$_2$N), 3.83 (s, 3H, CH$_3$O), 4.07 (s, 2H, CH$_2$), 4.90 (s, 1H, OH), 6.90 (d, J=9Hz, 2H, protons ortho to methoxy), 6.93 (s, 1H, H6), 7.23 (d, J=9Hz, 2H, proton meta to methoxy).

(b) Preparation of
2-(p-methoxybenzyl)-3,7-dimethyl-4-hydroxy-5-propyl-benzofuran To a solution of 2-(p-methoxybenzyl)-3-methyl-4-hydroxy-5-propyl-7-dimethylaminomethylbenzofuran (0.2 gm; 0.54mmole) in ethanol (5 mL) was added sodium borohydride (0.2 gm, 5.45mmoles) and the reaction mixture was refluxed for 10 minutes. The reaction mixture was cooled, poured in a saturated solution of ammonium chloride, and extracted with ether. The organic phase was washed with with brine, dried (Na$_2$SO$_4$), and concentrated in vacuo. The residue was chromatographed on silica gel using 20% ethylacetate in hexane as eluent to yield 160 mg (91%) of 2-(p-methoxybenzyl)-3,7-dimethyl-4-hydroxy-5-propylbenzofuran, mp. 102°–104° C.

$^1$H NMR 0.98 (t, J=7Hz, 3H, CH$_3$), 1.67 (sextet, J=7 Hz, 2H, CH$_2$), 2.37 (s, 3H, CH$_3$), 2.43 (s, 3H, CH$_3$), 2.63 (t, J=7 Hz, 2H, CH$_2$), 3.78 (s, 3H, CH$_3$), 4.00 (s, 2H, CH$_2$), 4.60 (s, 1H, OH), 6.73 (s, 1H, H6), 6.83 (d, J=9Hz, 2H, protons ortho to methoxy), 7.20 (d, J=9Hz, 2H, proton meta to methoxy).

Anal. Calcd for C$_{21}$H$_{24}$O$_3$: C, 77.73; H, 7.46; Found: C, 77.88: H, 7.55.

EXAMPLE 22

2-(p-methoxybenzyl)-3-methyl-4-hydroxy-5,7-dipropyl-benzofuran (a) Preparation of
2-(p-methoxybenzoyl)-3-methyl-4-hydroxy-5,7-dipropylbenzofuran A mixture of 2,6-dihydroxy-3,5-dipropylacetophenone (3.38 gm; 14.3mmoles), potassium carbonate (1.97 gm; 14.3mmoles) and p-methoxy-phenacylbromide (3.27 gm; 14.3mmoles) in acetone (50 mL) was refluxed for a period of eighteen hours. The reaction mixture was cooled, filtered through Celite, and concentrated in vacuo. The residue was chromatographed on silica gel using 20% ethylacetate in hexane as eluent to yield 0.40 gm (8%) of 2-(p-methoxybenzoyl)-3-methyl-4-hydroxy-5,7-dipropylbenzofuran, mp. 119°–121° C.

$^1$H NMR 0.93 (t, J=7Hz, 3H, CH$_3$), 0.98 (t, J=7Hz, 3H, CH$_3$), 1.66 (sextet, J=7Hz, 4H, CH$_2$), 2.60 (t, J=7 Hz, 2H, CH$_2$), 2.70 (t, J=7 Hz, 2H, CH$_2$), 2.80 (s, 3H, CH$_3$), 3.90 (s, 3H, CH$_3$), 5.00 (s, 1H, OH), 6.93 (s, 1H, H6), 6.98 (d, J=9Hz, 2H, proton ortho to methoxy), 8.13 (d, J=9 Hz, 2H, proton ortho to carbonyl).

(b) Preparation of 2-(p-methoxybenzyl)-3-methyl-4-hydroxy-5,7-dipropylbenzofuran A mixture of 2 (p-methoxybenzoyl)-3 methyl-4-hydroxy-5,7-dipropylbenzofuran (0.30 gm; 0.80 mmoles), 99% hydrazine (0.2 mL), potassium hydroxide (0.40 gm; 7mmoles) in ethylene glycol (10 mL) was heated at 140° C. for a period of 2.5 hours and at 195° C. for one hour. The reaction mixture was cooled, poured into water, and extracted with ethylacetate. The organic phase was washed with 20% citric acid, with brine, dried (Na$_2$SO$_4$), and concentrated in vacuo. The residue was chromatographed on silica gel using 20% ethylacetate in hexane as eluent to yield 140 mg (50%) of 2-(p-methoxybenzyl)-3-methyl-4-hydroxy-5,7-dipropylbenzofuran, mp. 70°–72° C.

$^1$H NMR 0.93 (t, J=7Hz, 3H, CH$_3$), 0.98 (t, J=7Hz, 3H, CH$_3$), 1.63 (sextet, J=7Hz, 2H, CH$_2$), 1.68 (sextet, J=7Hz, 2H, CH$_2$), 4H, CH$_2$), 2.38 (s, 3H, CH$_3$), 2.60 (t, J=7Hz, 2H, CH$_2$), 2.68 (t, J=7Hz, 2H, CH$_2$), 3.77 (s, 3H, CH$_3$), 3.93 (s, 2H, CH$_2$), 4.70 (s, 1H, OH), 6.70 (s, 2H, H6 and H7), 6.80 (d, J=9Hz, 2H, proton ortho to methoxy), 6.90 (s, 1H, H6), 7.17 (d, J=9 Hz, 2H, proton meta to methoxy).

Anal. Calcd for C$_{20}$H$_{22}$O$_3$: C, 78.37; H, 8.00; Found: C, 77.82: H, 7.70.

EXAMPLE 23

2-(p-methoxybenzyl)-3-methyl-4-hydroxy-5-propyl-7-chlorobenzofuran (a) Preparation of 2,6-dihydroxy-3-propyl-5-chloroacetophenone A mixture of 2,6-dihydroxy-3-propylacetophenone (40 gm, 0.206 mole) and N-chlorosuccinimide (40 gm; 0.300 mole) in methylene chloride (3 liters) was stirred at room temperature for a period of two days. The reaction mixture was poured onto a 3 liter fritted disk funnel filled with silica gel and elution was carried out with methylene chloride. Evaporation of the filtrate yielded 2,6-dihydroxy-3-propyl-5-chloroacetophenone; m.p.: 64°–65° C.

$^1$H NMR 0.93 (t, J=7Hz, 3H, CH$_3$), 1.63 (sextet, J=7 Hz, 2H, CH$_2$), 2.53 (t, J=7 Hz, 2H, CH$_2$), 2.73 (s, 3H, CH$_3$), CH$_2$), 6.33 (s, 1H, proton ortho to chloro 13.13 (s, 1H, OH).

(b) Preparation of 2-carboethoxymethoxy-6-hydroxy-3-chloro-5-propylacetophenone

A mixture of 2,6-dihydroxy-5-chloro-3-propylacetophenone (38.5 gm, 0.169 mole), ethyl bromoacetate (18.6 ml; 0.169 mole) and potassium carbonate (23.24 gm; 0.169 mole) in acetone (3 liters) was refluxed for a period of 2.5 hours. The reaction mixture was filtered through Celite and the filtrate was concentrated in vacuo. The residue was purified by chromatography on silica gel and eluted with 5% ethyl acetate in hexane to yield 2-carboethoxymethoxy-6-hydroxy-3-chloro-5-propylacetophenone.

$^1$H NMR 0.93 (t, J=7Hz, 3H, CH$_3$), 1.30 (t, J=7Hz, 3H, CH$_3$, 1.63 (sextet, J=7Hz, 2H, CH$_2$), 2.57 (t, J=7 Hz 2H CH$_2$). 2.77 (s, 3H, CH$_3$). CH$_2$),4.27 (g, J=7 Hz, 2H, CH$_2$O), 4.73 (s, 2H, CH$_2$), 7.23 (s, 1H, proton ortho to chloro),12.50 (s, 1H, OH).

(c) Preparation of 2-carboethoxy-3-methyl-4-hydroxy-5-propyl-7-chlorobenzofuran.

To a solution of 2-carboethoxymethoxy-6-hydroxy-3-chloro-5-propylacetophenone (43 gm; 0.136 mole) in freshly distilled absolute ethanol (1.2 liter) was brought to reflux and a 1M solution of sodium ethoxide (273 mL; 0.273 mole) was added rapidly. The reaction mixture was refluxed for a period of 1 hour. It was cooled to room temperature and poured into 0.5N hydrochloric acid and extracted with ethylacetate. The organic phase was dried (Na$_2$SO$_4$), and concentrated in vacuo. The residue was chromatographed on silica gel and eluted with 15% ethylacetate in hexane to yield 22.0 gm of 2-carboethoxy-3-methyl-4-hydroxy-5-propyl-7-chloro benzofuran; m.p.: 165°–166°.

$^1$H NMR 1.00 (t, J=7 Hz, 3H, CH$_3$), 1.25 (t, J=7Hz, 3H, CH$_3$, 1.63 (sextet, J=7 Hz, 2H, CH$_2$), 2.57 (t, J=7 Hz, 2H, CH$_2$), 2.76 (s, 3H, CH$_3$), CH$_2$),4.43 (g, J=7 Hz, 2H, CH$_2$O), 5.19 (s, 1H, OH), 7.15 (s, 1H, proton ortho to chloro), 5.19 (s, 1H, OH).

3-methyl-4-hydroxy-5-propyl-7-chlorobenzo furan was also obtained; m.p.: 49–50° C.

$^1$H NMR 0.97 {t, J=7 Hz, 3H, CH$_3$), 1.60 (sextet, J=7 Hz, 2H, CH$_2$), 2.32 (s, 3H, CH$_3$), CH$_2$), 2.50 (t, J=7 Hz, 2H, CH$_2$), 4.97 (s, 1H, OH), 6.93 (s, 1H, proton ortho to chloro), 7.20 (s, 1H, H2).

Anal. Calcd for C$_{12}$H$_{13}$ClO$_2$: C, 64.58; H, 6.20; Cl, 15.72. Found: C, 64.14: H, 5.79; Cl, 15.81.

(d) Preparation of 3-methyl-4-hydroxy-5-propyl-7-chlorobenzofuran carboxylic acid To a solution of 2-carboethoxy-3-methyl-4-hydroxy-5-propyl-7-chlorobenzofuran (22 gm, 0.074 mole) in methanol (1.2 liter) was added 2N sodium hydroxide (120 mL) and the resulting solution was refluxed for a period of 6 hours. The reaction mixture was concentrated in vacuo. The residue was acidified with 3N hydrochloric acid and then extracted with ethylacetate. The organic phase was dried (Na$_2$SO$_4$), concentrated in vacuo, and 3-methyl-4-hydroxy-5-propyl-7-chlorobenzofurancarboxylic acid (17 gm; 88%) was isolated by filtering the solid after suspending in hexane; m.p.: 200°–203° C.

$^1$H NMR 0.97 (t, J=7 Hz, 3H, CH$_3$), 1.60 (sextet, J=7 Hz, 2H, CH$_2$), 2.60 (t, J=7 Hz, 2H, CH$_2$), 2.80 (s, 3H, CH$_3$), 7.33 (s, 1H, proton ortho to chloro), 7.60 (s, 1H, OH).

(e) Preparation of 3-methyl-4-hydroxy-5-propyl-7-chlorobenzofuran

A mixture of 3-methyl-4-hydroxy-5-propyl--7-chlorobenzofuran carboxylic acid (0.93 gm; 3.7 mmoles), toluene (25 mL), 6N hydrochloric acid (20 mL), 10N HCl (100 mL) and acetic acid (30 ml) was refluxed for a period of 18 hours. The two phases were separated and the organic phase was dried (Na$_2$SO$_4$), and concentrated in vacuo to yield 3-methyl-4-hydroxy-5-propyl-7-chlorobenzofuran (0.62 gm; 80%), identical to the product obtained from the cyclisation reaction described above in Step C.

(f) Preparation of 2-(p-methoxybenzoyl)-3-methyl 4-(p-methoxybenzoyloxy)-5-propyl-7-chlorobenzofuran A solution of p-anisoyl chloride (3.5 gm; 20.5mmoles) in ethylene dichloride (10 mL) was added slowly to a cooled suspension of aluminium chloride (4.0 gm; 30mmoles) in ethylene dichloride (100 mL). After stirring for a period of 10 minutes, 3-methyl-4-hydroxy-5-propyl-7-chlorobenzofuran (1.14 gm; 5 mmoles) in dichloroethylene (5 mL) was added over a period of 2 minutes. The reaction mixture was stirred at room temperature for 1 hour. It was cooled with an ice bath and ice was added slowly. When the vigorous reaction subsided, the organic layer was separatd and the agueous phase was extracted with methylene chloride. The organic phases were combined, dried ($Na_2SO_4$), and concentrated in vacuo. The residue was chromatographed on silica gel and eluted with 10% ethylacetate in hexane to yield 1.92 gm (78%) of 2-(p-methoxybenzoyl)-3-methyl-4-(p-methoxybenzoyloxy)5-propyl-7-chlorobenzofuran, mp.103°–105° C.

$^1$H NMR 0.97 (t, J=7 Hz, 3H, $CH_3$), 1.63 (sextet, J=7 Hz, 2H, $CH_2$), 2.55 (s, 3H, $CH_3$), 2.63 (t, J=7 Hz, 2H, $CH_2$). 3.93 (s, 6H, $CH_3$). 7.07 (d. J=9Hz. lH proton ortho to methoxy). 7.13 (d, J=9Hz. 1H, proton ortho to methoxy), 8.23 (d, J=9 Hz, 1H, proton ortho to methoxy), 7.27 (d, J=9 Hz, 1H, proton ortho to methoxy).

Anal. Calcd for $C_{20}H_{21}ClO_3$: C, 69.66; H, 6.13; Cl, 10.28. Found: C, 69.80: H, 6.18; Cl, 10.23.

(g) Preparation of 2-(p-methoxybenzyl)-3-methyl-4-hydroxy-5-propyl-7-chlorobenzofuran To an ice cold suspension of aluminium chloride (467 mg, 3.5mmoles) in ether (100 mL) was added slowly lithium aluminium hydride (570 mg, 15 mmoles). After stirring for a period of 10 minutes, 2-(p-methoxybenzyl)-3-methyl-4-hydroxy-5-propyl-7-chlorobenzofuran (491 mg, 1mmole) in ether (10 mL) was added over a period of 2 minutes. The reaction mixture was stirred at room temperature for 10 minutes. It was cooled with an ice-bath and ice was added slowly. When the vigorous reaction subsided, the organic layer was separated and the agueous phase was extracted with ether. The organic phases were combined, washed with brine, dried ($Na_2SO_4$), and concentrated in vacuo. The residue was chromatographed on silica gel and eluted with 10% ethyl acetate in hexane to yield 0.30 gm (87%) of 2-(p-methoxybenzoyl)-3-methyl-4-hydroxy-5-propyl-7-chlorobenzofuran, mp. 103–105 C.

$^1$H NMR 1.00 (t, J=7 Hz, 3H, $CH_3$), 1.64 (sextet, J=7 Hz, 2H, $CH_2$), 2.39 (s, 3H, $CH_3$), 2.57 (t, J=7 Hz, 2H, $CH_2$), 3.79 (s, 6H, $CH_3$), 4.03 (s, 2H, $CH_2$), 6.84 (d, J=9 Hz, 1H, proton ortho to methoxy), 6.93 (s, 1H, proton ortho to chloro), 7.18 (d, J=9 Hz, 1H, proton meta to methoxy).

Anal. Calcd for $C_{20}H_{21}ClO_3$: C, 69.66; H, 6.13; Cl, 10.28. Found: C, 69.80: H, 6.18; Cl, 10.23.

Following the procedure of Example 23, step (e), the compounds of Table 23-1 were prepared from the appropriate precursor acids described in U.S. Ser. No. 661,645, filed October 17, 1984, a CIP of which has now issued as U.S.Pat. No. 4,663,347.

TABLE 23-1

| R1 | R2 | R3 | X | Y | Y1 | M.P. (°C.) |
|---|---|---|---|---|---|---|
| Me | H | 5,6-$OCH_2O$ | O | H | H | 48–50 |
| Me | H | 4-OMe | O | 7-Pr | H | OIL |
| Me | H | 7-OH | O | H | H | 90–91 |
| Me | H | 4-OH | O | 7-Pr | H | 65–66 |
| Me | H | 5-OH | O | H | H | 84–5 |
| Me | H | 4-OH | O | 5-allyl | H | OIL |
| Pr | H | 4-OH | O | H | H | 35–36 |
| Pr | H | 4-allyl | O | H | H | OIL |
| Pr | H | 4-OH | O | 5-allyl | H | OIL |
| Me | H | 5-Oallyl | O | H | H | OIL |
| Me | H | 5-OH | O | 4-allyl | H | 65–67 |
| Me | H | 5-OH | O | 4-Pr | H | 83–85 |
| Me | H | 4-OH | O | 5-Pr | H | 35–36 |
| $C_6H_5$ | H | 4-OH | O | H | H | OIL |
| Me | H | 4-OH | O | H | H | 110–112 |

EXAMPLE 24

2-(p-methoxybenzyl)-3-methyl-5-hydroxybenzofuran (a) Preparation of 2-(p-methoxybenzoyl)-3-methyl-5-(p-methoxyphenacyloxy)-benzofuran A mixture of 2,5-dihydroxyacetophenone (2.78 gm; 18.3mmoles), potassium carbonate (5.06 gm; 36.6 mmoles) and p-methoxyphenacyl bromide (8.4 gm, 36.8 mmoles) in acetone (100 mL) was refluxed for a period of 18 hours. The reaction mixture was cooled, filtered through Celite, and concentrated in vacuo. The residue was taken up in a minimum volume of acetone and the solution was left to crystallize. The crystals were filtered, washed with cold ethylacetate, and air-dried to yield 4.0 gm (51%) of 2-(p-methoxybenzoyl)-3-methyl 5-(p-methoxyphenacyloxy)-benzofuran, mp. 155°–157° C.

$^1$H NMR 2.60 (s, 3H, $CH_3$), 3.93 (s, 6H, $CH_3$), 5.30 (s, 2H, $CH_2$), 7.00 (m, 4H, protons ortho to metooxyl), 7.20 (m, 2H, H6 and H7), 8.10 (t, 2H, J=9Hz, protons meta to methoxy).

Anal. Calcd for $C_{11}H_{12}O_3$: C, 72.54; H, 5.15. Found: C, 72.57: H, 5.22.

(b) Preparation of 2-(p-methoxybenzyl)-3-methyl5-hydroxybenzofuran

A mixture of 2-(p-methoxybenzoyl)-3-methyl-5-(p-methoxyphenacyloxy)-benzofuran (5.35· gm, 12.4 mmoles) and zinc dust (5.3 gm) in acetic acid (200 mL) was stirred at room temperature overnight. The solids were filtered off and washed with some ethylacetate. The filtrate was concentrated in vacuo and the residue was chromatographed on silica gel using 20% ethylacetate in hexane as eluent to yield 0.85 gm (26%) of 2-(p-methoxybenzyl)3-methyl5-hydroxybenzofuran, mp. 128°–131° C.

$^1$H NMR 2.17 (s, 3H, $CH_3$), 3.70 (s, 3H, $CH_3$), 3.93 (s, 2H, $CH_2$), 6.90 (m, 7H, aromatic protons)

Anal. Calcd for $C_{17}H_{16}O_3$: C, 76.09; H, 6.01. Found: C, 76.35; H, 6.37.

EXAMPLE 25

2-(p-methoxybenzyl)-3-methyl-4-hydroxy-5-propyl-7-fluorobenzofuran (a) Preparation of 2-hydroxy-6-allyloxyacetophenone A mixture of 2,6-dihydroxyacetophenone (300 gm; 1.97 moles), potassium carbonate (271 gm; 1.97 moles), and allyl bromide (271 mLs; 2.25 moles) in acetone ( 10 liters) was refluxed for a period of 3 hours. The reaction mixture was cooled, filtered through Celite and concentrated in vacuo. The residue was chromatographed on silica gel using toluene as eluent to yield 305 gm (80%) of 2-hydroxy-6-allyloxyacetophenone, mp. 54°–55° C.

$^1$H NMR 2.40 (s, 3H, CH$_3$), 4.57 (d,J=6 Hz, 2H,OCH$_2$), 5.57 (m, 1H, CH), 6.33 (m, 2H, CH$_2$, 6.62 (d, J=9 Hz, 1H, proton ortho to hydroxyl), 6.83 (d,J=9 Hz, 1H, proton ortho to allyloxy), 7.72 (t, J=9 Hz, 1H, proton para to acetyl).

Anal. Calcd for C$_{11}$H$_{12}$O$_3$: C, 68.75; H, 6.25. Found: C, 68.66; H, 6.54.

(b) Preparation of 2,6-dihydroxy-3-allylacetophenone-2-hydroxy-5-allyloxyacetophenone (30 gm; 0.156 mole) was heated under nitrogen at 190° C. for a period of 10 minutes. The mixture was cooled and taken up into carbon tetrachloride to yield 2,6-dihydroxy-3-allylacetophenone, mp 67°–68° C. in guantitative yield.

$^1$H NMR 2.77 (s, 3H, CH$_3$), 3.37 (d,J=6 Hz, 2H,OCH$_2$), 5.37 (m, 1H,CH), 6.00 (m, 2H, CH$_2$, 6.33 (d, J=9 Hz, 1H, proton ortho to hydroxyl), 7.17 (d,J=9 Hz, 1H, proton meta to hydroxy).

Anal. Calcd for C$_{11}$H$_{12}$O$_3$C, 68.75; H, 6.25. Found C, 68.90; H, 6.21.

(c) Preparation of 2,6-dihydroxy-3-propylacetophenone-2,6-dihydroxy-3-allylacetophenone (30 gm; 0.156 mole) dissolved in ethanol (150 mL) was hydrogenated in a Parr apparatus in presence of 5% palladium on carbon. The catalyst was removed by filtration and the filtrate was concentrated to dryness to yield 30 gm of 2,6-dihydroxy-3-propylacetophenone, mp. 76°–78° C.

$^1$H NMR 0.97 (t, J=7 Hz, 3H, CH$_3$), 1.60 (sextet, J=7 Hz, 2H, CH$_2$), 2.53 (t, J=7 Hz, 2H, CH$_2$), 2.73 (s, 3H, CH$_3$), CH$_2$), 6.30 (d, J=9 Hz, 1H, proton ortho to hydroxy), 7.13 (d,J=9 Hz, 1H, proton meta to hydroxy).

Anal. Calcd for C$_{11}$H$_{14}$O$_3$: C, 68.04; H, 7.21. Found: C, 68.05; H, 7.34.

(d) Preparation of 2,6-dihydroxy-3-propyl-5-fluoroacetophenone Method 1.A solution of 2,6-dihydroxy-3-propyl-acetophenone (194 mg; 1mmole) in Freon (fluoro-trichloromethane) (30 mL) was cooled at −78° C. and trifluoromethylhypofluorite was bubbled through the solution slowly, monitoring the reaction by TLC until about half of the material has reacted. The mixture is poured onto a silica gel column and elution with 15% ethylacetate in hexane gave 40 mg of 2,6-dihydroxy 3-propyl-5-fluoroacetophenone.

$^1$H NMR 0.93 (t, J=7 Hz, 3H, CH$_3$), 1.67 (sextet, J=7 Hz, 2H, CH$_2$), 2.57 (t, J=7 Hz, 2H, CH$_2$), 2.80 (s, 3H, CH$_3$), 6.18 (d, J=6 Hz, 1H, OH ortho to fluoro), 7.13 (d, J=11 Hz, 1H, proton ortho to fluoro). Method 2a. Preparation of 2,6-dimethoxy-3-propyl-5-fluoroacetophenone A solution of 2,6-dimethoxy-3-propylacetophenone (21.0 gm; 94.6mmoles) in Freon (30 mL) was cooled at −78° C. and trifluoromethylhypofluorite was bubbled through the solution slowly, monitoring the reaction by TLC until about 75% of the material has reacted. The mixture is poured onto a silica gel column and elution with 15% ethylacetate in hexane gave 11.1 g of 2,6-dimethoxy propyl-5-fluoroacetophenone and 9.0 gm of unreacted 2,6-dimethoxy-3-propylacetophenone.

$^1$H NMR 0.97 (t, J=7 Hz, 3H, CH$_3$), 1.67 (sextet, J=7 Hz, 2H, CH$_2$), 2.50 (t, J=7 Hz, 2H, CH$_2$), 2.50 (s, 3H, CH$_3$), 3.70 (s, 3H, CH$_3$) 3.82 (d, J=3 Hz, 3H, CHJ3), 6.90 (d, J=11 Hz, 1H, proton ortho to fluoro).
2b. Preparation of 2,6-dihydroxy-3-propyl-5-fluoroacetophenone To a solution of 2,6-dimethoxy-3-propyl-5-fluoroacetophenone (3.0 gm; 12.5mmoles) in methylene chloride (32 mL) cooled to −78° C., was added dropwise over a period of 1 hour a 1M solution of boron tribromide (56 mL; 56mmoles) The temperature was allowed to rise to room temperature and the reaction mixture was stirred for 3 hours. It was then cooled to −78° C. and methanol (20 mL) was added rapidly. The resulting solution was poured in water, the phases were separated and the agueous phase was extracted with methylene chloride. The organic phases were combined, washed with brine, dried (Na$_2$SO$_4$), and concentrated in vacuo. The residue was chromatographed on silica gel and eluted with 7% ethylacetate in hexane to yield 1.5 gm (58%) of 2,6-dihydroxy-3-propyl-5-fluoroacetophenone.

$^1$H NMR 0.93 (t, J=7 Hz, 3H, CH$_3$), 1.63 (sextet, J=7 Hz, 2H, CH$_2$), 2.50 (t, J=7 Hz, 2H, CH$_2$), 2.73 (s, 3H, CH$_3$), 5.93 (d, J=6 Hz, 1H, OH), 7.10 (d, J=11 Hz, 1H, proton ortho to fluoro).

(e) Preparation of 2-carboethoxymethoxy-6-hydroxy-3-propyl-5-fluoroacetophenone

A mixture of 2,6-dihydroxy-5-fluoro-3-propylacetophenone (3.5 gm, 16.5mmoles), ethyl bromoacetate (2.0 ml; 18.1mmoles) and potassium carbonate (2.27 gm; 16.5mmoles) in acetone (1 liter) was refluxed for a period of 0.5 hour. The reaction mixture was filtered through Celite and the filtrate was concentrated in vacuo to yield a residue that purified by chromatography on silica gel. Elution with 10 % ethyl acetate in hexane yielded 4.2 gm (86%) of 2-carboethoxymethoxy 6-hydroxy 3-propyl-5-fluoroacetophenone.

$^1$H NMR 0.93 (t, J=7 Hz, 3H, CH$_3$), 1.27 (t, J=7Hz, 3H, CH$_3$, $_{1.63}$ (sextet, J=7 Hz, 2H, CH$_2$), 2.53 (t, J=7 Hz, 2H, CH$_2$), 2.77 (s, 3H, CH$_3$), CH$_2$),4.20 (g, J=7 Hz, 2H, CH$_2$O), 4.80 (s, 2H, CH$_2$), 7.03 (d, J=11Hz, 1H, proton ortho to fluoro).

(f) Preparation of 2-carboethoxy-3-methyl-4-hydroxy-5-propyl-7-fluorobenzofuran.

A solution of 2-carboethoxy-3-methyl-4-hydroxy-5-propyl-7-fluorobenzofuran (15 gm; 50.0 mmoles) in freshly-distilled absolute ethanol (0.5 liter) was brought to reflux and a 1M solution of sodium ethoxide (100 mL; 100mmoles) was added rapidly. The reaction mixture was refluxed for a period of 1 hour. It was cooled to room temperature and poured into 0.5N hydrochloric acid and extracted with ethyl acetate. The organic phase was dried (Na$_2$SO$_4$), concentrated in vacuo, and the residue was chromatographed on silica gel. Elution with 10% ethylacetate in hexane yielded 9.0 gm of 2-carboethoxy-3-methyl-4-hydroxy-5-propyl-7-fluorobenzofuran.

$^1$H NMR 1.00 (t, J=7 Hz, 3H, CH$_3$), 1.43 (t, J=7Hz, 3H, CH$_3$, $_{1.63}$ (sextet, J=7 Hz, 2H, CH$_2$), 2.57 (t, J=7 Hz, 2H, CH$_2$), 2.80 (s, 3H, CH$_3$), CH$_2$),4.47 (g, J=7 Hz, 2H, CH₂O), 4.97 (s, 1H, OH), 6.90 (s, 1H, proton ortho to fluoro).

3-methyl-4-hydroxy-5-peopyl-7-fluorobenzofuran, (1.0 gm) mp. 53°-54° C. was also obtained.

¹H NMR 1.00 (t, J=7 Hz, 3H, CH₃), 1.63 (sextet, J=7 Hz, 2H, CH₂), 2.40 (d,J=2 Hz, 3H, CH₃), CH₂), 2.57 (t, J=7 Hz, 2H, CH₂), 4.73 (s, 1H, OH), 6.73 (d,J=11 Hz, 1H, proton ortho to fluoro), 7.28 (d,J=2Hz, 1H, H2).

Anal. Calcd for $C_{12}H_{13}ClO_2$: C, 69.23; H, 6.25; F, 9.13. Found: C, 64.14; H, 5.79; Cl, 15.81.

(g) Preparation of 3-methyl-4-hydroxy-5-propyl-7-fluorobenzofurancarboxylic acid To a solution of 2-carboethoxy-3-methyl-4-hydroxy-5-propyl-7-fluorobenzofuran (1.0 gm, 3.6 mmoles) in methanol (100 mL) was added 2N sodium hydroxide (10 mL) and the resulting solution was refluxed for a period of 4.5 hours. The reaction mixture was concentrated in vacuo. The residue was acidified with 3N hydrochloric acid and then extracted with ethylacetate. The organic phase was dried (Na₂SO₄), concentrated in vacuo, and 3 methyl-4 hydroxy 5 propyl 7 -fluorobenzofuran-carboxylic acid (0.79 gm; 88%) was isolated by filtering the solid after suspending in hexane.

¹H NMR 0.97 (t, J=7 Hz, 3H, CH₃), 1.60 (sextet, J=7 Hz, 2H, CH₂), 2.67 (t, J=7 Hz, 2H, CH₂), 2.80 (s, 3H, CH₃), 6.90 (d,J=11 Hz, 1H, proton ortho to fluoro), 7.00 (s, 2H, OH).

(h) Preparation of 3-methyl-4-hydroxy-5-propyl-7-fluorobenzofuran

A mixture of 3-methyl-4-hydroxy-5-propyl-7-fluorobenzofurancarboxylic acid (0.10 gm; 0.4mmoles) and copper(20 mg) in guinoline (50 mL) was refluxed for a period of 2.5 hours. The two phases were separated and the organic phase was dried (Na₂SO₄), and concentrated in vacuo. The residue was purified by preparative TLC and eluted with 5% ethylacetate in hexane to yield 3-methyl-4-hydroxy-5-propyl-7-fluorobenzofuran (62 mg ; 75%), identical to the product obtained from the cyclisation reaction described above in step f.

(i) Preparation of 2-(p-methoxybenzoyl)-3-methyl-4-(p-methoxybenzoyloxy)-5-propyl-7-fluorobynzofuran A solution of p-anisoyl chloride (2.70 gm; 15.5mmoles) in ethylene dichloride (10 mL) was added slowly to a cooled suspension of aluminium chloride (3.0 gm; 21.8mmoles) in ethylene dichloride (100 mL). After stirring for a period of 10 minutes, 3-methyl-4-hydroxy-5-propyl-7-fluorobenzofuran (0.79 gm; 3.8mmoles) in dichloroethylene (5 mL) was added over a period of 2 minutes. The reaction mixture was stirred at room temperature for 1 hour. It was cooled with an ice-bath and ice was added slowly. When the vigorous reaction subsided, the organic layer was separated and the agueous phase was extracted with methylene chloride. The organic phases were combined, dried (Na₂SO₄), and concentrated in vacuo. The residue was chromatographed on silica gel and eluted with 10% ethylacetate in hexane to yield 1.18 gm (63%) of 2-(p-methoxybenzoyl)-3-methyl-4-(p-methoxybenzoyloxy)-5-propyl-7-fluorobenzofuran.

¹H NMR 0.90 (t, J=7 Hz, 3H, CH₃), 1.63 (sextet, J=7 Hz, 2H, CH₂), 2.55 (s, 3H, CH₃), 2.63 (t, J=7 Hz, 2H, CH₂), 3.90 (s, 6H, CH₃), 6.97 (d, J=9 Hz, 1H, proton ortho to methoxy), 7.03 (d, J=9Hz, 1H, proton ortho to methoxy), 8.13 (d, J=9 Hz, 1H, proton ortho to methoxy), 8.23 (d, J=9 Hz, 1H, proton ortho to methoxy).

Anal Calcd for $C_{20}H_{21}ClO_3$: C, 69.66; H, 6.13; F, 10.28. Found: C, 69.80; H, 6.18; F, 10.23.

(j) Preparation of 2-(p-methoxybenzyl)-3-methyl-4-hydroxy-5-propyl-7-fluorobenzofuran To an ice cold suspension of aluminium chloride (1.14 gm, 8.5 mmoles) in ether (100 mL) was added slowly lithium aluminium hydride (1.39 gm, 36 mmoles). After stirring for a period of 10 minutes, 2-(p-methoxybenzyl)-3-methyl-4-hydroxy-5-propyl-7-fluorobenzofuran (1.18 gm, 2.48mmoles) in ether (10mL) was added over a period of 2 minutes. The reaction mixture was stirred at room temperature for 10minutes. It was cooled with an ice-bath and ice was added slowly. When the vigorous reaction subsided, the organic layer was separated and the agueous phase was extracted with ether. The organic phases were combined, washed with brine, dried (Na₂SO₄), and concentrated in vacuo. The residue was chromatographed on silica gel and eluted with 10% ethyl acetate in hexane to yield 0.58 gm (71%) of 2-(p-methoxybenzyl)-3-methyl-4-hydroxy-5-propyl-7-fluorobenzofuran.

¹H NMR 0.98 (t, J=7 Hz, 3H, CH₃), 1.66 (sextet, J=7 Hz, 2H, CH₂), 2.39 (s, 3H, CH₃), 2.55 (t, J=7 Hz, 2H, CH₂), 3.78 (s, 6H, CH₃), 4.00 (s, 2H, CH₂), 6.67 (d, J=11 Hz, 1H, proton ortho to fluoro), 6.84 (d, 2H, proton ortho to methoxy), 7.16 (d, J=9 Hz, 1H, proton meta to methoxy).

Anal. Calcd for $C_{20}H_{21}ClO_3$: C, 73.15; H, 6.44; F, 5 78. Found: C, 73.71; H, 6.45; F, 5.09.

EXAMPLE 26
2-(p-methoxybenzyl)-3-methyl-4-hydroxy-7-propylbenzofuran

(a) Preparation of 2-hydroxy-3-propyl-6-benzyloxyacetophenone

A mixture of 2,6-dihydroxy-3-propylacetophenone (5.5 gm; 28.3mmoles), potassium carbonate (3.9 gm; 31mmoles) and benzyl bromide (4.3 gm; 31 mmoles) in acetone (10 liters) was refluxed for a period of twenty hours. The reaction mixture was cooled, filtered through Celite, and concentrated in vacuo. The residue was chromatographed on silica gel using 10% ethylacetate in hexane as eluent to yield 5.6 gm (70%) of 2-hydroxy-3-propyl-6-benzyloxyacetophenone.

¹H NMR 0.93 (t, 3H, J=7 Hz, CH₃), 1.60 (sextet, 2H, J=7 Hz, CH₂), 2.60 (t, 2H, J=7 Hz, CH₂), 2.67 (s, 3H, CH₃), 5.13 (s, 2H, CH₂), 6.40 (d, 1H, J=9Hz, H5), 7.23 (d, 1H, J=9 Hz, H4), 7.40 (s, 5H, phenyl protons).

(b) Preparation of 2-(p-methoxybenzoyl)-3-methyl-4-benzyloxy-7-propylbenzofuran.

A mixture of 2-hydroxy-3-propyl-6-benzyloxyacetophenone (1.0 gm; 3.52 mmoles), potassium carbonate (0.81 gm; 3.82 mmoles) and p-methoxyphenacyl bromide (0.54 gm, 3.80 mmoles) in methylethylketone (40 mL) was refluxed for a period of 20 hours. The reaction mixture was cooled, filtered through Celite, and concentrated in vacuo. The residue was chromatographed on silica gel using 10% ethylacetate in hexane as eluent to yield 0.74 gm (51%) of 2-(p-methoxybenzoyl)-3-methyl-4-benzyloxy-7-propylbenzofuran.

$^1$H NMR 0.93 (t, 3H, J=7 Hz, CH$_3$), 1.67 (sextet, 2H, J=7 Hz, CH$_2$), 2.75 (s, 3H, CH$_3$), 2.75 (t, 2H, J=7 Hz, CH$_2$), 3.83 (s, 3H, CH$_3$), 5.13 (s, 2H, CH$_2$), 6.60 (d, 1H, J=9 Hz, H5), 6.93 (d, 2H, J=9 Hz, protons ortho to methoxy), 7.10 (d, 1H, J=9 Hz, H6), 7.40 (s, 5H, phenyl protons), 8.10 (d, 2H, J=9 Hz, protons meta to methoxy).

(c) Preparation of 2-(p-methoxybenzyl)-3-methyl-4-hydroxy-7-propylbenzofuran

A mixture of 2-(p-methoxybenzoyl)-3-methyl-4-benzyloxy-7-propylbenzofuran (0.10 gm, 0.24 mmole) in ethanol was hydrogenated in a Parr hydrogenator in the presence of 10% palladium on charcoal at 40 psi for a period of 7 hours. The catalyst was filtered off, washed with some ethanol, and the filtrate was concentrated in vacuo to yield 2-(p-methoxybenzyl)-3-methyl-4-hydroxy-7-propylbenzofuran.

$^1$H NMR 0.90 (t, 3H, J=7 Hz, CH$_3$), 1.63 (sextet, 2H, J=7 Hz, CH$_2$), 2.33 (s, 3H, CH$_3$), 2.70 (t, 2H, J=7 Hz, CH$_2$), 3.73 (s, 3H, CH$_3$), 3.93 (s, 2H, CH$_2$), 4.97 (s, 1H, OH), 6.37 (d, 1H, J=9 Hz, H5), 6.78 (d, 2H, J=9 Hz, protons ortho to methoxy), (d, 1H, J=9 Hz, H6), 7.17 (d, 2H, J=9 Hz, protons meta to methoxy).

EXAMPLE 27

2-(p-methoxybenzyl)-3-methyl-4-propyl-5-hydroxybenzofuran (a) Preparation of 2-(p-methoxybenzoyl)-3-methyl-5-allyloxybenzofuran.

A mixture of 2-hydroxy-5-allyloxyacetophenone (7.7 gm; 40.0 mmoles), potassium carbonate (6.90 gm; 50.0 mmoles) and p-methoxyphenacyl bromide (11.4 gm, 50.0 mmoles) in acetone (100 mL) was refluxed for a period of 22 hours. The reaction mixture was cooled, filtered through Celite, and concentrated in vacuo. The residue was chromatographed on silica gel using 50% ethylacetate in hexane as eluent to yield 7.2 gm (56%) of 2-(p-methoxybenzoyl)-3-methyl-5-allyloxybenzofuran, mp. 74°-76° C.

$^1$H NMR 2.60 (s, 3H, CH$_3$), 3.88 (s, 3H, CH$_3$), 4.60 (m, 2H, CH2), 5.40 (m, 2H, CH$_2$) 6.10 (m, 1H, CH), 7.10 (m, 4H, protons ortho to methoxy, H4 and H6), 7.43 (1H, J=9 Hz, H7), 8.17 (d, 2H, J=9 Hz, protons ortho to methoxy).

(b) Preparation of 2-(p-methoxybenzoyl)-3-methyl-4-allyl-5-hydroxybenzofuran

A mixture of 2-(p-methoxybenzoyl)-3-methyl-5-allyloxybenzofuran (1 gm, 3.10 mmole) in ortho dichlorobenzene (5 mL) was refluxed under nitrogen for a period of 5 hours. On cooling, the product crystallized. It was diluted with hexane, filtered, washed with hexane, and air-dried to yield 870 mg (87%) of 2-(p-methoxybenzoyl)-3-methyl-4-allyl-5-hydroxy-benzofuran, mp. 155°-158° C.

$^1$H NMR 2.68 (s, 3H, CH$_3$), 3.80 (m, 5H, CH$_3$ and CH$_2$), 5.00 (m, 2H, CH$_2$), 6.03 (m, 1H, CH), 6.90 (d, 3H, protons ortho to methoxy and H6), 7.23 (1H, J=9 Hz, H7), 8.03 (d, 2H, J=9 Hz, protons ortho to methoxy).

(c) Preparation of 2-(p-methoxybenzoyl)-3-methyl-4-propyl-5-hydroxybenzofuran

A solution of 2-(p-methoxybenzoyl)-3-methyl-4-allyl-5-hydroxybenzofuran (3 gm, 9.3 mmoles) in ethanol (150 mL) was hydrogenated in a Parr hydrogenator in the presence of 10% palladium on charcoal at 40 psi for a period of 3 hours. The catalyst was filtered off, washed with some ethanol, and the filtrate was concentrated in vacuo. The residue was recrystallized from hexane to yield (1.1 gm, 38%) of 2-(p-methoxybenzoyl)-3-methyl-4-propyl-5-hydroxybenzofuran, mp. 91°-93° C.

$^1$H NMR 1.00 (t, 3H, J=7 Hz, CH$_3$), 1.63 (sextet, 2H, J=7 Hz, CH$_2$), 2.33 (s, 3H, CH$_3$), 2.87 (t, 2H, J=7 Hz, CH$_2$), 3.73 (s, 3H, CH$_3$), 3.93 (s, 2H, CH$_2$), 4.37 (s, 1H, OH), 6.63 (d, 1H, J=9 Hz, H6), 6.78 (d, 2H, J=9 Hz, protons ortho to methoxy), 7.07 (d, 1H, J=9 Hz, H7), 7.13 (d, 2H, protons meta to methoxy).

EXAMPLE 28

2-(p-methoxybenzyl)-3-methyl-4-hydroxybenzofuran (a) Preparation of 2-(p-methoxybenzoyl)-3-methyl-4-hydroxybenzofuran A mixture of 2,6-dihydroxyacetophenone (5.35 gm; 35.0 mmoles), potassium carbonate (4.83 gm; 35.0 mmoles), and p-methoxyphenacylbromide (8.05 gm; 35.0 mmoles) in acetone (150 mL) was refluxed for a period of 22 hours. The reaction mixture was cooled, filtered through Celite, and concentrated in vacuo. The residue was dissolved in methylene chloride and washed with 1N sodium hydroxide. The aqueous phase was then acidified with 20% citric acid. The solid was filtered, washed with water, and air-dried to yield 6.5 gm (65%) of 2-(p-methoxybenzoyl)-3-methyl-4-hydroxybenzofuran, mp. 192°-195° C.

$^1$H NMR 2.80 (s, 3H, CH$_3$), 3.90 (s, 3H, CH$_3$), 6.73 (d, 1H, J=9 Hz, H5), 7.07 (m, 4H, protons ortho to methoxy, H5 and H6 ), 8.13 (d, J=9 Hz, 2H, proton ortho to carbonyl).

(b) Preparation of 2-(p-methoxybenzyl)-3-methyl-4-hydroxybenzofuran

A mixture of 2-(p-methoxybenzoyl)-3-methyl-4-hydroxybenzofuran (2.0 gm; 7.0 mmoles), 99% hydrazine (50 mL) and potassium hydroxide (2.7 gm; 49 mmoles) in ethylene glycol (50 mL) was heated at 140° C. for a period of 2.5 hours and at 195° C. for one hour. The reaction mixture was cooled, poured in water, and extracted with ethylacetate. The organic phase was washed with 20% citric acid, with brine, dried (Na$_2$SO$_4$), and concentrated in vacuo. The residue was chromatographed on silica gel using 20% ethylacetate in hexane as eluent to yield 700 gm (37%) of 2-(p-methoxybenzyl)-3-methyl-4-hydroxybenzofuran, mp.130°-133° C.

$^1$H NMR 2.40 (s, 3H, CH$_3$), 3.80 (s, 3H, CH$_3$), 4.00 (s, 2H, CH$_2$), 5.04 (s, 1H, OH), 6.48 (d, 2H, J=9 Hz, H5), 6.88 (m, 4H, protons ortho to methoxy, H6 and H7), 7.15 (d, J=9 Hz, 2H, proton meta to methoxy).

Anal. Calcd for C$_{17}$H$_{16}$O$_3$: C, 76.09; H, 6.01; Found: C, 76.21; H, 6.39.

EXAMPLE 29

2-(p-methoxybenzyl)-3-methyl-4-hydroxy-5-propylbenzofuran (a) Preparation of 2-(p-methoxybenzoyl)-3-methyl-4-allyloxybenzofuran A mixture of 2-(p-methoxybenzoyl)-3-methyl-4-hydroxybenzofuran (0.60 gm; 2.2 mmoles), potassium carbonate (0.83 gm; 6.0 mmoles) and allyl bromide (0.73 gm; 6.0 mmoles) in acetone (25 mL) was refluxed for a period of 22 hours. The reaction mixture was cooled, filtered through Celite, and concentrated in vacuo. The residue was chromatographed on silica gel using 15% ethylacetate in hexane as eluent to yield 2-(p-methoxybenzoyl)-3-methyl-4-allyloxybenzofuran.

$^1$H NMR 2.40 (s, 3H, CH$_3$), 3.80 (s, 3H, CH$_3$), 4.00 (s, 2H, CH$_2$), 4.64 (m, 2H, CH$_2$), 5.40 (m, 2H, ch2), 6.12 (m, 1H, CH), 6.60 (d, 1H, J=9 Hz, H5), 6.84 (d, 2H, J=9 Hz, protons ortho to methoxy), 7.00 (d, 1H, J=9 Hz, H7), 7.06 (d, 1H, J=9 Hz, H6), 7.15 (d, J=9 Hz, 2H, proton meta to methoxy).

Anal. Calcd for C$_{20}$H$_{20}$O$_3$: C, 77.89; H, 6.53; Found: C, 77.87; H, 6.76.

(b) Preparation of 2-(p-methoxybenzoyl)-3-methyl-4-hydroxy-5-allylbenzofuran

A solution of 2-(p-methoxybenzoyl)-3-methyl-4-allyloxybenzofuran (0.7 gm; 2.2 mmoles) in orthodichlorobenzene (3 mL) was refluxed under nitrogen for a period of 4 hours. The mixture was cooled to room temperature and purified by chromatography on silica gel using 15% ethylacetate in hexane as eluent to yield 650 mg (93%) of 2-(p-methoxyenzoyl)-3-methyl-4-hydroxy-5-allylbenzofuran, mp. 48°–50° C.

$^1$H NMR 2.41 (s, 3H, CH$_3$), 3.44 (m, 2H, CH$_2$), 3.78 (s, 3H, CH$_3$), 4.00 (s, 2H, CH$_2$), 5.23 (m, 2H, CH$_2$), 6.03 (m, 1H, CH), 6.84 (d, 2H, J=9 Hz, protons ortho to methoxy), 6.88 (s, 2H,H6 and H7), 7.15 (d, J=9Hz, 2H, proton meta to methoxy).

Anal. Calcd for C$_{20}$H$_{20}$O$_3$: C, 77.89; H, 6.53; Found: C, 77.80; H, 6.81.

(c) Preparation of 2-(p-methoxybenzyl)-3-methyl-4-hydroxy-5-propylbenzofuran.

A solution of 2-(p-methoxybenzoyl)-3-methyl-4-hydroxy-5-allylbenzofuran (40 mg) in ethanol (50 mL) was hydrogenated in a Parr hydrogenator in the presence of 10% palladium on charcoal at 40 psi. The catalyst was filtered and the filtrate was concentrated to dryness to yield 2-(p-methoxybenzyl)-3-methyl-4-hydroxy-5-propylbenzofuran, identical to the product prepared by the route described in Example 1.

EXAMPLE 30

2-benzyl-3-methyl-4-hydroxy-5-propyl-7-chlorobenzofuran (a) Preparation of 2-benzoyl-3-methyl-4-benzoyloxy-5-propyl-7-chlorobenzofuran A solution of benzoyl chloride (3.03 gm; 21.6 mmoles) in ethylene dichloride (20 mL) was added slowly to a cooled suspension of aluminium chloride (5.8 gm; 43 mmoles) in ethylenedichloride (100 mL).

After stirring for a period of 10 minutes, 3-methyl-4-hydroxy-5-propyl-7-chlorobenzofuran (1.62 gm; 7.2 mmoles) in dichloroethylene (20 mL) was added over a period of 2 minutes. The reaction mixture was stirred at room temperature for 1 hour. It was cooled with an ice-bath and ice was added slowly. When the vigorous reaction subsided, the organic layer was separated and the aqueous phase was extracted with methylene chloride. The orqanic phases were combined, dried (Na$_2$SO$_4$), and concentrated in vacuo. The residue was chromatographed on silica gel and eluted with 10% ethylacetate in hexane to yield 1.18 gm (63%) of 2-benzoyl-3-methyl-4-benzoyloxy-5-propyl-7-chlorobenzofuran, mp. 141°–142° C.

$^1$H NMR 0.93 (t, J=7 Hz, 3H, CH$_3$), 1.63 (sextet, J=7 Hz, 2H, CH$_2$), 2.55 (s, 3H, CH$_3$), 2.60 (t, J=7 Hz, 2H, CH$_2$), 7.33 (s, 1H. H6), 7.50 (m, 6H, meta and para protons of benzoyl group), 8.20 (m, 4H, protons ortho to carbonyl).

Anal. Calcd for C$_{26}$H$_{21}$ClO$_4$: C, 72.13; H, 4.88; Cl, 8.18. Found: C, 71.30; H, 5.05; Cl, 8.37.

(b) Preparation of 2-benzyl-3-methyl-4-hydroxy-5-propyl-7-chlorobenzofuran

To an ice-cold suspension of aluminium chloride (2.50 gm, 18 mmoles) in ether (300 mL) was added slowly lithium aluminium hydride (3.0 gm, 80 mmoles). After stirring for a period of 10 minutes, 2-benzyl-3-methyl-4-hydroxy-5-propyl-7-chlorobenzofuran (2.31 gm, 5.33 mmoles) in ether (10 mL) was added over a period of 2 minutes. The reaction mixture was stirred at room temperature for 10 minutes. It was cooled with an ice bath and ice was added slowly. When the vigorous reaction subsided, the organic layer was separated and the aqueous phase was extracted with ether. The organic phases were combined, washed with brine, dried (Na$_2$SO$_4$), and concentrated in vacuo. The residue was chromatographed on silica gel and eluted with 10% ethylacetate in hexane to yield 1.30 gm (77%) of 2-benzyl-3-methyl-4-hydroxy-5-propyl-7-chlorobenzofuran, mp. 69°–70° C.

$^1$H NMR 0.98 (t, J=7 Hz, 3H, CH$_3$), 1.60 (sextet, J=7 Hz, 2H, CH$_2$), 2.40 (s, 3H, CH$_3$), 2.63 (t, J=7 Hz, 2H, CH$_2$), 4.00 (s, 2H, CH$_2$), 4.80 (s, 1H, OH), 6.90 (s, 1H, H6), 7.23 (s, 5H, phenyl protons).

Anal. Calcd for C$_{19}$H$_{19}$ClO$_2$: C, 72.49; H, 6.08; Cl, 11.26. Found: C, 72.48; H, 6.16; Cl, 11.02.

EXAMPLE 31

2-(p-hydroxybenzyl)-3-methyl-4-hydroxy-5-propyl-7-chlorobenzofuran

To a solution of 2-(p-methoxybenzyl)-3-methyl-4-hydroxy-5-propyl-7-chlorobenzofuran (100 mg, 0.29 mmole) in methylene chloride (5 mL) cooled to −78° C., was added dropwise over a period of 5 minutes a 1M solution of boron tribromide (0.3mL; 0.3 mmole) in methylene chloride. The temperature was allowed to rise to room temperature and the reaction mixture was stirred for 3 hours. It was then cooled to −78° C. and methanol (2 mL) was added rapidly. The resulting solution was poured into water. The phases were separated and the aqueous phase was extracted with methylene chloride. The organic phases were combined, washed with brine, dried (Na$_2$SO$_4$), and concentrated in vacuo. The residue was chromatographed on silica gel and eluted with 15% ethyl acetate in hexane to yield 63 mg gm (66%) of 2-(p-hydroxybenzyl)-3-methyl-4-hydroxy-5-propyl-7-chlorobenzofuran, mp. 142°–143° C.

EXAMPLE 32

2-(p-bromobenzyl)-3-methyl-4-hydroxy-5-propyl-7-chlorobenzofuran (a) Preparation of 2-(p-bromobenzoyl)-3-methyl-4-(p-bromobenzoyloxy)-5-propyl-7-chlorobenzofuran A solution of p-bromobenzoyl chloride (1.1 gm; 5.0 mmoles) in ethylene dichloride (5 mL) was added slowly to a cooled suspension of aluminium chloride (3.3 gm; 25 mmoles) in ethylene dichloride (75 mL). After stirring for a period of 10 minutes, 3-methyl-4-hydroxy-5-propyl-7-chlorobenzofuran (0.95 gm; 4.2 mmoles) in dichloroethylene (20 mL) was added over a period of 2 minutes. The reaction mixture was stirred at room temperature for 1 hour. It was cooled with an ice-bath and ice was added slowly. When the vigorous reaction subsided, the organic layer was separated and the aqueous phase was extracted with methylene chloride. The organic phases were combined, dried ($Na_2SO_4$), and concentrated in vacuo. The residue was chromatographed on silica gel and eluted with 10% ethylacetate in hexane to yield 260 mg gm of 2-(p-bromobenzoyl-3-methyl-4-(p-bromobenzoyloxy)-5-propyl-7-chlorobenzofuran.

$^1$H NMR 0.97 (t, J=7 Hz, 3H, $CH_3$), 1.70 (sextet, J=7 Hz, 2H, $CH_2$), 2.60 (s, 3H, $CH_3$), 2.63 (t, J=7 Hz, 2H, $CH_2$), 7.43 (s, 1H. H6), 7.80 (m, 4H, protons meta to carbonyl), 8.20 (m, 4H, protons ortho to carbonyl).

(b) Preparation of 2-(p-bromobenzyl)-3-methyl-4-hydroxy-5-propyl-7-chlorobenzofuran To an ice-cold suspension of aluminium chloride (0.5 gm, 3.6 mmoles) in ether (100 mL) was added slowly lithium aluminium hydride (1.0 gm, 26.7 mmoles). After stirring for a period of 10 minutes, 2-(p-bromobenzyl)-3-methyl-4-(p-bromobenzoyloxy-5-propyl-7 chlorobenzofuran (0.22 gm, 0.37 mmole) in ether (10 mL) was added over a period of 2 minutes. The reaction mixture was stirred at room temperature for 10 minutes. It was cooled with an ice-bath and ice was added slowly. When the vigorous reaction subsided, the organic layer was separated and the aqueous phase was extracted with ether. The organic phases were combined, washed with brine, dried ($Na_2SO_4$), and concentrated in vacuo. The residue was chromatographed on silica gel and eluted with 10% ethyl acetate in hexane to yield 178 mg (97%) of 2-benzyl-3-methyl-4-hydroxy-5-propyl-7-chlorobenzofuran.

$^1$H NMR 0.98 (t, J=7 Hz, 3H, $CH_3$), 1.57 (sextet, J=7 Hz, 2H, $CH_2$), 2.33 (s, 3H, $CH_3$), 2.53 (t, J=7 Hz, 2H, $CH_2$), 3.98 (s, 2H, $CH_2$), 4.80 (s, 1H, OH), 6.93 (s, 1H, H6), 7.10 (d, 2H, J=9 Hz, protons ortho to bromo), 7.33 (d, 2H, J=9 Hz, protons meta to bromo).

EXAMPLE 33

2-(p-methoxyphenethyl)-3-methyl-4-hydroxy-5-propyl-7-chlorobenzofuran (a) Preparation of 2-(p-methoxyphenacetyl)-3-methyl-4-(p-methoxyphenacetyl-oxy)-5-propyl-7-chlorobenzofuran A solution of p-methoxyphenacetyl chloride (2.0 gm; 11 mmoles) in ethylene dichloride (5 mL) was added slowly to a cooled suspension of aluminium chloride (2.9 gm; 22 mmoles) in ethylene dichloride (145 mL). After stirring for a period of 10 minutes, 3-methyl-4-hydroxy-5-propyl-7-chlorobenzofuran (0.87 gm; 3.6 mmoles) in dichloroethylene (20 mL) was added over a period of 2 minutes. The reaction mixture was stirred at room temperature for 1 hour. It was cooled with an ice-bath and ice was added slowly. When the vigorous reaction subsided, the organic layer was separated and the aqueous phase was extracted with methylene chloride. The organic phases were combined, dried ($Na_2SO_4$), and concentrated in vacuo. The residue was chromatographed on silica gel and eluted with 15% ethylacetate in toluene to yield 1.3 gm of 2-(p-methoxyphenacetyl)-3-methyl-4-(p-methoxyphenac-etyloxy)-5-propyl-7-chlorobenzofuran.

$^1$H NMR 0.83 (t, J=7 Hz, 3H, $CH_3$), 1.50 (sextet, J=7 Hz, 2H, $CH_2$), 2.40 (s, 3H, $CH_3$), 2.40 (t, J=7 Hz, 2H, $CH_2$), 3.80 (m, 10H, $CH_3$ and $CH_2$), 6.80 (m, 4H, protons ortho to methoxy), 7.2 (m, 5H, H6 and protons meta to methoxy).

(b) Preparation of 2-(p-methoxyphenethyl)-3-methyl-4-(p-methoxyphenacetyloxy)-5-propyl-7-chlorobenzofuran (0.76 gm, 1.4 mmoles) in tetrahydrofuran (25 mL) was added a solution of 1M diborane in tetrahydrofuran (5 mL; 5 mmoles). The reaction was stirred at room temperature for 30 minutes. Methanol was then added and the volatiles were removed in vacuo to yield a residue that was taken up in tetrahydrofuran (25 mL) and added to a mixture of aluminium chloride (0.67 gm, 4 mmoles) and lithium aluminium hydride (0.80 gm, 21 mmoles) in tetrahydrofuran (25 mL). The mixture was stirred at room temperature for 2 hours and was refluxed for 15 minutes. It was cooled with an ice-bath and ice was added slowly. When the vigorous reaction subsided, the organic layer was separated and the aqueous phase was extracted with ether. The organic phases were combined, washed with brine, dried ($Na_2SO_4$), and concentrated in vacuo. The residue was chromatographed on silica gel and eluted with 15% ethyl acetate in hexane to yield 100 mg (20%) of 2-(p-methoxyphenethyl)-3-methyl-4-hydroxy-5-propyl-7-chlorobenzofuran.

$^1$H NMR 0.98 (t, J=7 Hz, 3H, $CH_3$), 1.63 (sextet, J=7 Hz, 2H, $CH_2$), 2.17 (s, 3H, $CH_3$), 2.58 (t, J=7 Hz, 2H, $CH_2$), 2.98 (s, 4H, $CH_2$), 3.80 (s, 2H, $CH_2$), 4.80 (s, 1H, OH), 6.80 (d, 2H, J=9 Hz, protons ortho to methoxy), 6.88 (s, 1H, H6), 7.03 (d, 2H, J=9 Hz, protons meta to methoxy).

EXAMPLE 34

2-(p-methoxyphenethyl)-3-methyl-4-hydroxybenzofuran (a) Preparation of 3-methyl-4-acetoxybenzofuran A solution of 3-methyl-4-hydroxybenzofuran (5.0 gm, 34.7 mmoles), acetic anhydride (50 mL) and triethylamine (25 mL) in tetrahydrofuran (150 mL) was stirred at room temperature overnight. The volatiles were removed in vacuo and the residue was purified by chromatography on silica gel. Elution with 15% ethylacetate in hexane yielded 3-methyl-4-acetoxybenzofuran.

$^1$H NMR 2.17 (s, 3H, $CH_3$), 2.40 (s, 3H, $CH_3$), 6.88 (d of d, 1H, H5), 7.20 (m, 3H, H2, H6 and H7).

(b) Preparation of 2-E-(1-(p-methoxyphenyl)-vinyl)-3-methyl-4-acetoxybenzofuran

A mixture of 3-methyl-4-acetoxybenzofuran (3.7 gm, 19.4 mmoles), palladium (II) acetate (5.6 gm, 25 mmoles), and p-methoxystyrene (6.7 gm, 50 mmoles) in acetic acid (100 mL) was refluxed for 45 minutes. The mixture was filtered through Celite and the filtrate was concentrated in vacuo. The residue was slurried with hexane, the insolubles were decanted, and the hexane solution was left to crystallize. The solid was filtered, washed with hexane and air dried to yield 1.6 gm (26%)

2-E-(1-(p-methoxyphenyl)-vinyl)-3-methyl-4-acetoxybenzofuran, mp. 146°–148° C.

$^1$H NMR 2.30 (s, 3H, CH$_3$), 2.33 (s, 3H, CH$_3$), 3.80 (s, 3H, CH$_3$), 7.10 (m, 9H, aromatic protons and vinyl protons)

(c) Preparation of 2-(p-methoxyphenethyl)-3-methyl-4-acetoxybenzofuran

A solution of 2-E-(1-(p-methoxyphenyl)-vinyl)-3-methyl-4-acetoxybenzofuran (1.29 gm, 4 mmoles) in ethanol (75 mL) was hydrogenated in a Parr hydrogenator in the presence of 5% palladium on charcoal at 50 psi for a period of 2 hours. The catalyst was filtered off and the filtrate was concentrated in vacuo to yield 1.26 gm (98%) of 2-(p-methoxyphenethyl)-3-methyl-4-acetoxybenzofuran, mp. 66°–69° C.

$^1$H NMR 2.10 (s, 3H, CH$_3$), 2.37 (s, 3H, CH$_3$), 2.97 (s, 1H, CH$_2$), 3.80 (s, 3H, CH$_3$), 7.10 (m, 7H, aromatic protons).

(d) Preparation of 2-(p-methoxyphenethyl)-3-methyl-4-hydroxybenzofuran

A solution of 2-(p-methoxyphenethyl)-3-methyl-4-acetoxy-benzofuran (1 gm, 3 mmoles) in methanol (50 mL) and 1N sodium hydroxide (10 mL) was stirred at room temperature for a period of 10 minutes. The mixture was acidified with 20% citric acid and the volatiles were removed in vacuo. The aqueous residue was extracted with ether, washed with water, dried (Na$_2$SO$_4$), filtered, and concentrated to yield a residue that was chromatographed on silica gel. Elution with 15% ethylacetate in hexane yielded 2-(p-methoxyphenethyl)-3-methyl-4-hydroxybenzofuran, mp. 72°–75° C.

$^1$H NMR 2.20 (s, 3H, CH$_3$), 2.97 (s, 4H, CH$_2$), 3.80 (s, 3H, CH$_3$), 6.90 (m, 7H, aromatic protons).

EXAMPLE 35

2-(p-methoxyphenethyl)-3-methyl-4-hydroxy-5-propylbenzofuran

(a) Preparation of 2-(p-methoxyphenethyl)-3-methyl-4-allyloxybenzofuran

A mixture of 2-(p-methoxyphenethyl)-3-methyl-4-hydroxybenzofuran (1.3 gm; 4.6 mmoles), potassium carbonate (1.38 gm, 10 mmoles), and allyl bromide (1.2 gm, 10 mmoles) in acetone (50 mL) was refluxed for a period of 5 hours. The solids were filtered off and the filtrate was concentrated in vacuo. The residue was chromatographed on silica gel and eluted with 15% ethylacetate in hexane to yield 0.9 gm of 2-(p-methoxyphenethyl)-3-methyl-4-allyloxybenzofuran, which was used as such for the next step.

(b) Preparation of 2-(p-methoxyphenethyl)-3-methyl-4-hydroxy-5-allylbenzofuran A solution of 2-(p-methoxyphenethyl)-3-methyl-4-allyloxybenzofuran (0.9 gm, 2.8 mmoles) in ortho dichlorobenzene (15 mL) was refluxed for 4.5 hours under a nitrogen atmosphere. The mixture was cooled to room temperature and was chromatographed on silica gel. Elution with 15% ethylacetate in hexane yielded 0.6 gm (67%) of 2-(p-methoxyphenethyl)-3-methyl-4-hydroxy-5-allylbenzofuran.

$^1$H NMR 2.10 (s, 3H, CH$_3$), 2.93 (s, 4H, CH$_2$), 3.40 (m, 2H, CH$_2$), 3.73 (s, 3H, CH$_3$), 5.17 (m, 2H, CH$_2$), 6.00 (m, 1H, CH), 6.73 (d, 2H, J=9 Hz, protons ortho to methoxy), 6.87 (s, 2H, H6 and H7), 7.08 (d, 2H, protons meta to methoxy).

(c) Preparation of 2-(p-methoxyphenethyl)-3-methyl-4-hydroxy-5-propylbenzofuran A solution of 2-(p-methoxyphenethyl)-3-methyl-4-hydroxy-5-allylbenzofuran (0.65 gm, 2 mmoles) in ethanol (50 mL) was hydrogenated in a Parr hydrogenator in the presence of 5% palladium on charcoal at 50 psi for a period of 2 hours. The catalyst was filtered off and the filtrate was concentrated in vacuo to yield 2-(p-methoxyphenethyl)-3-methyl-4-hydroxy-5-propylbenzofuran, mp 77°–79° C.

$^1$H NMR 0.93 (t, 3H J=7 Hz, CH$_3$), 1.60 (sextet, 2H, J=7 Hz, CH$_2$), 2.17 (s, 3H, CH$_3$), 2.57 (t, 2H, J=7 Hz, CH$_2$), 2.90 (s, 4H, CH$_2$), 3.73 (s, 3H, CH$_3$), 4.80 (s, 1H, OH), 6.73 (d, 2H, J=9 Hz, protons ortho to methoxy), 6.87 (s, 2H, H6 and H7), 7.03 (d, 2H, protons meta to methoxy).

EXAMPLE 36

2-Benzyl-3-methyl-4,5-dihydroxybenzofuran

(a) Preparation of 3-(3,4-methylenedioxyphenoxy)-4-phenyl-2-butanone

A mixture of sesamol (3,4-methylenedioxyphenol) (0.69 gm, 5 mmoles), 1-chloro-1-acetyl-2-phenethyl-1-triphenylphosphonium chloride (2.4 gm, 5 mmoles), and potassium carbonate (2.76 gm; 20 mmoles) in methylethylketone (50 mL) was refluxed for a period of 3 hours. More phosphonium salt was then added (0.4 gm, 0.84 mmoles) and reflux was continued for another 3 hours. The reaction mixture was cooled, filtered through Celite and concentrated in vacuo. The residue was chromatographed on silica gel and eluted with 20% ethylacetate in hexane to yield 629 mg (46%) of 3-(3,4-methylenedioxyphenoxy)-4-phenyl-2-butanone as an oil.

$^1$H NMR 2.10 (s, 3H, CH$_3$), 3.10 (d, 2H, J=7 Hz, CH$_2$), 4.63 (t, 1H, J=7 Hz, CH), 5.90 (s, 2H, CH$_2$), 6.2 (d of d, 1H, J=9 Hz, 3 Hz, HH6), 6.43 (d, 1H, J=3 Hz, H2), 6.67 (d, 1H, J=9 Hz, H5).

Anal Calcd. for C$_{17}$H$_{16}$O$_4$: C, 71.86; H, 5.67. Found: C, 71.92; H, 5.88.

(b) Preparation of 2-benzyl-3-methyl-5,6-methylenedioxybenzofuran

A mixture of 3-(3,4-methylenedioxyphenoxy)-4-phenyl-2-butanone (0.70 gm, 2.45 mmoles) in polyphosphoric acid (3.5 gm) was stirred by hand until the initial exothermic reaction subsided. The mixture was stirred in ice/water and the solid was collected, washed with water, and dried in vacuo. The solid was chromatographed on silica gel and eluted with 20% ethylacetate in hexane to yield 479 mg (73%) of 2-benzyl-3-methyl-5,6-methylenedioxybenzofuran.

Anal. Calcd. for C$_{17}$H$_{14}$O$_3$: C, 76.68; H, 5.30. Found: C, 76.55; H, 5.24.

(c) Preparation of 2-benzyl-3-methyl-5,6-dihydroxybenzofuran

A solution of 2-benzyl-3-methyl-5,6-methylenedioxybenzofuran (226 mg, 0.85 mmole) in methylene chloride (10 mL) was cooled at −65° C. and a 1M solution of boron tribromide in methylene chloride (0.85 mL) was added dropwise. The mixture was allowed to warm up to −25° C. and was kept in that range for 1 hour. Methanol (5 mL) was then added and the mixture was evaporated in vacuo. The residue was chromatographed on silica gel and eluted with 25% ethylacetate in hexane to yield 128 mg of 2-benzyl-3-methyl-5,6-dihydroxybenzofuran, mp. 95.5°–98° C.

$^1$H NMR 2.15 (s, 3H, CH$_3$), 4.03 (s, 2H, CH$_2$), 6.88 (s, 1H, H4), 6.95 (s, 1H, H7), 7.23 (m, 5H, phenyl).

EXAMPLE 37

2-(p-carboxymethoxybenzyl)-3-methyl-4-hydroxy-5-propyl-7-chlorobenzofuran

(a) Preparation of 2-(p-acetoxybenzyl)-3-methyl-4-acetoxy-5-propyl-7-chlorobenzofuran A solution of 2-(p-hydroxybenzyl)-3-methyl-4-hydroxy-5-propyl-7-chlorobenzofuran (1 gm; 3 mmoles) in pyridine (15 mL) and acetic anhydride (3 mL) was stirred at 50° C. for 15 minutes. The volatiles were removed in vacuo leaving a residue that crystallised on cooling. It was slurried with hexane, filtered, washed with hexane, and air dried to yield 1.1 gm (87%) of 2-(p-acetoxybenzyl)-3-methyl-4-acetoxy-5-propyl-7-chlorobenzofuran, mp. 119°–120° C.

$^1$NMR 0.93 (t, 3H, J=7 Hz, CH$_3$), 1.60 (sextet, 2H, J=7 Hz, CH$_2$), 2.20 (s, 3H, CH$_3$), 2.27 (s, 3H, CH$_3$), 2.33 (s, 3H, CH$_3$), 2.37 (t, 2H, J=7 Hz, CH$_2$), 4.00 (s, 2H, CH$_2$), 7.00 (d, 2H, J=9 Hz, protons ortho to methoxy), 7.07 (s, 1H, H6), 7.20 (d, 2H, J=9 Hz, protons meta to methoxy).

(b) Preparation of 2-(p-hydroxybenzyl)-3-methyl-4-acetoxy-5-propyl-7-chlorobenzofuran A solution of 2-(p-acetoxybenzyl)-3-methyl-4-acetoxy-5-propyl-7-chlorobenzofuran (150 mg, 0.36 mmole) in methanol (5 mL) and a saturated solution of ootassium carbonate (3 mL) was stirred at room temperature for 5 minutes. The reaction was poured in water, extracted with methylene chloride, washed with brine, dried (Na$_2$SO$_4$), and concentrated in vacuo to yield 107 mg (79%) of 2-(p-hydroxybenzyl)-3-methyl-4-acetoxy-5-propyl-7-chlorobenzofuran.

$^1$NMR: 0.93 (t, 3H, J=7 Hz, CH$_3$), 1.60 (sextet, 2H, J=7 Hz, CH$_2$), 2.18 (s, 3H, CH$_3$), 2.37 (s, 3H, CH$_3$), 2 50 (t, 2H, J=7 Hz, CH$_2$), 3.97 (s, 2H, CH$_2$), 5.20 (s, 1H, OH), 6.67 (d, 2H, J=9 Hz, protons ortho to methoxy), 7.03 (s, 1H, H6), 7.07 (d, 2H, J=9 Hz, protons meta to methoxy).

(c) Preparation of 2-(p-carboethoxymethoxybenzyl)-3-methyl-4-acetoxy-5-propyl-7-chlorobenzofuran A mixture of 2-(p-hydroxybenzyl)-3-methyl-4-acetoxy-5-propyl-7-chlorobenzofuran. (107 mg; 0.28 mmole), ethylbromoacetate (100 mg, 0.60 mmole), potassium carbonate (100 mg, 0.73 mmole) in acetone (10 mL) was refluxed for 30 minutes. The solids were filtered off, the filtrate was concentrated in vacuo to yield a residue that was purified by chromatography on silica gel. Elution with 20% ethylacetate in hexane yielded 133 (100%) of 2-(p-carboethoxymethoxybenzyl)-3-methyl-4-acetoxy-5-propyl-7-chlorobenzofuran.

$^1$NMR: 0.93 (t, 3H, J=7 Hz, CH$_3$), 1.33 (t, 3H, J=7 Hz, CH$_3$), 1.60 (sextet, 2H, J=7 Hz, CH$_2$), 2.18 (s, 3H, CH$_3$), 2.37 (s, 3H, CH$_3$), 2.50 (t, 2H, J=7 Hz, CH$_2$), 4.00 (s, 2H, CH$_2$), 4.23 (q, 2H, J=7 Hz, CH$_2$), 4.53 (s, 2H, CH$_2$), 6.83 (d, 2H, J=9 Hz, protons ortho to methoxy), 7.10 (s, 1H, H6), 7.23 (d, 2H, J=9 Hz, protons meta to methoxy).

(e) Preparation of 2-(p-carboxymethoxybenzyl)-3-methyl-4-hydroxy-5-propyl-7-chlorobenzofuran A solution of 2-(p-carboethoxymethoxybenzyl)-3-methyl-4-acetoxy-5-propyl-7-chlorobenzofuran (133 mg; 0.28 mmole) in methanol (10 mL) and 10N sodium hydroxide (1 mL) was stirred at room temperature for a period of 30 minutes. Water was then added and the mixture was acidified with 6N hydrochloric acid. The solid was filtered, washed with water, and air-dried to yield 93 mg (82%) of 2-(p-carboxymethoxybenzyl)-3-methyl-4-hydroxy-5-propyl-7-chlorobenzofuran, mp. 179°–180° C.

$^1$NMR 1.00 (t, 3H, J=7 Hz, CH$_3$), 1.67 (sextet, 2H, J=7 Hz, CH$_2$), 2.43 (s, 3H, CH$_3$), 2.67 (s, 3H, CH$_3$), 4.00 (s, 2H, CH$_2$), 4.60 (s, 2H, CH$_2$), 6.87 (d, 2H, J =9 Hz, protons ortho to methoxy), 6.93 (s, 1H, H6), 7.20 (d, 2H, J=9 Hz, protons meta to methoxy).

EXAMPLE 38

2-(p-methoxybenzyl)-3-methyl-4-succinyloxy-5-propyl-7-chlorobenzofuran

A solution of 2-(p-methoxybenzyl)-3-methyl-4-hydroxy-5-propyl-7-chlorobenzofuran (0.5 gm, 1.45 mmole), 0.58 succinic anhydride (0.58 gm, 5.8 mmoles), and triethylamine (0.58 gm, 5.8 mmoles) in tetrahydrofuran (15 mL) was refluxed overnight. The volatiles were removed in vacuo and the residue was purified by chromatography on silica gel. Elution with 15% ethylacetate in hexane containing also 5% acetic acid yielded 0.45 gm (69%) of 2-(p-methoxybenzyl)-3-methyl-4-succinyloxy-5-propyl-7-chlorobenzofuran, mp. 151°–152° C.

$^1$NMR: 10.93(t, 3H, J=7 Hz, CH$_3$), 1.60 (sextet, 2H, J=7 Hz, CH$_2$), 2.27 (s, 3H, CH$_3$), 2.57 (s, 3H, CH$_3$), 2.90 (m, 4H, CH$_2$), 3.80 (s, 3H, CH$_3$), 4.00 (s, 2H, CH$_2$), 6.83 (d, 2H, J=9 Hz, protons ortho to methoxy), 7.07 (s, 1H, H6), 7.20 (d, 2H, J=9 Hz, protons meta to methoxy).

EXAMPLE 39

2-(p-carboethoxymethoxybenzyl)-3-methyl-4-carboethoxymethoxy-5-propyl-7-chlorobenzofuran A mixture of 2-(p-hydroxybenzyl)-3-methyl-4-hydroxy-5-propyl-7-chlorobenzofuran (483 mg; 1.46 mmole), ethylbromoacetate (325 mg, 1.90 mmole), and potassium carbonate (500 mg, 3.62 mmoles) in acetone (20 mL) was refluxed for 60 minutes. The solids were filtered off. The filtrate was concentrated in vacuo to yield a residue that was purified by chromatography on silica gel. Elution with 20% ethylacetate in hexane yielded 520 (85%) of 2-(p-carboethoxymethoxybenzyl)-3-methyl-4-carboethoxymethoxy-5-propyl-7-chlorobenzofuran.

$^1$NMR: 0.93 (t, 3H, J=7 Hz, CH$_3$), 0.98 (t, 3H, J=7 Hz, CH$_3$), 1.33 (t, 3H, J=7 Hz, CH$_3$), 1.60 (sextet, 4H, J=7 Hz, CH$_2$), 2.33 (t, 4H, J=7 Hz, CH$_2$), 4.00 (q, 2H, J=7 Hz, CH$_2$), 4.18 (s, 2H, CH$_2$), 4.30 (s, 2H, CH$_2$), 6.57 (d, 2H, J=9 Hz, protons ortho to methoxy), 6.67 (s, 1H, H6), 6.90 (d, 2H, J=9 Hz, protons meta to methoxy).

EXAMPLE 40

O-sulfate of 2-(p-methoxybenzyl)-3-methyl-4-hydroxy-5-propyl-7-chlorobenzofuran, ammonium salt A solution of 2-(p-methoxybenzyl)-3-methyl-4-hydroxy-5-propyl-7-chlorobenzofuran (5 gm, 14.5 mmoles) was added at 0° C. to a mixture of diethyl aniline (4.3 ml) and chlorosulfonic acid (1 ml) in carbon disulfide (50 ml). The temperature was allowed to rise to room temperature and after 15 minutes, it was refluxed for 15 minutes. The reaction mixture was evaporated to dryness and the residue was purified by preparative thin layer chromatography. Eluting with a mixture of methanol, chloroform and ammonium hydroxide in the ratio of 4:8:1 (v/v/) yielded 5 gm of the sulfate ester of 2-(p-methoxybenzyl)-3-methyl-4-hydroxy-5-propyl-7-chlorobenzofuran as its ammonium salt; m.p.: 207°-209° C.

$^1$NMR 0.93 (t, 3H, J=7 Hz, CH$_3$), 1.70 (sextet, 2H, J=7 Hz, CH$_2$), 2.47 (s, 3H, CH$_3$, 2.97 (t, J=7 Hz, 2H, CH$_2$), 3.70 (s, 3H, CH$_3$), 4.03 (s, 2H, CH$_2$), 6.83 (d, 2H, J=9 Hz, protons ortho to methoxy), 7.10 (d, 2H, J=9 Hz, protons meta to methoxy), 7.27 (s, 1H, H6).

EXAMPLE 41

O-phosphate of 2-(p-methoxybenzyl)-3-methyl-4-hydroxy-5-propyl-7-chlorobenzofuran A solution of 2-(p-methoxybenzyl)-3-methyl-4-hydroxy-5-propyl-7-chlorobenzofuran (5 gm, 14.5 mmoles) in chloroform (25 ml) was added at 0° C. to a solution of phosphorus oxychloride (75 ml) in pyridine (25 ml) and acetone (250 ml). The mixture was stirred at room temperature for a period of 1 hour and refluxed for 2 hours. The reaction mixture was evaporated to dryness and the residue was slurried in a small volume of water. The solids were filtered, washed, and air-dried to yield the phosphate ester of 2-(p-methoxybenzyl)-3-methyl-4-hydroxy-5-propyl-7-chlorobenzofuran.

$^1$NMR: 0.93 (t, 3H, J-7 Hz, CH$_3$), 1.60 (sextet, 2H, J=7 Hz, CH$_2$), 2.27 (s, 3H, CH$_3$), 2.87 (t, J=7 Hz, 2H, CH$_2$), 3.80 (s, 3H, CH$_3$), 4.00 (s, 2H, CH$_2$), 6.83 (d, 2H, J=9 Hz, protons ortho to methoxy), 7.10 (d, 2H, J=9 Hz, protons meta to methoxy), 7.15 (s, 1H, H6).

Anal. Calcd. C, 56.54; H, 5.18; Cl, 8.35; P, 7.30. Found: C, 56.59; H, 5.21; Cl, 8.52; P, 7.43.

SCHEME V

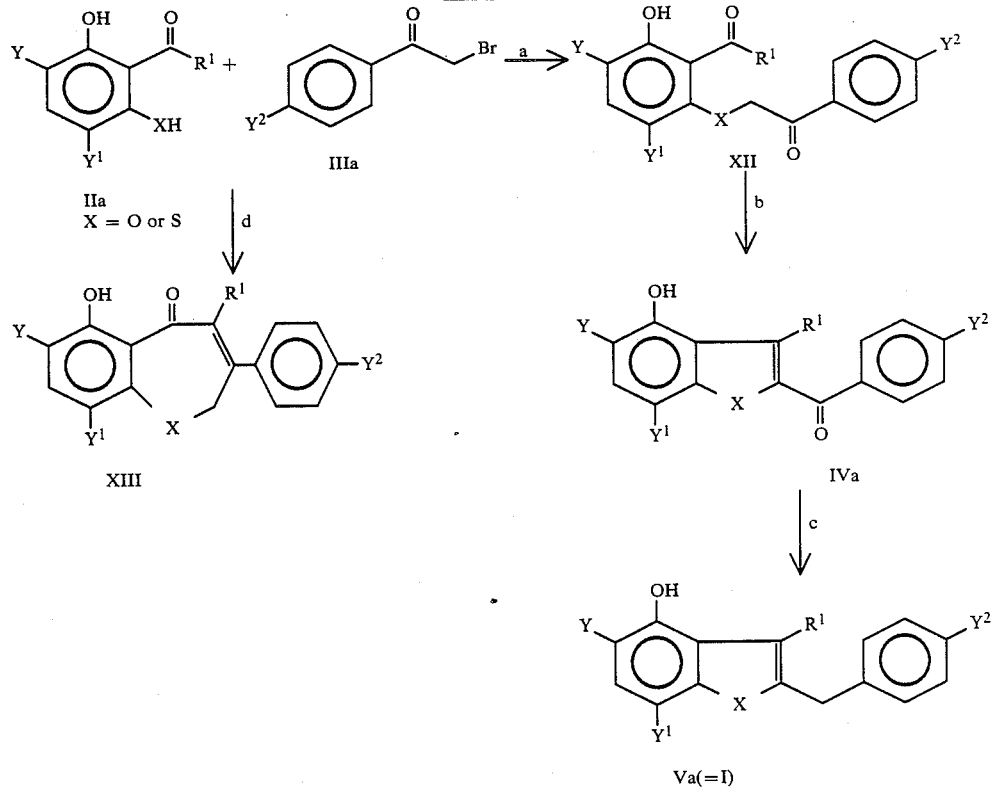

a Cs$_2$CO$_3$, CH$_3$CN;
b HCl/H$_2$O/CH$_3$CN/Δ;
c ZnI$_2$/NaCNBH$_3$/CH$_2$ClCH$_2$Cl;
d K$_2$CO$_3$, acetone An alternative preparation of compounds of structure I is shown in Scheme V, which is an improved modification of Scheme I. Reaction of substituted acyl phenols (IIa) with various substituted phenacyl bromides (IIIa) in the presence of 0.5 molar equivalents of cesium carbonate in acetonitrile at room temperatures gave the monoalkylated products (XII). Products (XII) can be isolated but in most cases they are cyclized in situ to the benzofuran (IVa) by the addition of aqueous HCl and reflux for 6-8 hours. It is important to note that in the case where Y=Y$^1$=hydrogen or alkyl, alkylation followed by cyclization can be effected by simply refluxing (IIa) and (IIIa) with potassium carbonate in acetone. In the case where Y$^1$=halogen and Y=alkyl, using other bases like potassium carbonate or sodium hydride or even a slight excess of CsCO3, the reaction takes an alternative path to give only the 7-membered ring derivatives (XIII).

In general the reduction of the benzoyl ketone (IVa) to the corresponding benzyl derivative (Va) by lithium aluminum hydride and aluminum chloride complex can be achieved in reasonable yield. An alternative, less hazardous method using sodium cyanoborohydride in the presence of zinc iodide gives rise to product yields of greater than 90% yield for most cases.

In the following discussion, the Arabic numbers refer to compounds in Table 1.

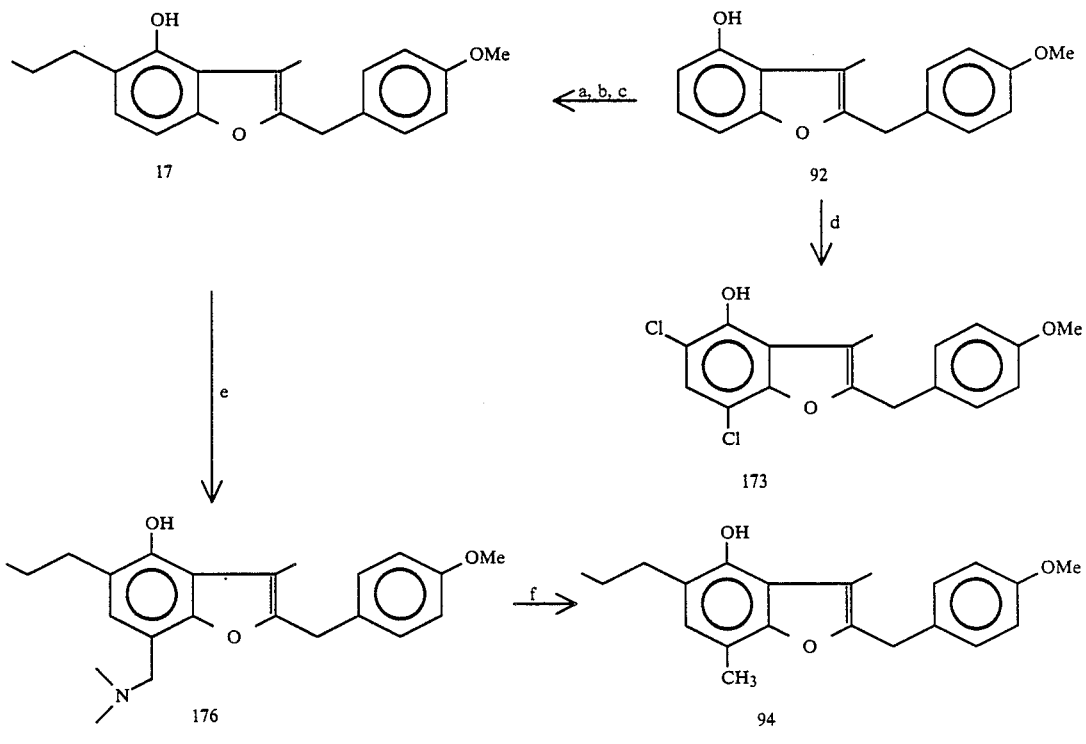

SCHEME VI a K2CO3, allylbromide;
b PhCl2,Δ;
c H2/Pd/C;
d Cl2, e $\diagdown_{\diagup}$N+=I−, CH2Cl2;

f NaBH4, EtOH, Δ.

Allylation of (92) (Scheme VI) followed by Claisen rearrangement and hydrogenation gives the 5-propyl derivative (17). Chlorination of (92) gives the dichlorinated product (173). Treatment of (17) with 3 eqivalents of Eschenmoser's salt (dimethylmethyleneimmonium iodide) in dichloromethane gives the corresponding 7-(dimethylaminomethyl) derivative (176). This compound is reduced by NaBH4 in refluxing ethanol to give the 5-propyl-7-methyl-derivative (94).

SCHEME VII

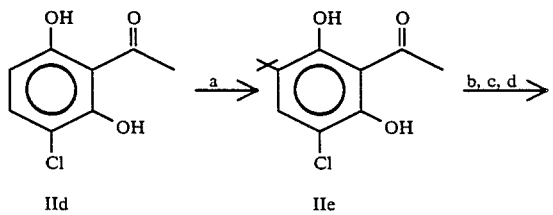

IId          IIe

SCHEME VII
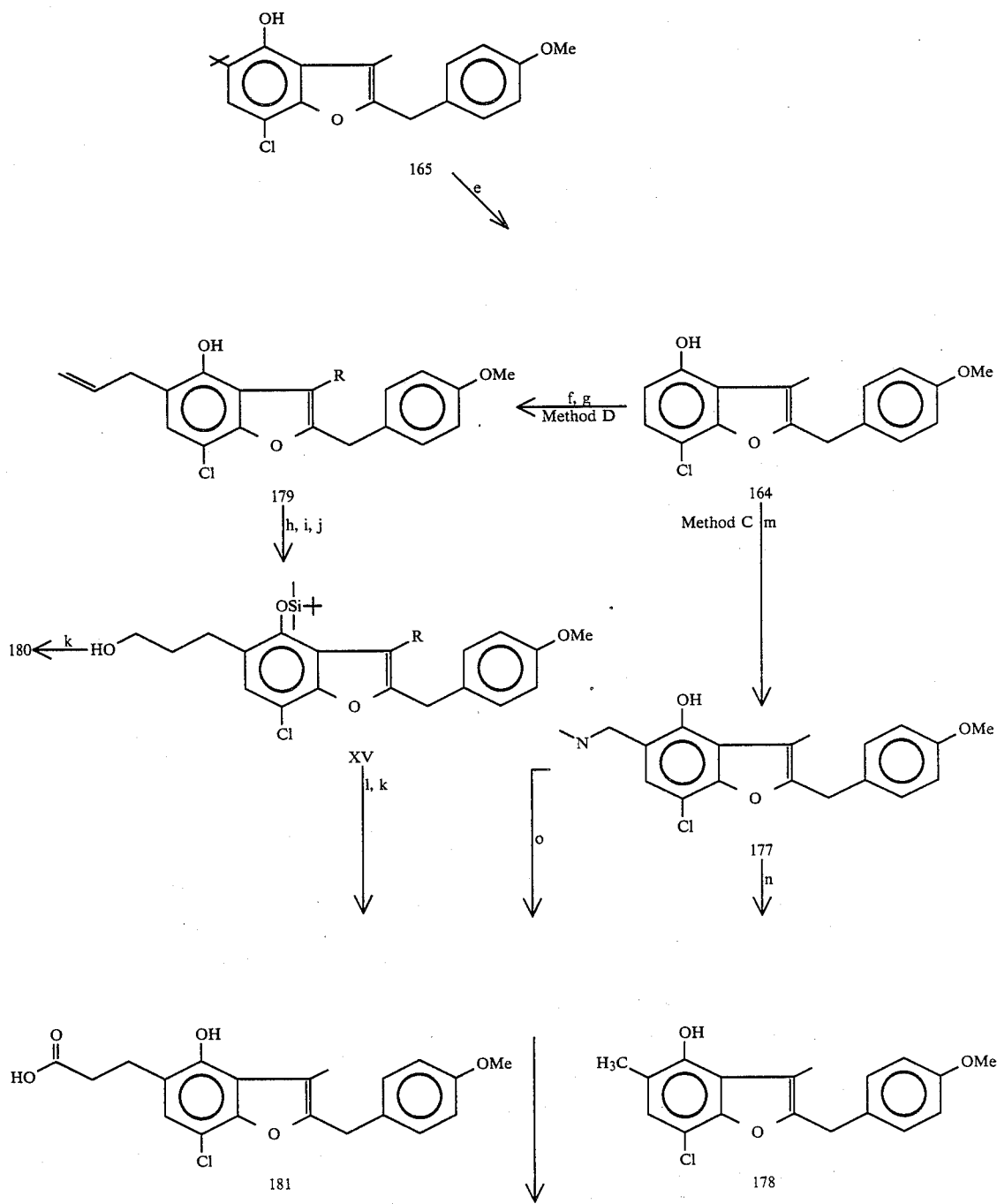

-continued
SCHEME VII

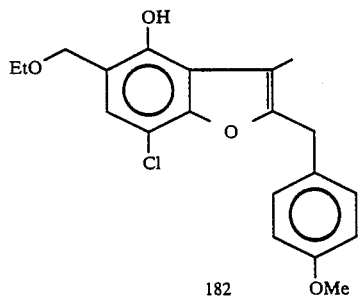

182 a t-BuCl, H$_2$SO$_4$;
b 4-methoxyphenacylbromide, Cs$_2$CO$_3$;
c HCl/CH$_3$CN/H$_2$O, Δ;
d ZnI$_2$/NaCNBH$_3$;
e AlCl$_3$/PhH;
f allylbromide, K$_2$CO$_3$;
g PhCl$_2$, Δ;
h t-BuSiMe$_2$Cl;
i BH$_3$, THF;
j H$_2$O$_2$, NaOH;
k Bu$_4$NF;
l Jones;
m =N$^+$=I$^\ominus$;
n NaBH$_4$, EtOH, Δ;
o C$_2$H$_5$Br, EtOH Reaction of the 3-chloro-5-t-butyl-2,6-dihydroxyacetophenone (Scheme VII) with 4-methoxyphenacyl bromide as described in Scheme V gives the desired 5-t-butyl-4-hydroxy-7-chlorobenzofuran derivative (165) after reduction. The t-butyl substituent is then removed by treating (165) with aluminum chloride in benzene for 1 hour. Allylation of (164) followed by Claisen rearrangement gives the 5-allyl derivative (179) which after silylation of the phenol is hydroborated to give the corresponding alcohol (XV). Oxidation of the alcohol with Jones reagent gives the corresponding acid. Deprotection with tetra-n-butylammonium fluoride gives the desired alcohol (180) and acid (181). Reaction of (164) with Eschenmoser's salt gives the 5-dimethylaminomethyl derivative (177) which is reduced to the 5-methyl derivative (178) with sodium borohydride in ethanol. Quaternization of the tertiary amine with ethyl bromide followed by displacement of the quaternary salt with ethanol gives the 5-(ethoxymethyl) derivative (182).

SCHEME VIII

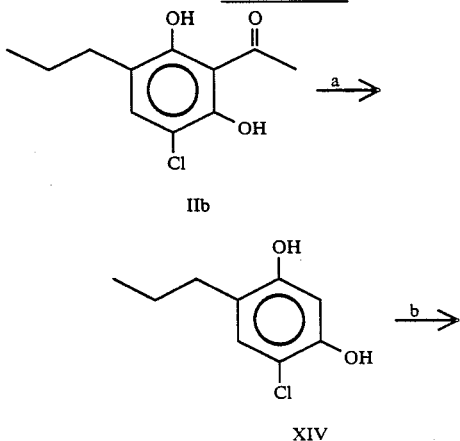

-continued
SCHEME VIII

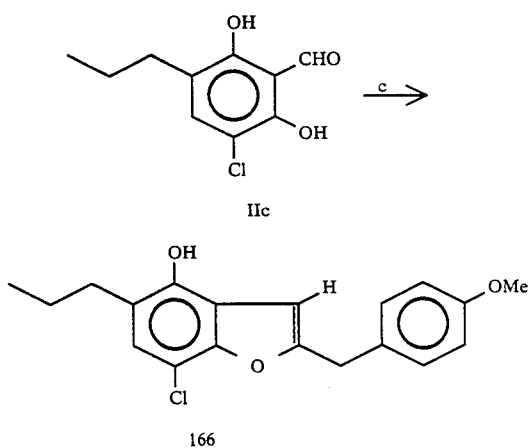

a HBr, HOAc;
b Hexamine, TFA;
c as per scheme V

To prepare 166 (Scheme VIII), 1-formyl-3-chloro-5-propyl-2,6-dihydroxybenzene (IIc) is prepared from its acetophenone analog IIb. Deacylation of the latter with HBr in acetic acid gives the corresponding dihydroxybenzene derivative XIV. Formylation of the latter with hexamine in trifluroacetic acid gives IIc in 85% yield. Condensation of the latter with p-methoxyphenacyl bromide is achieved with potassium carbonate in refluxing acetone to give the corresponding benzofuran (166) in 79% yield after reduction. The corresponding acetyl analog under the same conditions gives the 7-membered ring product XIII as described in Scheme V.

The 3-propyl analog (167) is prepared by the standard method described in Scheme V. The 4'-H (108), 4'-Chloro (174), 2',4'-dimethoxy (175) derivatives are also prepared as described in Scheme V.

SCHEME IX

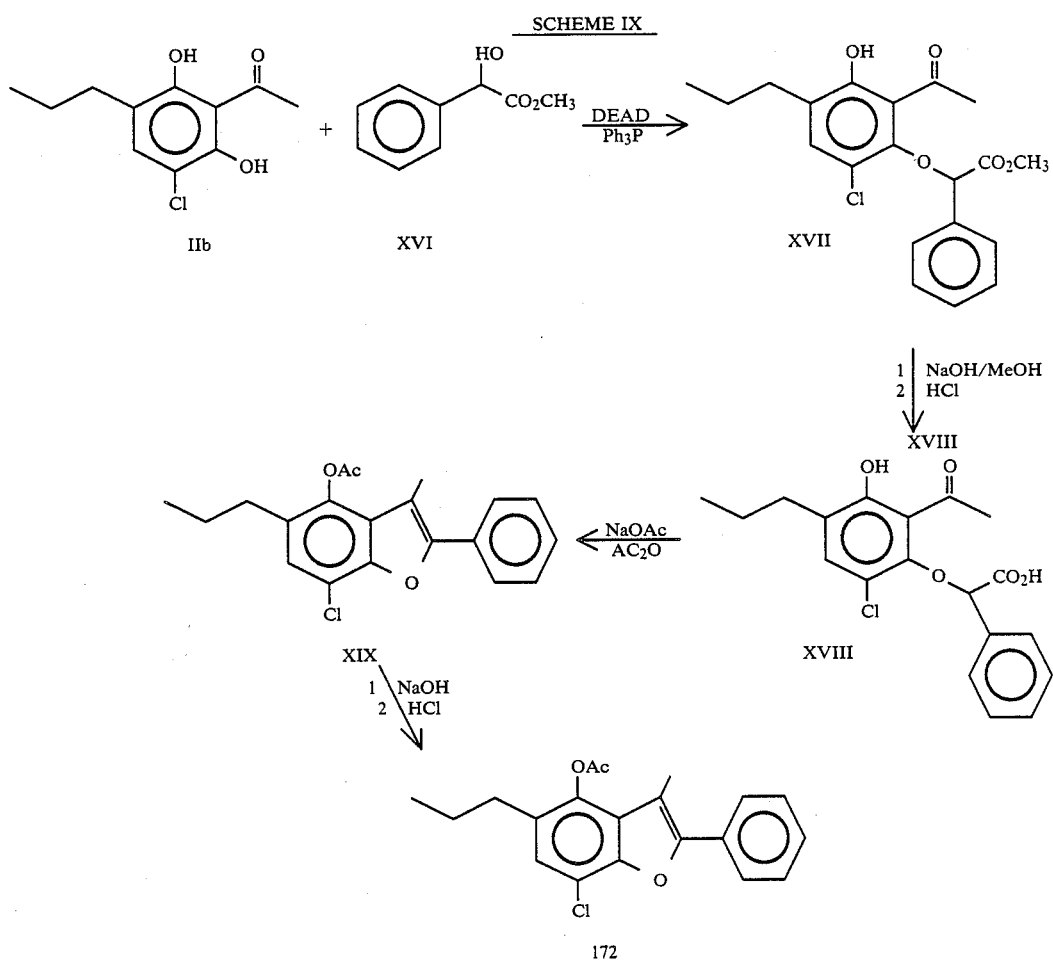

To prepare the 2-phenyl analog (172) (Scheme IX), 1-acetyl-3-chloro-5-propyl-2,6-dihydroxybenzene (IIb) is coupled with methyl 2-hydroxy-2-phenylacetate in the presence of diethyldiazodicarboxylate and triphenylphosphine to give the coupled product XVII. Hydrolysis of the latter followed by cyclization in acetic anhydride and sodium acetate gives the 2-phenybenzofuran XIX which after hydrolysis of the acetate gives compound 172.

SCHEME X

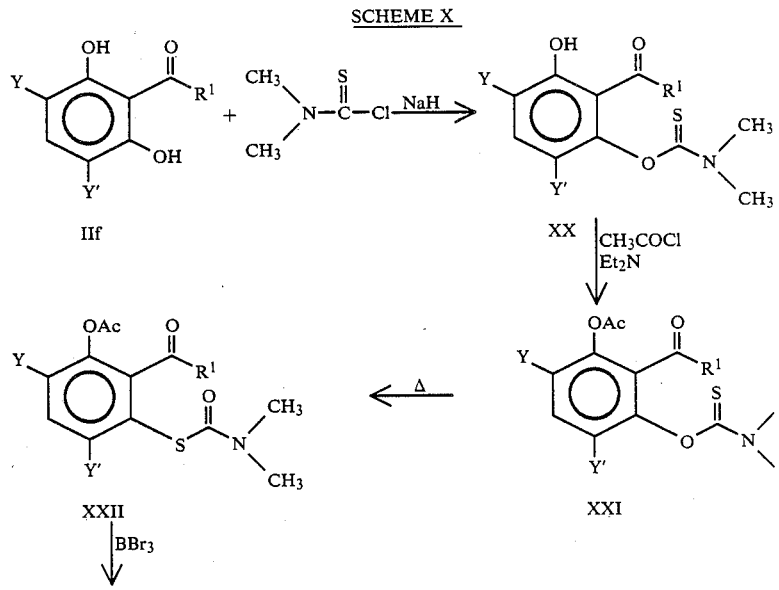

SCHEME X

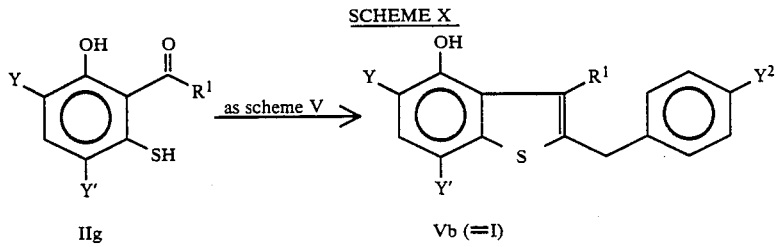

To prepare the benzothiophene analog (Vb), the dihydroxyacetophenone derivative IIf (Scheme X) is reacted with dimethylthiocarbamoyl chloride to give the corresponding O-dimethylthiocarbamate XX. Thermal rearrangement in refluxing O-dichlorobenzene of the acetate XXI of the latter gives the S-dimethylthiocarbamate XXII which after treatment with boron tribromide gives the mercapto compound IIg. Transformation of the latter to the benzothiophene Vb is essentially the same as that described in Scheme V.

TABLE 5
COMPOUNDS OF FORMULA I

| Compound | Ex. No. | Scheme | mp °C. | Formula |
|---|---|---|---|---|
| 163 |  | II | 49–50 | $C_{12}H_{13}O_2Cl$ |
| 164 | 44 | VII | 159 | $C_{17}H_{15}ClO_3$ |
| 165 | 43 | VII | 128 | $C_{21}H_{23}ClO_3$ |
| 166 | 51 | V | 88 | $C_{19}H_{19}ClO_3$ |
| 167 |  | V | 90 | $C_{22}H_{25}ClO_3$ |
| 168 |  | V | 93 | $C_{21}H_{23}ClO_3$ |
| 169 |  | V | oil | $C_{19}H_{28}O_2$ |
| 170 |  | V | 104 | $C_{21}H_{24}O_4$ |
| 171 | 53 | X | 80 | $C_{20}H_{21}SO_2Cl$ |
| 172 | 52 | IX | 103 | $C_{18}H_{17}ClO_2$ |
| 173 |  | VI | 121 | $C_{17}H_{14}Cl_2O_3$ |
| 174 |  | V | 76 | $C_{19}H_{18}Cl_2O_2$ |
| 175 |  | V | 108 | $C_{21}H_{23}O_4Cl$ |
| 176 | 21 | VI | oil | $C_{20}H_{22}ClNO_3$ |
| 177 | 45 | VII | oil | $C_{20}H_{22}ClNO_3$ |
| 178 | 46 | VII | 128 | $C_{18}H_{17}ClO_3$ |
| 179 | 48 | VII | 90 | $C_{20}H_{19}ClO_3$ |
| 180 | 49 | VII | 133 | $C_{20}H_{21}ClO_4$ |
| 181 | 50 | VII | 149 | $C_{20}H_{19}ClO_5$ |
| 182 | 47 | VII | oil | $C_{26}H_{21}O_4Cl$ |

EXAMPLE 42

Alternate preparation of 2-(p-methoxybenzyl)-3-methyl-4-hydroxy-5-propyl-7-chlorobenzofuran (Example 23)

(a) Preparation of 4-hydroxy-7-chloro-2-(p-methoxybenzoyl)-3-methyl-5-propylbenzofuran To a solution of 5-chloro-2,6-dihydroxy-3-propylacetophenone (Example 23, Step a) (3.5 g, 14.5 mmol) in acetonitrile (40 mL) was added cesium carbonate (2.49 g, 7.65 mmol). The mixture was refluxed with stirring for 30 min. The resulting dark red mixture was cooled to 5° C. and to it was added a solution of 2-bromo-4'-methoxyacetophenone (3.5 g, 15.3 mmol) in acetonitrile (8.0 mL). The mixture was then warmed to room temperature for 2 h. HCl (6N, 30 mL) was added to the reaction mixture which was then refluxed for another 2 h. The mixture was cooled to 0° C., diluted with ice water (30 mL) and filtered. The product was washed with more water and dried to give the title compound.

$^1$H NMR (250 MHz, CDCl$_3$) δ 0.95 (t, 3H), 1.6 (m, 2H), 2.5 (t, 2H), 2.75 (s, 3H), 3.85 (S, 3H), 6.95 (d, 2H, J=6 Hz), 7.1 (S, 1H), 8.15 (d, 2H, J=6 Hz).

(b) Preparation of 4-hydroxy-7-chloro-2-(4'-methoxyphenylmethyl)-3-methyl-5-propylbenzofuran To a stirring solution of 4-hydroxy-7-chloro-2-(4'-methoxyphenylmethyl)-3-methyl-5-propylbenzofuran (Step a) (27 g, 75.4 mmol) in dichloroethane (350 mL) was added zinc iodide (36.85 g, 113 mmol) followed by sodium cyanoborohydride (35.54 g, 565 mmol). The resulting mixture was refluxed for 6 h. The cooled mixture was poured into a cold saturated solution of ammonium chloride acidified with HCl and stirred for ½ h. Extraction with ethyl acetate and chromatography (15% EtOAc in hexane) of the crude concentrated extract gave the title compound, identical with material prepared in Example 23.

Compounds 167–170 and 174 and 175 in Table 5 were prepared by the methodology of Example 42.

EXAMPLE 43

Preparation of 4-hydroxy-7-chloro-5-tbutyl-2-(4'-methoxyphenylmethyl)-3-methylbenzofuran (165) (a) Preparation of 3-chloro-2,6-dihydroxyacetophenone To 2,6-dihydroxyacetophenone (15.2 g, 160 mmol) dissolved in dichloromethane (800 ml) was added N-chlorosuccinimide (14.68 g, 110 mmol). The resulting solution was stirred overnight at room temperature. The reaction mixture was poured onto a flash chromatography column and eluted with dichloromethane to give the title compound.

$^1$H NMR (90 MHz, CDCl$_3$) δ 2.72 (s, 3H) 6.45 (d, 2H, J =9 Hz) 7.32 (d, 2H, J=9 Hz).

(b) Preparation of 5-chloro-2,6-dihydroxy-3-tertbutylacetophenone

To 3-chloro-2,6-dihydroxyacetophenone (from Step a, 30 g, 161 mmol) dissolved in 2-chloro-2-methylpropane (200 ml) was added H$_2$SO$_4$ 98% (3 ml). The mixture was refluxed for 4 hours, cooled and washed with H$_2$O (200 ml). The organic solution was separated evaporated and the residue chromatographed on silica gel (eluted with 15% EtOAC in hexane) to give the title compound.

$^1$H NMR (90 MHz, CDCl$_3$) δ 1.35 (s, 9H) 2.75 (s, 3H) 7.38 (s, 1H).

(c) Preparation of 4-hydroxy-7-chloro-5-t-butyl-2-(4'-methoxyphenylmethyl)-3-methylbenzofuran (165)

The title compound was prepared according to the methodology of Example 42 using the starting material from Step b above.

$^1$H NMR (90 MHz CDCl$_3$) δ 1.40 (s, 9H) 2.40 (s, 3H) 3.75 (s, 3H) 3.95 (s, 2H) 5.15 (s, 1H) 6.8 (d, 2H, J =9 Hz) 7.18 (d, 3H).

EXAMPLE 44

Preparation of 4-hydroxy-7-chloro-2-(4'-methoxyphenylmethyl)-3-methylbenzofuran (164)

To a cold solution (0° C.) of 4-hydroxy-7-chloro-5-t-butyl-2-(4'-methoxyphenylmethyl)-3-methylbenzofuran(165) (Example 43) (10 g, 27.8 mmol) in 500 mL dichloromethane was added 5 mL of anisole followed by aluminum chloride (13 g, 0.1 mol) in portions. The mixture was allowed to stir for 1 h and then poured onto ice. The mixture was extracted with dichloromethane, the organic extracts were dried, concentrated and chromatographed to give the title compound.

$^1$H NMR (250 MHz, CDCl$_3$) δ 6 2.38 (S, 3H), 3.85 (s, 3H), 4.1 (S, 2H), 6.45 (d, 1H, J=6 Hz), 6.8 (d, 2H, J=6 Hz), 6.95 (d, 1H, J=6 Hz), 7.15 (d, 2H, J=6 Hz).

Anal. Calcd. for C$_{17}$H$_{15}$ClO$_3$: C, 67.44; H, 4.95; Cl, 11.72. Found: C, 67.81; H, 5.31; Cl, 11.43.

EXAMPLE 45

Preparation of 4-hydroxy-5-dimethylaminomethyl-2-(4'-methoxyphenylmethyl)-3-methyl-benzofuran hydrochloride (177)

To a solution of (164) (Example 44) (1 g, 3.3 mmol) in 25 mL dichloromethane was added Eschenmoser's salt (0.6125 g, 3.3 mmol). The mixture was allowed to stir a room temperature for 20 h. The solvent was evaporated. The residue was chromatographed on silica gel (eluted with 20% EtOAc in hexane) to give the title compound.

$^1$H NMR (250 MHz, CDCl$_3$) δ 2.35 (d, 6H), 3.65 (s, 2H), 3.75 (s, 3H), 4.0(s, 2H), 6.75 (s, 1H), 6.82 (d, 2H, J=6 Hz), 7.15 (d, 2H, J=6 Hz).

EXAMPLE 46

Preparation of 4-hydroxy-7-chloro-3,5-dimethyl-2-(4'-methoxyphenylmethyl)benzofuran (178)

To a solution of (177) (Example 45) (0.106 g, 0.3 mmol) in 5 mL ethanol was added sodium borohydride (0.111 g, 3 mmol). The mixture was refluxed for 1 h, cooled and poured into cold dilute HCl (1N). Extraction with ethyl acetate, followed by chromatography of the concentrated organic extract gave the title compound.

$^1$H NMR (250 MHz, CDCl$_3$) δ 2.25 (S, 3H), 2.38 (S, 3H), 3.78 (S, 3H), 4.04 (S, 2H), 4.78 (S, 1H), 6.85 (d, 2H, J=6 Hz), 6.92 (S, 1H), 7.18 (d, 2H, J=6 Hz).

Anal. Calcd. for C$_{18}$H$_{17}$ClO$_3$: C, 68.24; H, 5.37; Cl, 11.21. Found: C, 68.14; H, 5.66; Cl, 11.16.

EXAMPLE 47

Preparation of 4-hydroxy-5-ethoxymethyl-2-(4'-methoxyphenylmethyl)-3-methylbenzofuran (182)

A mixture of (177) (Example 45) (0.1 g, 0.28 mmol), ethyl bromide, (1 mL) and ethanol (5 mL) was refluxed for 6 h. The solvent was evaporated, the residue was chromatographed on preparative tlc to give the title compound.

$^1$H NMR (250 MHz, CDCl$_3$) δ 1.2 (t, 3H), 2.3 (S, 3H), 3.55 (q, 2H), 3.7 (s, 3H), 3.95 (s, 2H), 4.5 (s, 2H), 6.70 (S, 1H), 6.75 (d, 2H, J=6 Hz), 7.1 (d, 2H, J=6 Hz)
Mass Spec. (M+) 360 m/e .

EXAMPLE 48

Preparation of 5-allyl-4-hydroxy-7-chloro-2-(4'-methoxyphenylmethyl)-3-methylbenzofuran (179)

To a solution of 4-hydroxy-7-chloro-2-(4'-methoxyphenylmethyl)-3-methylbenzofuran (164) (Example 44) (1.5 g, 5 mmol) in 30 mL acetone was added potassium carbonate (690 mg, 5 mmol) amd allyl bromide (605 mg, 5 mmol). The mixture was refluxed for 20 h, then filtered through celite after cooling to room temperature. Concentration of the filtrate gave 1.94 g of the 4-allyloxy-7-chloro-2-(4'-methoxyphenylmethyl)-3-methylbenzofuran as a light brown oil. The crude material was refluxed in 8 mL o-dichlorobenzene for 6 h. Evaporation of the solvent followed by chromatography gave the title compound as a white solid, mp 90°–93° C.

$^1$H NMR (250 MHz, CDCl$_3$) δ 2.35 (S, 3H), 3.40 (d, 2H, J=6 Hz), 3.78 (S, 3H), 4.0 (S, 2H), 5.23 (m, 2H), 6.00 (m, 2H), 6.84 (d, 2H, J=7.5 Hz), 6.91 (S, 1H), 7.18 (d, 2H, J=7 Hz).

Anal. Calcd. for C$_{20}$H$_{19}$ClO$_3$: C, 70.07; H, 5.59; Cl, 10 34. Found: C, 69.81; H, 5.90; Cl, 10.44.

EXAMPLE 49

Preparation of 4-hydroxy-5-(3-hydroxy)propyl-7-chloro-2-(4'-methoxyphenylmethyl)-3-methylbenzofuran (180)

To a solution of (179) (Example 48) (342 mg, 1 mmol) in 10 mL dichloromethane was added t-butyldimethylchlorosilane (180 mg, 1.2 mmol), triethylamine (202 mg, 2 mmol), dimethylaminopyridine (61 mg, 0.5 mmol). The mixture was allowed to stir at room temperature for 20 h. Dilute HCl was added and the mixture was extracted with ethyl acetate. The extracts were dried (anhyd. MgSO$_4$) and chromatography of the concentrated extract gave 410 mg of the silylated phenol. A solution of the latter product in dry THF (5 mL) was cooled to −78° C. and a solution of borane in THF (1M, 2mL) was added. The mixture was allowed to stir at −78° C. for 1 h, warmed to room temperature and stirred for 1 h. Trimethylamine N-oxide (684 mg, 6 mmol) was added. The mixture was refluxed for 3 h, chromatography of the cooled mixture gave 400 mg of the corresponding alcohol. Treatment of the silylated phenol alcohol with tetra-n-butyl ammonium fluoride in THF gave the title compound (180), mp 133°–136° C.

$^1$H NMR (250 MHz, CDCl$_3$) δ 1.89 (m, 2H), 2.38 (S, 3H), 2.81 (m, 2H), 3.66 (m, 2H), 3.78 (s, 3H), 4.01 (S, 2H), 6.83 (d, 2H, J=7 Hz), 6.89 (S, 1H), 7.18 (d, 2H, J=7 Hz).

Anal Calcd. for C$_{20}$H$_{21}$ClO$_4$: C, 66.57; H, 5.87; Cl, 9.83. Found: C, 66.50; H, 5.70; Cl, 9.80.

EXAMPLE 50

Preparation of 4-hydroxy-5-(2-carboxy)ethyl-7-chloro-2-(4'-methoxyphenylmethyl)-3-methylbenzofuran (181)

To a solution of the silyated phenol derivative of (180) (Example 49) (400 mg, 0.84 mmol) in 10 mL acetone was added dropwise at 0° C. the Jones reagent.

The reaction was monitored by tlc. The crude silylated acid after workup was treated with tetra-n-butyl ammonium fluoride as described before. The title compound was isolated by preparative tlc, mp 149°–151° C.

$^1$H NMR (250 MHz, CDCl$_3$) δ 2.35 (S, 3H), 2.85 (m, 4H), 3.78 (S, 3H), 4.00 (S, 2H), 6.82 (d, 2H, J=7 Hz), 6.87 (S, 1H), 7.16 (d, 2H, J=7 Hz).

EXAMPLE 51

7-Chloro-4-hydroxy-2-(4'-methoxyphenylmethyl)-5-propylbenzofuran (166)

(a) Preparation of 2-chloro-4-propyl-1,5-dihydroxybenzene

To a solution of 5-chloro-3-propyl-2,6-dihydroxyacetophenone (Example 23, Step a) (5 g, 32 mmol) in 50 mL acetic acid was added 50 mL hydrogen bromide. The mixture was refluxed for 5 h. Water was added and the mixture was extracted with ethyl acetate. Chromatography of the concentrated organic extract gave the title product.

(b) Preparation of 3-chloro-5-propyl-2,6-dihydroxybenzaldehyde

To a solution of 2-chloro-4-propyl-1,5-dihydroxybenzene (from Step a, 243 mg, 1.3 mmol) in 10 mL trifluoroacetic acid was added 1 g of hexamine. The mixture was refluxed for 20 h. Water was added and the mixture was extracted with ethyl acetate. Chromatography of the concentrated organic extracts gave the title compound.

H$^1$ NMR δ 1.95 (t, 3H), 1.6 (m, 2H), 2.55 (t, 2H), 7.3 (s, 1H), 10.45 (s, 1H).

(c) The title compound was prepared according to the methodology of Example 42 using the starting material from Step b above, mp 88° C.

$^1$H NMR (90 MHz, CDCl$_3$) δ 0.9 (t, 3H, J=7 Hz) 1.4 (sextet, 2H, J=7 Hz) 2.55 (t, 2H, J=7 Hz) 3.65 (s, 3H) 3.9 (s, 2H) 6.55 (s, 1H) 6.8 (d, 2H, J=9 Hz) 6.8 (s, 1H) 7.15 (d, 2H, J=9 Hz) 7.18 (s, 1H).

Mass Spec (M+) 330 m/e.

EXAMPLE 52

Preparation of 7-Chloro-4-hydroxy-3-methyl-2-phenyl-5-propylbenzofuran (172)

(a) Methyl-2-phenyl-2-(2-acetyl-3-hydroxy-4-propyl-6-chlorophenoxy) acetate A solution of triphenylphosphine (9.7 g, 37 mmol) in tetrahydrofuran (50 mL) was added dropwise to a mixture of 5-chloro-2,6-dihydroxy-3-propyl-3-propylacetophenone (Example 23, Step a) (5.0 g, 22 mmol), methyl 2-hydroxy-2-phenylacetate (4.2 g, 25 mmol) and diethylazodicarboxylate (6.1 g, 37 mmol) in tetrahydrofuran (200 mL) at 0° C. The mixture was then stirred at room temperature for 1 hour, concentrated and the residue chromatographed on silica gel with 10% ethyl acetate in hexane to obtain the title compound, m.p. 65°–66° C.

Calcd. for C$_{20}$H$_{21}$ClO$_5$: C, 63.74; H, 5.61; Cl, 9.40. Found: C, 63.63; H, 5.98; Cl, 9.50.

(b) 2-Phenyl-2-(2-acetyl-3-hydroxy-4-propyl-6-chlorophenoxy) acetic acid

A mixture of methyl 2-phenyl-2-(2-acetyl-3-hydroxy-4-propyl-6-chlorophenoxy) acetate (Step a) (6.2 g, 16 mmol), 10N sodium hydroxide (10 mL) and methanol (75 mL) was refluxed for 1.5 hours. The mixture was concentrated to remove most of the methanol. The residue was dissolved in water (200 mL) and extracted with diethyl ether to remove neutral material. The aqueous phase was acidified with 6N HCl (100 mL) and extracted with diethyl ether. The ether extract was dried (MgSO$_4$), filtered and concentrated to obtain the title compound, m.p. 131°–133° C.

Calcd. for C$_{19}$H$_{19}$ClO$_5$: C, 62,89; H, 5.27; Cl, 9.77. Found: C, 62.43; H, 5.52; Cl, 9.48.

(c) 4-acetoxy-7-chloro-3-methyl-2-phenyl-5-propylbenzofuran

A mixture of 2-phenyl-2-(2-acetyl-3-hydroxy-4-propyl-6-chlorophenoxy) acetic acid (Step b)(3.4 g, 9.3 mmol), anhydrous sodium acetate (6.8 g, 82 mmol) and acetic anhydride (50 mL) was refluxed for 1 hour. The mixture was cooled, diluted with diethyl ether and the salts filtered off. The filtrate was concentrated and the residue chromatographed on silica gel with 10% ethyl acetate in hexane to obtain the title compound, m.p. 86°–87° C.

Calcd. for C$_{20}$H$_{19}$ClO$_3$: C, 70.07; H, 5.58; Cl, 10.34. Found: C, 70.09; H, 6.03; Cl, 10.54.

(d) 7-chloro-4-hydroxy-3-methyl-2-phenyl-5-propylbenzofuran (172)

A mixture of 4-acetoxy-7-chloro-3-methyl-2-phenyl-5-propylbenzofuran (Step c) (1.5 g, 4.6 mmol), methanol (75 mL) and 3N sodium hydroxide (10 mL) was heated to obtain a solution which was then stirred at room temperature for 2 hours. The mixture was acidified with 1N hydrochloric acid (100 mL) and extracted with diethyl ether. The ether extracts were dried (MgSO$_4$), filtered and concentrated. The residue was slurried with hexane, filtered and washed with hexane to obtain the title compound, m.p. 102°–104° C.

Calcd. for C$_{18}$H$_{17}$ClO$_2$: C, 71.87; H, 5.69; Cl, 11.78. Found: C, 71.52; H, 6 10; Cl, 11 80.

EXAMPLE 53

Preparation of 7-Chloro-4-hydroxy-3-methyl-2-(4'-methoxyphenylmethyl)-5-propylbenzothiophene (171)

(a) O-(2-acetyl-3-hydroxy-4-propyl-6-chlorophenyl) dimethylthiocarbamate

To a stirring mixture of 50% sodium hydride dispersion (2.1 g, 43 mmol) in dimethylformamide (100 mL) under nitrogen atmosphere and with ice-water cooling was added 3-chloro-2,6-dihydroxy-5-propylacetophenone (Example 23, Step a) (10 g, 43 mmol). After stirring for one hour, a solution of dimethylthiocarbamoyl chloride (5.3 g, 43 mmol) in dimethylformamide (25 mL) was added dropwise over 15 minutes. The mixture was then stirred at room temperature for 18 hours, poured into cold 1N HCl (75 mL) and extracted with diethyl ether. The ether layer was backwashed twice with water, dried (MgSO$_4$), filtered, concentrated and chromatographed to obtain the title compound, m.p. 114°–116° C.

Calcd. for $C_{14}H_{18}NSClO_3$: C, 53.24; H, 5.74; N, 4.43; S, 10.15; Cl, 11.22. Found: C, 53.60; H, 5.81; N, 4.23; S, 10.03; Cl, 11.45.

(b) O-(2-acetyl-3-acetoxy-4-propyl-6-chlorophenyl) dimethylthiocarbamate

Acetyl chloride (1.9 g, 25 mmol) was added dropwise to an ice-cold stirring mixture of O-(2-acetyl-3-hydroxy-4-propyl-6-chlorophenyl) dimethylthiocarbamate (6.3 g, 20 mmol) (Step a) and triethylamine (3.0 g, 30 mmol) in tetrahydrofuran (50 mL) The mixture was stirred for 2 hours and then diluted with water and diethyl ether. The organic layer was separated, dried (MgSO$_4$), filtered and concentrated to obtain the title compound as an oil which crystallized on standing. The crystals were slurried with hexane, filtered and dried to give the title compound, m.p. 86°–88° C.

Calcd. for $C_{16}H_{20}NSClO_4$: C, 53.70; H, 5.63; N, 3.91; S, 8.95; Cl, 9.90. Found: C, 53.88; H, 5.65; N, 3.72; S, 8.98; Cl, 10.03.

(c) S-(2-acetyl-3-acetoxy-4-propyl-6-chlorophenyl) dimethylthiocarbamate

A solution of O-(2-acetyl-3-acetoxy-4-propyl-6-chlorophenyl) dimethylthiocarbamate (Step b) (6.8 g, 19 mmol) in o-dichlorobenzene (25 mL) was refluxed under nitrogen atmosphere for 30 hours. The mixture was chromatographed on silica gel, eluting with 20% ethyl acetate in toluene to yield the title compound as an oil.

Calcd. for $C_{16}H_{20}NSClO_4$: C, 53.70; H, 5.63; N, 3.91; S, 8.95; Cl, 9.90. Found: C, 54.51; H, 5.99; N, 3.61; S, 8.94; Cl, 9.77.

(d) 5-chloro-2-hydroxy-6-mercapto-3-propylacetophenone

A solution of 5-(2-acetyl-3-acetoxy-4-propyl-6-chlorophenyl) dimethylthiocarbamate (Step c) (3.5 g, 9.8 mmol) in 1,2-dichloroethane (10 mL) was added dropwise over 2 minutes to a solution of 10 equivalents of boron tribromide in 1,2-dichloroethane (122 mL of 0.8 Molar). The mixture was brought to reflux for 1 hour as nitrogen was passed over the system to expel hydrogen bromide. The mixture was cooled to 0°–5° C. and decomposed with H$_2$O. The organic layer was separated, dried (MgSO$_4$), filtered, concentrated and chromatographed on silica gel eluting with 30% ethyl acetate in hexane to obtain the title compound as an oil.

Mass Spec. (M+) 244 m/e.

(e) 7-Chloro-4-hydroxy-3-methyl-2-(4'-methoxyphenylmethyl)-5-propylbenzothiophene (171)

The title compound was prepared using the methodology of Example 42, using the title compound of Step d for starting material, m.p. 80° C.

$^1$H NMR (90 MHz), δ 0.98 (t, 3H, J=7 Hz) 1.65 (sextet, 2H, J=7 Hz) 2.6 (s, m, 5H) 3.78 (s, 3 H) 4.18 (s, 2H) 5.15 (s, 1H) 6.8 (d, 2H, J=9 Hz) 6.95 (s, 1H) 7.15 (d, 2H, J=9 Hz).

Mass Spec. (M+) 360 m/e.

What is claimed is:

1. A compound of the formula

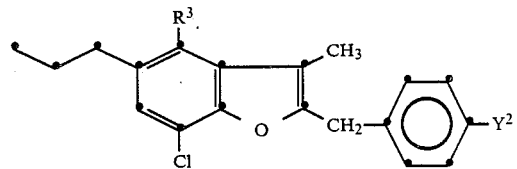

wherein the substituents are selected from:

| R$^3$ | Y$^2$ |
|---|---|
| OAc | OCH$_2$CO$_2$Et |
| OH | OCH$_2$CO$_2$H. |

2. A pharmaceutical composition useful in inhibiting leukotriene formation in mammals comprising an amount of a compound of claim 1 effective as a leukotriene inhibitor and a pharmaceutically acceptable carrier.

3. A method of inhibiting leukotriene action in mammals which comprises administering to a mammal an effective amount of a compound of claim 1

4. A method of treating or ameliorating allergic conditions, asthma, psoriasis, pain, inflammation, or cardiovascular conditions in mammals or inducing cytoprotection in mammals comprising administering to a mammal in need of said treatment an effective amount of a compound of claim 1.

* * * * *